US006923973B1

(12) United States Patent
Cox et al.

(10) Patent No.: US 6,923,973 B1
(45) Date of Patent: Aug. 2, 2005

(54) PEPTIDE AND DNA IMMUNIZATION AGAINST *COCCIDIOIDES IMMITIS* INFECTIONS

(75) Inventors: Rebecca A. Cox, San Antonio, TX (US); D. Mitchell Magee, San Antonio, TX (US); Chengyong Jiang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 24 days.

(21) Appl. No.: 10/081,935

(22) Filed: Feb. 22, 2002

Related U.S. Application Data

(60) Provisional application No. 60/271,031, filed on Feb. 22, 2001.

(51) Int. Cl.[7] .......................... A61K 39/00; C12O 1/68; C12P 19/34; C12H 21/02; C12H 21/04
(52) U.S. Cl. ....................... 424/274.1; 435/6; 435/91.2; 536/24.3; 536/24.31; 536/24.32; 536/24.33
(58) Field of Search ..................... 435/6, 91.2, 342, 435/69.01; 536/24.3, 24.31, 24.32, 24.33, 23.7; 424/274.1, 191.1; 530/388.6

(56) References Cited

U.S. PATENT DOCUMENTS

| | | | |
|---|---|---|---|
| 5,284,747 A | 2/1994 | Milliman ........................ | 435/6 |
| 5,622,827 A | 4/1997 | McAllister et al. ............ | 435/6 |
| 5,837,734 A | 11/1998 | Bartsch et al. ............... | 514/594 |
| 2003/0219455 A1 | 11/2003 | Cole et al. ................ | 424/190.1 |
| 2003/0224013 A1 | 12/2003 | Cole et al. ................ | 424/191.1 |
| 2004/0001843 A1 | 1/2004 | Galgiani et al. ......... | 424/185.1 |
| 2004/0181046 A1 | 9/2004 | Cole et al. ................. | 536/23.1 |

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129–2138, 1990).*
Burgess et al., The Journal of C ll Biology, 111:2129–2138, 1990).*
Jobling et al. ( Mol. Microbiol. 1991, 5(7): 1755–67.*
Accession No.: U39835.*
Accession No.: U32518.*
Cox and Magee, "*Coccidioidomycosis*: Host Response and Vaccine Development," *Clin. Microbiol. Rev.*, 17(4):804–839, 2004.
Abuodeh et al., "Resistance to *Coccidioides immitis* in Mice after Immunization with Recombinant Protein or a DNA Vaccine of a Proline–Rich Antigen," *Infect. Immun.*, 67(6):2935–2940, 1999.
Ampel, et al., "In Vitro Assessment of Cellular Immunity in Human Coccidioidomycosis: Relationship Between Dermal Hypersensitivity, Lymphocyte Transformation, and Lymphokine Production by Peripheral Blood Mononuclear Cells from Healthy Adults," *J. Infect. Dis.*, 165:710–715, 1992.

Corry et al., "Cytokine Production by Peripheral Blood Mononuclear Cells in Human Coccidioidomycosis," *J. Infect. Dis.*, 174:440–443, 1996.
Cox and Magee, "Vaccine Efficacy of *Coccidiodies immitis* Antigen 2, " Progress Report submitted to California State Bakersfield Foundation, Valley Fever Vaccine Project Meeting, Report for Period Jul. 1, 2000–Dec. 31, 2000, Meeting held Dec. 4–5, 2000.
Cox and Magee, "Vaccine Efficacy of *Coccidioides immitis* Antigen 2," Progress Report submitted to California State Bakersfield Foundation, Valley Fever Vaccine Project Meeting Report Period Jan. 1, 1980–Dec. 31, 1999. Meeting held Feb. 22–23, 2000.
Cox and Magee, "Vaccine Efficacy of *Coccidioides immitis* Antigen 2," Progress Report sumbitted to California State Bakersfield Foundation, Valley Fever Vaccine Project Meeting, Report for Period Jan. 1, 2000–Jun. 31, 2000. Meeting held Jun. 13–14, 2000.
Cox and Magee; U.S. Appl. No. 60/178,571; Entitled "Use of DNA and Expressed Protein as a Vaccine Against Coccidiodidomycosis"; by Rebecca A. Cox and D. Mitchell Magee; filed Jan. 28, 2000.
Cox and Magee, "Protective Immunity in Coccidioidomycosis," *Res. Immunology*, 149:417–428, 1998.
Dugger et al., "Cloning and Sequence Analysis of the cDNA for a Protein from *Coccidioides immitis* with Immunogenic Potential," *Biochem. Biophys. Res. Comm.*, 218:485–489, 1996.
Franco et al., "An Immunodominant Cytotoxic T Cell Epitope on the VP7 Rotavirus Protein Overlaps the H2 Signal Peptide," *J. Gen. Viro.*, 74:2579–2586, 1993.
Hombach et al., "Strictly Transporter of Antigen Presentation (TAP)–Dependent Presentation of an Immunodominant Cytotoxic T Lymphocyte Epitope in the Signal Sequence of a Virus Protein," *J. Exp. Med.*, 182:1619, 1995.
Jiang et al., "Genetic Vaccination Against *Coccidioides immitis*: Comparison of Vaccine Efficacy of Recombinant Antigen 2 and Antigen 2 cDNA," *Infect. Immun.*, 67(2):630–635, 1999.
Kirkland et al., "Evaluation of the Proline–Rich Antigen of *Coccidioides immitis* as a Vaccine Candidate in Mice," *Infect. Immun.*, 66(8):3519–3522, 1998.

(Continued)

*Primary Examiner*—Lynette R. F. Smith
*Assistant Examiner*—Padma Baskar
(74) *Attorney, Agent, or Firm*—Myers Bigel Sibley & Sajovec, P.A.

(57) ABSTRACT

Disclosed are peptide and DNA compositions surprisingly found to be effective in generating immune responses against the pathogenic fungi *Coccidioides* spp., the causative agents of coccidioidomycosis and Valley Fever. The invention thus provides peptides and DNA constructs, combinations and related biological compositions, and prophylactic and therapeutic methods of using such components to generate effective immune responses against *Coccidioides* spp., including *C. immitis*.

13 Claims, 18 Drawing Sheets-

OTHER PUBLICATIONS

Kondo et al., "A Single Retroviral Gag Precursor Signal Peptide Recognized by FBL–3 Tumor–Specific Cytotoxic T. Lymphocytes," *J. Virol.*, 69(11):6735–6741, 1995.

Pan and Cole, "Molecular and Biochemical Characterization of a *Coccidioides immitis*—Specific Antigen," *Infect. Immun*, 63(10):3994–4002, 1995.

Stevens, "Current Concepts: Coccidioidomycosis," *N. Eng. J. Med.*, 332:1077–1082, 1995.

Zhu et al., "Identification of a *Coccidioides immitis* Antigen 2 Domain That Expresses B–Cell Reactive Epitopes," *Infect. Immun.*, 65(8):3376–3380, 1997.

Zhu et al., "*Coccidioides immitis* Antigen 2: Analysis of Gene and Protein," *Gene*, 181:121–125, 1996.

Zhu et al., Molecular Cloning and Characterization of *Coccidioides immitis* Antigen 2cDNA, *Infect. Immun.*, 64(7):2695–2699, 1996.

U.S. Appl. No. 10/417,923; Entitled: "Peptides and DNA Encoding the Peptides Useful for Immunizations Against *Coccidioides* SPP. Infections," by John N. Galgiani, Kris Orsborn, Tao Peng and Lisa Shubitz; filed Apr. 16, 2003, claiming priority to U.S. Appl. No. 60/373,635, filed Apr. 19, 2002.

* cited by examiner

SEQUENCE LISTING

<160> NUMBER OF SEQ ID NOS: 9

<210> SEQ ID NO 1
<211> LENGTH: 52
<212> TYPE: DNA
<213> ORGANISM: Coccidioides Immitis

<400> SEQUENCE: 1 atgcag

-continued

```
1               5                   10                  15

Ser Ala Gln Leu Pro Asp Ile Pro Pro Cys Ala Leu Asn Cys Phe Val
            20                  25                  30

Glu Ala Leu Gly Asn Asp Gly Cys Thr Arg Leu Thr Asp Phe Lys Cys
        35                  40                  45

His Cys Ser Lys Pro Glu Leu Pro Gly Gln Ile Thr Pro Cys Val Glu
    50                  55                  60

Glu Ala Cys Pro Leu Asp Ala Arg Ile Ser Val Ser Asn Ile Val Val
65                  70                  75                  80

Asp Gln Cys Ser Lys Ala Gly Val Pro Ile Asp Ile Pro Pro Val Asp
                85                  90                  95

Thr Thr Ala Ala Pro Glu Pro Ser Glu Thr Ala Glu Pro Thr Ala Glu
            100                 105                 110

Pro Thr Glu Glu Pro Thr Ala Glu Pro Thr Ala Glu Pro Thr Ala Glu
        115                 120                 125

Pro Thr His Glu Pro Thr Glu Glu Pro Thr Ala Val Pro Thr Gly Thr
    130                 135                 140

Gly Gly Gly Val Pro Thr Gly Thr Gly Ser Phe Thr Val Thr Gly Arg
145                 150                 155                 160

Pro Thr Ala Ser Thr Pro Ala Glu Phe Pro Gly Ala Gly Ser Asn Val
                165                 170                 175

Arg Ala Ser Val Gly Gly Ile Ala Ala Ala Leu Leu Gly Leu Ala Ala
            180                 185                 190

Tyr Leu
```

<210> SEQ ID NO 5
<211> LENGTH: 30
<212> TYPE: DNA
<213> ORGANISM: Coccidioides immitis

<400> SEQUENCE: 5
ttgggatccg tcgacatgca gttctctcac 30

<210> SEQ ID NO 6
<211> LENGTH: 31
<212> TYPE: DNA
<213> ORGANISM: Coccidioides immitis

<400> SEQUENCE: 6
ggaagatctc gagttaggca ctggcgaggc c 31

<210> SEQ ID NO 7
<211> LENGTH: 24
<212> TYPE: DNA
<213> ORGANISM: Coccidioides immitis

<400> SEQUENCE: 7
atgcagttct ctcacgctct catc 24

<210> SEQ ID NO 8
<211> LENGTH: 24
<212> TYPE: DNA
<213> ORGANISM: Coccidioides immitis

<400> SEQUENCE: 8
atgcagctcc cagacatccc acct 24

<210> SEQ ID NO 9

-continued

```
<211> LENGTH: 21
<212> TYPE: DNA
<213> ORGANISM: Coccidioides immitis

<400> SEQUENCE: 9
ttacaggtag gcagcgagac c                                              21
```

PEPTIDE AND DNA IMMUNIZATION AGAINST *COCCIDIOIDES IMMITIS* INFECTIONS

The present application claims priority to U.S. provisional application Ser. No. 60/271,031, filed Feb. 22, 2001, the entire text, figures and sequences of which application are incorporated herein by reference without disclaimer.

BACKGROUND OF THE INVENTION

1. Field of the Invention

The present invention relates generally to the fields of pathogenic fungi and immunology. More particularly, the invention provides compositions of peptides and genetic constructs expressing the peptides and methods of using such compositions in generating effective immune responses against pathogenic *Coccidioides* spp. fungi, such as *C. immitis*. The compositions, combinations and methods of the invention are thus useful in prophylactic and therapeutic applications to combat coccidioidomycosis and Valty Fever, the diseases caused by *Coccidioides* spp. infection.

2. Description of Related Art

*Coccidioides* spp., including *C. immitis* and *C. posadasii*, are pathogenic fungi endemic to the southwestern United States, including parts of Texas, California, Nevada, Utah, Arizona and New Mexico, parts of Mexico and in other countries in Central and South America. *C. immitis* was first described, and is now becoming known as the Californian population. The *C. posadasii* species was recently defined, and was previously recognized as the non-Californian population of *C. immitis* (Fisher et al., 2002).

The *Coccidioides* spp. organisms grow in the soil and, following winter rains, produce arthroconidia. Infection of mammals generally occurs in the summer months when hot, dry conditions favor inhalation of *Coccidioides* spp. arthroconidia spread by wind or by physical disturbance of infected soil. *Coccidioides* spp. infection causes disease in dogs and cats, amongst other mammals.

In humans, infection by *C. immitis* and *C. posadasii* leads to coccidioidomycosis, also known as the disease Valley Fever (or San Joaquin Valley Fever). An estimated 100,000 persons are infected each year (Stevens, 1995). The disease can range from a primary, asymptomatic infection to a disseminated process involving virtually any organ in the body, with the exception of the gastrointestinal tract. High risk groups include persons of Asian, Black, or Hispanic ancestry, pregnant females, older persons, and those who are immunocompromised. The morbidity and mortality of the disease causes problems for those living in the relevant geographical areas. The need for effective immunization strategies is further emphasized by increased travel and urbanization of the endemic areas.

Certain methods are available to treat coccidioidomycosis in mammals, including systemic anti-fungal therapies. In humans, the available treatment methods are limited by problems of patient tolerance and drug resistance. The development of preventative measures is preferred over methods to treat the infection once it has occurred. Unfortunately, although certain immunization strategies have been explored, there remains in the art a need to identify biological components that generate effective immune responses against *Coccidioides* spp. The identification of smaller immunogenic components and/or those that elicit cell-mediated immune responses would be a particular advance in this area.

SUMMARY OF THE INVENTION

The present invention overcomes various drawbacks and addresses the long felt need in the art by providing *Coccidioides* spp. peptide and gene compositions for prophylactic and therapeutic uses. The invention particularly concerns the discovery that defined signal peptide sequences from the N-terminus of a *Coccidioides* antigen, and genetic constructs encoding such sequences, are surprisingly effective in generating protective immune responses against *Coccidioides* spp. fungi. The invention thus provides a range of compositions, kits and combinations comprising such peptides and genetic constructs and methods of using these agents to prevent, reduce or treat *Coccidioides* spp. infections, coccidioidomycosis and Valley Fever in animals and humans.

The invention particularly relates to isolated peptides with sequences based upon the N-terminal signal peptide from the *Coccidioides* spp. antigen termed Ag2 or Ag2/PRA, and DNA constructs encoding such sequences. In certain embodiments, the peptides and constructs of the invention have sequences related to the 18 N-terminal amino acids that are usually cleaved from the Ag2/PRA protein. Methods, uses and medicaments involving the application of such peptides and genetic constructs in the immunization against *Coccidioides* spp. fungi and the prevention and treatment of related diseases and conditions are particularly provided.

In exemplary embodiments, the isolated and/or purified peptides of the invention, and the DNA sequences that encode such peptides, have defined sequences that substantially correspond to (or encode) the 18 amino acid signal peptide sequence MQFSHALIALVAAGLASA (SEQ ID NO:2) from the N-terminus of Ag2/PRA. Such peptides and the corresponding DNA sequences are herein shown to be surprisingly effective in eliciting protective immune responses against *Coccidioides* spp.

Data are provided to show that immunization with a genetic construct encoding the selected peptides protects animals against challenge with *Coccidioides* spp. to substantially the same degree as immunization with a construct encoding the entire Ag2/PRA antigen, which is 194 amino acids in length. Although in no way bound by the present reasoning, the inventors believe that the signal sequences and related peptides of the invention function to elicit cell-mediated immune (CMI) responses, such as cytotoxic T cell (cytotoxic T lymphocyte, CTL) responses, against the invading fungi.

The various surprising features of the invention thus include the ability of a peptide that is normally cleaved from its parent antigen to provide protection, the ability of such peptides to perform essentially as well as the intact protein of more than ten times the length and the involvement of cell-mediated immune responses in *Coccidioides* spp. vaccination. In addition to the foregoing and other surprising features, the invention has many practical advantages, such as the new-found ability to prepare short peptides and small genetic constructs for use as vaccines, which is more cost-effective and less labor-intensive.

Although surprisingly unique in its discovery, and effective even in its simplest forms, the invention further provides a range of biological components and methods based upon the initial findings. For example, the invention provides peptides, and genetic constructs encoding such peptides, that are shorter, longer, derivatized and optimized; epitopic core sequences from such peptides; mimetics; fusion proteins involving such peptides and other sequences, such as additional epitopes, targeting sequences and/or endoplasmic reticulum (ER) insertion sequences; formulations of such peptides and constructs with a range of selected adjuvants, including poly(lactide-co-glycolide) (PLG) microparticle adjuvants; and multimers and combinations of such peptides, including those packaged into "multiple antigen peptide (MAP)" constructs using carriers such as a lysine-glycine core.

Additional compositions of the invention are isolated proteins and polypeptides, and genetic constructs encoding such proteins and polypeptides, in which the natural cleavage site between the N-terminal signal peptide (1–18) and the remainder of the protein (19–194) is removed and/or modified so that expression of the construct, whether in vitro or in vivo, always yields the full-length Ag2/PRA(1–194) recombinant antigen, including the 18 N-terminal amino acids newly discovered to be important for immunoprotection.

An example is an isolated nucleic acid segment that comprises at least a first modified coding region that encodes a protein of at least about 100 amino acids in length that comprises an amino acid sequence that is at least about 90% identical to at least about 100 contiguous amino acids of the amino acid sequence of SEQ ID NO:4; wherein the modified coding region encodes a protein in which the native cleavage site between amino acids 18 and 19 of SEQ ID NO:4 is modified to substantially prevent cleavage upon expression of the isolated nucleic acid segment in a recombinant host cell, including a cell in vivo.

The mode of administration the peptide and/or genetic vaccine constructs can also be varied and optimized, if desired. Including, for example, changing the amount, route, number and timing of the immunizations, and combining the immunizations with defined adjuvants and other immunogens, optionally in prime and boost embodiments and other combined prophylactic and therapeutic protocols.

All such compositions and methods can be used without undue experimentation in light of the present disclosure. Although particularly useful in vaccination, the *Coccidioides* spp. peptide and DNA compositions of the invention are further useful in a variety of other embodiments, including as biological tools, for use in diagnosis and even for therapy of other fungal conditions.

In exemplary embodiments, the invention provides compositions and isolated nucleic acid segments that comprise at least a first isolated coding region that encodes a peptide of between about 7, 8, 9, 10, 11 or about 12 amino acids in length and about 35, 36, 37, 38, 39 or about 40 amino acids in length that comprises at least one cell-mediated immune response epitope from SEQ ID NO:2.

The encoded peptide may be between about 15, 16, 17 or 18 amino acids in length and about 35, 36, 37, 38, 39 or about 40 amino acids in length and comprise an amino acid sequence that is at least about 77%, 83%, 88% or 94% identical or homologous to the amino acid sequence of SEQ ID NO:2. The encoded peptide will preferably be between about 15, 16, 17 or 18 amino acids in length and about 19, 20, 21, 22, 23, 24, 25, 26, 27 and about 28 amino acids in length and will preferably comprise an amino acid sequence that is at least about 77%, 83%, 88% or 94% identical or homologous to the amino acid sequence of SEQ ID NO:2.

In certain embodiments, the compositions and isolated nucleic acid segments comprise at least a first isolated coding region that encodes a first peptide comprising the amino acid sequence of SEQ ID NO:2. In other embodiments, the encoded peptide has the amino acid sequence of SEQ ID NO:2.

Further aspects of the invention are compositions and isolated nucleic acid segments in which the at least a first isolated coding region comprises the nucleotide sequence of SEQ ID NO:1. In other embodiments, the at least a first isolated coding region has the nucleotide sequence of SEQ ID NO:1.

In the compositions and isolated nucleic acid segments, the at least a first isolated coding region is preferably positioned under the control of a promoter. Such constructs are therefore further defined as recombinant vectors, which are preferably comprised within recombinant host cells. The recombinant vectors and host cells preferably express the isolated coding region to produce the encoded peptide or polypeptide.

The nucleic acid segments and recombinant vectors of the invention can further comprise at least a second isolated coding region that encodes a second protein, polypeptide or peptide. The second isolated coding region may encode a second, distinct *Coccidioides* spp. protein, polypeptide or peptide, such as a second, distinct polypeptide or peptide sequence from SEQ ID NO:4. A "second, distinct" *Coccidioides* spp. protein, polypeptide or peptide means a protein, polypeptide or peptide "distinct from", i.e., in addition to, the peptide encoded by the first isolated coding region.

Alternatively, the at least a second isolated coding region may encode further copies of the first peptide. Such expression constructs may be used to prepare a plurality of isolated peptides, which can be operatively assembled into a multiple antigen peptide (MAP) construct.

In either of such embodiments, the overall nucleic acid segment may comprise separate first and second isolated coding regions, wherein the first and second proteins, polypeptides or peptides are produced separately from each other, such that they exist as a mixture. In other embodiments, the first and second isolated coding regions are operatively attached, in frame, wherein the overall nucleic acid segment then encodes a fusion protein, in which the first peptide is operatively linked to the second protein, polypeptide or peptide.

Further examples of the nucleic acid segments and recombinant vectors of the invention are those in which the second isolated coding region encodes an adjuvant protein, polypeptide or peptide. Again, the adjuvant may be produced as a separate entity or as a fusion protein with the first peptide.

Yet further examples are wherein the at least a second isolated coding region encodes an endoplasmic reticulum insertion sequence, such as an adenovirus glycoprotein-derived endoplasmic reticulum insertion sequence.

The nucleic acid segments of the claimed invention may be comprised within a pharmaceutically acceptable carrier or diluent, such that a pharmaceutical composition or vaccine formulation results. Such composition further comprises at least a first adjuvant. An exemplary adjuvant is a poly(lactide-co-glycolide) (PLG) microparticle adjuvant. These pharmaceutical compositions or vaccine formulations preferably comprise an immunologically effective amount of the at least a first isolated nucleic acid segment.

The recombinant host cells of the present invention may be maintained in vitro, e.g., for recombinant protein, polypeptide or peptide production. Equally, the recombinant host cells could be host cells in vivo, such as results from immunization of an animal or human with a nucleic acid segment of the invention. Accordingly, the recombinant host cells may be prokaryotic or eukaryotic host cells, such as *E. coli*, yeast, mammalian or human host cells. The host cells will often further comprise at least a second isolated coding region that encodes a second protein, polypeptide or peptide, such as a second, distinct *Coccidioides* spp. protein, polypeptide or peptide.

The invention further provides the peptides encoded by any of the foregoing isolated nucleic acid segments and similar peptides may be automated synthesis, or purified following cleavage. Such peptides may be between about 7, 8, 9, 10, 11 or about 12 amino acids in length and about 35, 36, 37, 38, 39 or about 40 amino acids in length and comprises at least one cell-mediated immune response epitope from SEQ ID NO:2.

Other peptides may be between about 15, 16, 17 or 18 amino acids in length and about 35, 36, 37, 38, 39 or about 40 amino acids in length and comprise an amino acid sequence that is at least about 77%, 83%, 88% or 94% identical or homologous to the amino acid sequence of SEQ ID NO:2. The peptides will preferably be between about 15, 16, 17 or 18 amino acids in length and about 19, 20, 21, 22, 23, 24, 25, 26, 27 and about 28 amino acids in length and will preferably comprise an amino acid sequence that is at least about 77%, 83%, 88% or 94% identical or homologous to the amino acid sequence of SEQ ID NO:2. In certain embodiments, the peptides comprise the amino acid sequence of SEQ ID NO:2 or have the amino acid sequence of SEQ ID NO:2.

The peptides may be comprised within a pharmaceutically acceptable carrier or diluent, such that a pharmaceutical composition or vaccine formulation results, which may optionally further comprise at least a first adjuvant. These pharmaceutical compositions, antigen compositions or vaccine formulations preferably comprise an immunologically effective amount of the at least a first peptide.

The adjuvant may be a poly(lactide-co-glycolide) (PLG) microparticle adjuvant, in which case the at least a first isolated peptide may be encapsulated within the PLG microparticles.

In certain embodiments, such compositions will comprise a plurality of isolated peptides operatively assembled into a multiple antigen peptide (MAP) construct, such as linked to a lysine-glycine core.

Antigenic cocktails or polypotent vaccines of the invention result wherein the pharmaceutical or antigen compositions or vaccine formulations further comprise a combined immunogenic amount of at least a second antigenic *Coccidioides* spp. component.

The invention further provides a number of methodological embodiments. For example, methods for generating an immune response, comprising providing to an animal or human an immunologically effective amount of at least a first isolated nucleic acid segment or at least a first isolated peptide in accordance with the present invention. The animal or human subject may have, be suspected of having or at risk for developing coccidioidomycosis or Valley Fever.

Accordingly, the invention provides methods for treating coccidioidomycosis or Valley Fever, comprising administering to an animal or human having or suspected of having coccidioidomycosis or Valley Fever, a therapeutically effective amount of at least a first isolated nucleic acid segment or at least a first isolated peptide in accordance with the present invention.

Still further embodiments of the invention are methods for reducing, preventing or vaccinating against coccidioidomycosis or Valley Fever. Such methods comprise administering to an animal or human suspected of having, or at risk for developing, coccidioidomycosis or Valley Fever a pharmaceutically acceptable composition comprising a prophylactically effective amount of at least a first isolated nucleic acid segment or at least a first isolated peptide in accordance with the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Colony forming units (CFU) in Ag2/PRA-GST-immunized mice after i.p. challenge with 250 arthroconidia. FIG. 1B. Mortality in rAg2/PRA-GST-immunized mice after i.p. challenge with 250 arthroconidia.

FIG. 2A. CFU in Ag2/PRA vector-immunized mice after i.p. challenge with 2,500 arthroconidia FIG. 2B. Mortality in Ag2/PRA vector-immunized mice after i.p. challenge with 2,500 arthroconidia.

FIG. 6A. CFU in lungs of the immunized mice. FIG. 6B. CFU in spleens of the immunized mice.

DESCRIPTION OF ILLUSTRATIVE EMBODIMENTS

I. *Coccidioides* spp. Infections and Disease

Figure 1A:
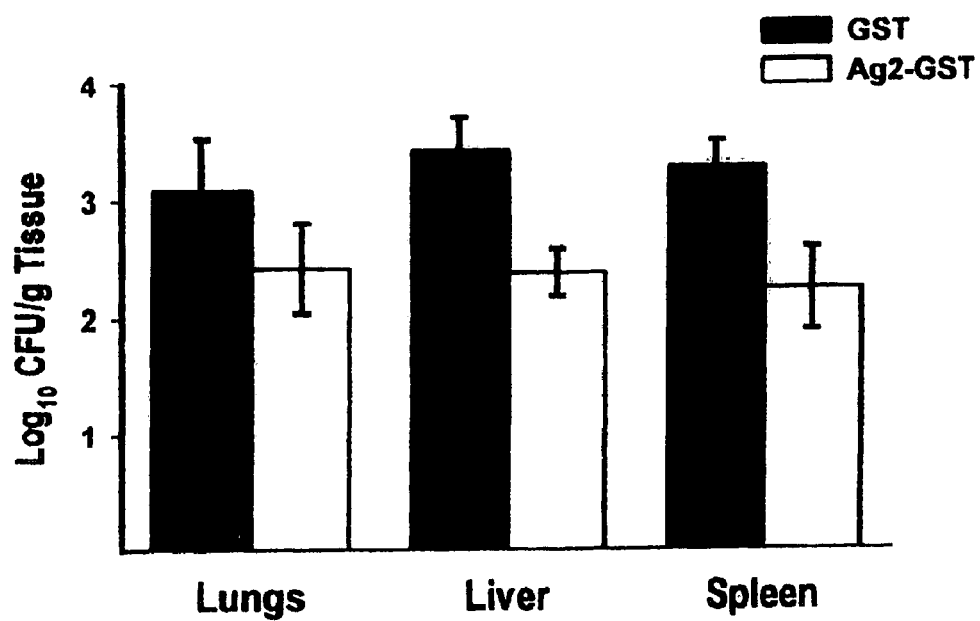
FIG. 1A and FIG. 1B. Immunization of mice with full length Ag2/PRA recombinant protein. BALB/c mice were immunized with three weekly injections of 100 µg of recombinant Ag2/PRA-GST protein in RIBI adjuvant and then challenged with 250 arthroconidia of *C. immitis* strain Silveira via the intraperitoneal (i.p.) route.

*Coccidioides* spp., such as *C. immitis* and *C. posadasii*, are geophilic, dimorphic fungi that are endemic to the southwestern United States, parts of Mexico and in Central and South America. Infection with these fungal pathogens causes coccidioidomycosis (San Joaquin Valley Fever), a respiratory disease (Pappagianis, 1980; Stevens, 1995). The incidence of coccidioidomycosis in the southwestern United States sharply increased in the early 1990's as a result of environmental and demographic changes (Pappagianis, 1994).

Primary infection occurs via inhalation of mycelial-phase arthroconidia, which enter the alveoli and undergo a morphogenetic conversion to a parasitic, spherule form of growth. These large spherules (20 to 100 μm) grow, mature and divide internally to produce endospores. When released, the endospores spread the *Coccidioides* spp. infection locally or to distant sites via the lymphatic system or blood. The disease has diverse manifestations, ranging from a benign pulmonary infection to a progressive disseminated disease most commonly involving the skin, bones and/or joints and central nervous system.

Acute, primary pulmonary coccidioidomycosis usually occurs within one to three weeks following *Coccidioides* spp. infection. Early clinical signs may be absent or include a mild nonproductive cough, low-grade fever, partial anorexia, and weight loss. This form of disease is often self-limiting, but may progress to disseminated infection. Disseminated pulmonary coccidioidomycosis causes a more severe productive cough due to widespread lung involvement and tracheobronchial lymphadenopathy. Systemic signs include an antibiotic-unresponsive fluctuating fever, depression, weakness, anorexia, and weight loss. *Coccidioides* spp. may spread beyond the pulmonary tree, affecting any organ or system in the body.

Currently available treatments for coccidioidomycosis include systemic anti-fungal therapies. For example, the imidazoles such as ketoconazole and itraconazole are used for the treatment of coccidioidomycosis in the dog and cat. Liposome-encapsulated amphotericin B has also been shown to be safe and effective in the treatment of coccidioidomycosis in those dogs that cannot tolerate oral imidazole therapy. However, *C. immitis* is more resistant to amphotericin B than the other systemic mycotic agents.

In the clinical arena, problems of patient tolerance and drug resistance exist that limit the currently available treatments. Even if effective treatment strategies could be developed, this only attends to the infected individuals, and does not combat the disease at large. Preventative measures are therefore urgently needed to provide effective immunization against *Coccidioides* spp.

Evidence from clinical and experimental investigations revealed that the severity of coccidioidomycosis directly correlates with depressed cell-mediated immunity to coccidioidal antigens (Ampel et al., 1992; Corry et al., 1996, Cox et al, 1977; 1988; Cox and Magee, 1998; Cox and Vivas, 1977; Magee and Cox, 1995). Recovery from primary infection is associated with strong cell-mediated immune responses to *C. immitis* and is accompanied by life-long immunity to exogenous reinfection (Cox, 1993; Stevens, 1995). The present inventors therefore reasoned that developing a vaccine was a feasible and promising strategy against *Coccidioides* spp. in regions endemic to this fungal pathogen.

Previous vaccine studies using experimental animal models demonstrated that immunization with killed spherules induces protection against pulmonary challenge with a lethal dose of arthroconidia (Kong et al., 1963; Levine et al., 1961; 1965). Investigations showed that the protective component (s) resided primarily in the cell walls of killed spherules (Kong et al., 1963; Levine et al., 1961; Pappagianis et al., 1979).

II. Antigen 2 (Ag2/PRA)

A *Coccidioides immitis* cell wall extract was shown to elicit delayed-type hypersensitivity reactions in Coccidioides-immunized animals and to protect mice against challenge with this pathogenic fungus. Subsequent studies showed that cell wall extracts enriched in a component termed "Antigen 2 (Ag2)" as an active component induced protection against challenge with *C. immitis* (Cox, 1989; Lecara et al., 1983).

Ag2 is a heavily glycosylated protein present in the cell walls of *Coccidioides* spp. mycelial- and spherule-phase cells (Cox, 1989; Lecara et al., 1983; Zhu et al., 1995; 1996b; Jiang et al., 1999). The Ag2 cDNA was cloned using a spherule-derived cDNA expression library (Zhu et al., 1995; 1996a; 1996b). The cloned cDNA (SEQ ID NO:3) contains a 582 bp open reading frame (ORF) that encodes a 19.4 kDa protein (SEQ ID NO:4).

The native and recombinant antigen represented by SEQ ID NO:3 and SEQ ID NO:4 have been termed "Ag2" based upon the original designation by Huppert et al. (1978) in their 2D-IEP analyses of coccidioidin (CDN). Concurrently, a cDNA was cloned and the encoded antigen designated as proline rich antigen or "PRA" (Dugger et al., 1996; Kirkland et al., 1998). A comparison of the nucleic acid sequence of the Ag2 cDNA and PRA cDNA showed that the two were identical. For this reason, the nomenclature "Ag2/PRA" is appropriate.

The deduced primary tanslation product of Ag2/PRA has 194 amino acids (SEQ ID NO:4), containing a hydrophobic N-terminal of 18 amino acids that has sequence homology to signal peptide sequences, a central region containing 10 examples of a tetrapeptide repeat (TXX'P), and a C-terminal GPI anchor site. These features are consistent with a prepro-Ag2/PRA undergoing a post-translational modification to yield a mature glycosylated Ag2/PRA protein that is anchored on the plasma membrane of spherule- and mycelial-phase cells of this dimorphic fungus.

Using sequence comparison algorithms, the Ag2/PRA protein has been predicted to express T and B cell epitopes, the most prominent of which are said to be in an internal hydrophilic domain that contains tetrapeptide repeats (Zhu et al., 1996b). A subsequent report indicated that Ag2/PRA expresses linear and conformational B cell epitopes localized within amino acids 19–96 (Zhu et al., 1997). Kirkland et al. (1998), Jiang et al. (1999) and Abuodeh et al. (1999) have reported the use of the full length Ag2/PRA recombinant protein and/or full length cDNA as a vaccine with varying degrees of success in animals challenged with *C. immitis* via the intraperitoneal route.

The Ag2/PRA is present in C-ASWS, an alkali-soluble, water-soluble cell wall extract (Lecara et al., 1983). In addition, the Ag2/PRA is herein shown to be present in the 27K vaccine prepared as the supernatant fraction obtained from lysed spherules that had been centrifuged at 27,000 g (Zimmermann et al., 1998). The 27K vaccine is particularly effective, being comparable in its vaccine potential to FKS (Zimmermann et al., 1998).

III. Improved *Coccidioides* spp. Immunogens

The present inventors undertook various lines of investigation to examine the vaccine potential of Ag2/PRA; including analyses of native Ag2/PRA, as present in the 27K vaccine; recombinant Ag2/PRA polypeptides; and Ag2/PRA gene vaccines. In these analyses, the inventors made important and surprising discoveries.

Ag2/PRA cDNA was subcloned into the pGEX plasmid and expressed as a glutathione-S-transferase (GST) fusion protein (rAg2-GST) in *E. coli* (Zhu et al., 1995; Jiang et al., 1999). Immunization of BALB/c mice, which are highly susceptible to *C. immitis*, with the recombinant fusion protein induced immunity against intraperitoneal challenge with 250 arthroconidia of *C. immitis* strain Silveira, as judged by a reduction in the CFU in the livers and spleens ($p<0.025$ by Wilcoxin rank sums test) and a marginal reduction ($p=0.052$) in the lungs.

In certain studies, the rGST-Ag2 protein did not increase the survival of the vaccinated mice over a 30-day period post-infection. Results from other studies have reported that Ag2/PRA expressed as a His-tagged fusion protein in *E. coli* protected BALB/c mice against pulmonary challenge with 30 arthroconidia, as well as intraperitoneal challenge with 50 arthroconidia (Kirkland et al., 1998; Abuodeh et al., 1999).

Since studies in other models have shown that genetic vaccination was often superior to vaccination with recombinant or native peptides, studies were done to assess the vaccine efficacy of Ag2/PRA cDNA (1–194). In evaluating the efficacy of the Ag2/PRA gene vaccine, various positive results were obtained. The gene vaccine induces a very strong level of protection against intraperitoneal challenge, as judged by CFU in the lungs, livers, and spleen and by the survival of 100% of the vaccinated mice as compared to mice given the vector alone. Mice vaccinated with the Ag2/PRA cDNA showed increased production of the T-helper 1 cytokine interferon-$\gamma$ (IFN-$\gamma$). The Th1 response is known to be important in host defenses against this fungus (Cox, 1993; Cox and Magee, 1998; Ampel et al., 1992; Corry et al., 1996).

When evaluated in mice challenged by the pulmonary route, the Ag2/PRA gene vaccine induced protection against dissemination, but did not protect mice at the lung level. Protection at the lung level is contemplated using a plasmid vector that targets the gene to the lungs and/or using modified immunization protocols. The use of a plasmid vector that stimulates Class I cytotoxic CD8+ T cells is particularly contemplated.

The negative results with the recombinant proteins, in that the recombinant Ag2/PRA-GST induced only a low level of protection against i.p. challenge, are informative. The inventors postulated that the low vaccine efficacy of the *E. coli*-expressed rGST-Ag2/PRA might be attributable to the absence of post-translational modification, notably O-glycosylation (Cole et al., 1985), which might be important in antigen presentation or processing (Jentoft, 1990). Expression of Ag2/PRA in the eukaryotic *Pichia pastoris* (yeast) effected post-translational modifications, but did not enhance the vaccine efficacy of the recombinant GST-Ag2/PRA product.

The possibility that the *Pichia*-expressed rAg2/PRA was not O-glycosylated, or at least not in a manner analogous to the native Ag2/PRA, cannot be excluded. However, this evidence, in which a truncated version of Ag2/PRA was used, rather than the full-length Ag2/PRA, instead suggested the inventors that the full-length antigen may be required for optimal processing and presentation.

Studies were therefore undertaken to delineate the immunoprotective domain of Ag2/PRA cDNA. For these studies, Ag2/PRA cDNA (1–194) and a series of PCR™-generated truncations were constructed, ligated to the pVR1012 plasmid, and evaluated for their vaccine efficacy. BALB/c mice immunized with the full-length Ag2/PRA cDNA (1–194) were protected against challenge, whereas mice immunized with Ag2/PRA cDNA (19–194), which lacked the N-terminal signal peptide, were significantly less protected.

The finding that the full-length, but not the 19–194 truncated Ag2/PRA cDNA, protected mice against challenge suggested that the N-terminal 18 amino acids (signal peptide) was important in inducing protective immunity. Further studies were conducted to generate the Ag2/PRA cDNA (1–18) construct and to compare the effect of the Ag2/PRA cDNA (1–18) construct directly with Ag2/PRA cDNA (1–194) and Ag2/PRA cDNA (19–194). The results established that the signal peptide construct induced protection in mice after intraperitoneal challenge with a lethal dose of 2,500 *C. immitis* arthroconidia to a level comparable to that induced by the full-length Ag2/PRA cDNA.

The immunizing capacity of the Ag2/PRA (1–18) signal sequence was not attributable to a nonspecific immunostimulatory effect of DNA, as evidenced by the fact that mice immunized with a frame-shift mutation of Ag2/PRA (1–18) were not protected against challenge. Furthermore, a synthetic peptide corresponding to the translated sequence of Ag2/PRA (1–18) DNA protected mice, albeit at a lower level than the Ag2/PRA (1–1 8) DNA vaccine.

Thus, the present invention fundamentally concerns compositions and methods based on the N-terminal sequence of the Ag2/PRA protein. The term "Ag2/PRA(1–18)" is often used herein for simplicity, notwithstanding that various modifications and combinations of this sequence are disclosed herein and will be understood to be encompassed by the claimed invention. The present invention is the first study to establish that a signal peptide-sequence alone, administered as a gene vaccine or synthetic peptide, can induce protective immunity against a microbial pathogen.

The protection induced with the signal gene vaccine correlated with the production of IFN-γ when splenocytes from Ag2/PRA (1–1 8)-immunized mice were stimulated with recombinant full-length Ag2 and was not associated with the production of anti-*Coccidioides* IgG antibody. The protective capacity of the Ag2/PRA cDNA (1–18) construct, together with the importance of T cell immunity in host defense against *Coccidioides* spp., prompted a data base search to determine whether the signal peptide included T-cell reactive epitopes. The results revealed the presence of three putative Class I MHC-reactive domains, and indicate that the signal peptide likely includes an epitope that induces cell-mediated immune responses, such as those mediated by cytotoxic T cells (QFSHALIAL; residues 2 through 10 of SEQ ID NO:2).

The data in the present disclosure is the first evidence that cytotoxic T cells likely have a role in host protection in coccidioidomycosis. Although previously unconnected with the fields of fungal infection and vaccination in general, and Coccidioidomycosis in particular, there is a documented phenomenon of signal peptides cleaved from larger proteins stimulating cytotoxic T cells (Franco et al., 1993; Kondo et al., 1995).

Prior to the present invention, there was no structural or functional information to suggest that the 18-mer N-terminal peptides of the invention had any function other than as signal peptides that are cleaved from the Ag2/PRA protein. In fact, other than an inference that the cleaved peptide should exist in an impure state in nature, there has been no attention paid to Ag2/PRA N-terminal sequences. In particular, there is no indication in the literature that the N-terminal peptide or underlying DNA could function in vaccinating against *Coccidioides* spp., let alone that such peptides and genetic constructs would be substantially as effective as the full length Ag2/PRA molecule. Signal peptides from viral proteins reported to stimulate cytotoxic T cells (Franco et al., 1993; Kondo et al., 1995) do not have sequence homology to the peptides of the present invention.

In addition to the fundamental discoveries of the present invention, the inventors contemplate that certain refinements will even further improve the peptide and genetic vaccines of the invention. For example, in light of the present disclosure, it is now within the skill of the ordinary artisan to refine and optimize various aspects, such as peptides, vectors, doses, combinations, vaccination routes, adjuvant formulations and the like, to produce even more effective vaccine compositions and methods in accordance with the present invention.

Although various adjuvants are appropriate for use with the present invention, the use of certain selected adjuvants may provide particular advantages in certain embodiments, as will be known those of ordinary skill in the art. For example, selected adjuvants for use in the delivery of the signal sequences of the invention include the biodegradable and biocompatible polyester poly(lactide-co-glycolide) (PLG) formulated as microparticles. Such microparticles have been used in humans for many years as suture material and as controlled-release delivery systems (Putney and Burke, 1998), and more recently as adjuvants (Maloy et al., 1994; specifically incorporated herein by reference). The Ag2/PRA-derived synthetic or recombinant peptides and associated genetic constructs of the invention are highly suitable for incorporation into such PLG microparticles in order to provide enhanced protection upon vaccination.

Further modifications contemplated to be useful with the Ag2/PRA(1–18) signal sequence peptides and genetic constructs include various combinations and forms of the signal sequence, particular modifications within the sequence, variations in recombinant production and adaptation of the synthetic constructs. All such aspects can now be practiced in light of the guidance provided herein and the knowledge of those of ordinary skill in the art.

An important aspect of the protective capacity of the Ag2/PRA(1–18) constructs is attributable to their ability to elicit cytotoxic CD8+ T lymphocytes. This process involves the recognition of MHC class I molecules by intracellularly processed peptides targeted to the endoplasmic reticulum by the host cell machinery. To further facilitate the processes of MHC class I recognition and the formation of Class I-peptide complexes, the Ag2/PRA(1–18) peptide sequence (or underlying DNA) is modified to contain one or more endoplasmic reticulum insertion sequences, such as those derived from an adenovirus glycoprotein (Restifo et al., 1995; specifically incorporated herein by reference).

Another effective strategy involves the construction of a so-called "multiple antigen peptide (MAP)" construct containing various branches of the Ag2/PRA(1–18) peptides and polypeptides, whether recombinant or synthetic, linked to a core structure. For example, typical MAP constructs include four or more branches of synthetic or recombinant Ag2/PRA(1–18) linked to a lysine-glycine core (Franke et al., 2000; specifically incorporated herein by reference). Such epitope-based vaccines are delivered in adjuvants to further enhance their protective efficacy and the induction of cytotoxic T cells.

Yet further aspects of the present invention involve the use of smaller peptides from the N-terminal 18 amino acids, and associated expression constructs, which peptides nonetheless contain one or more protective epitopes. The identification of protective epitopes from within this region is routine now that the 18 amino acids have been surprisingly distinguished from the 194 of the entire Ag2/PRA protein.

By way of example only, one may wish to use shorter peptides, such as those of about 17, 16, 15, 14, 13, 12 and the like amino acids in length. Although a range of amino acid deletions and substitutions can be made and still obtain a bioactive peptide within the scope of the present invention, it may be convenient to delete amino acids from towards the C-terminal of the peptide of SEQ ID NO:2. Other suitable examples are substantially shorter comprising the Class I epitope at residues 2 through 10 of SEQ ID NO:2 (QFSHALIAL). Such peptides may be about 9 amino acids in length.

Peptides of less than about 9 amino acids in length may also be used in the present invention, so long as they contain sufficient sequence information to provide a measurable benefit in one or more useful embodiments, such as in T cell binding, and particularly, in the protection against *Coccidioides* spp. infections. The peptides may thus be of any minimum, functional length, such as, e.g., about 4, 5, 6, 7, 8 or 9 amino acids in length.

In terms of amino acid substitutions, a wide range of substitutions is tolerated within the peptides of the invention. As detailed herein, the ability to make and test variants, e.g., using site-directed mutagenesis, is now routine in the art and is performed without undue experimentation once a useful, parent sequence has been provided, as in the present invention. In choosing such variants and substitution, it may be convenient not to modify, or at least not to extensively modify the Class I epitope of QFSHALIAL (residues 2 through 10 of SEQ ID NO:2).

It will be understood that there is no requirement for any truncated or variant sequences of the invention to function to essentially the same degree of effectiveness as the native 18-mer sequence. It will rather be realized that certain other benefits may be worthwhile tolerating a degree of reduction of function in certain assays. Such features include, e.g. increased bioavailability, cross-reactivity and such like. The ease and even cost of production may also favor using shorter or variant peptides or constructs, even if their vaccination profile is somewhat reduced in some aspects from the N-terminal 18-mers. However, variant peptides that function to essentially the same degree as the N-terminal 18-mer peptide of SEQ ID NO:2 will be preferred for use in the present invention. Peptides that are at least about as effective in vaccination as the N-terminal 18-mer peptide of SEQ ID NO:2 will be particularly preferred, and peptides and derivatives that have increased biological effectiveness in comparison to the peptide of SEQ ID NO:2 are also encompassed within the invention.

Any of the peptide sequences of the invention, whether substantially full length (approximately 18-mers), truncated and/or comprising variant sequences, may be combined with one or more other sequences, either for ease of production and purification, or with an intended therapeutic benefit. Accordingly, the overall length of the peptides for use in the invention may be about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 amino acids, upwards to and including polypeptides and proteins of about 60, 70, 80, 90, 100, 110, 120, 130, 140, 150, 160, 170, 180, 190, 200, 210, 220, 230, 240, 250, 300, 350, 400, 450, 500, 550, 600, 650, 700, 800, 900 and about 1,000 amino acids in length and the like.

Although the N-terminal 18 amino acid peptides and associated expression constructs of the present invention are desirably small in size, the length of the peptides may be increased without any recognizable and/or significant reduction in the attendant advantages, such as ease of preparation and use, cost, bioavailability and such like. Accordingly, longer peptides that contain the first N-terminal 18 amino acids and extend to 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so amino acids of SEQ ID NO:4 (as may be encoded by the corresponding codons of SEQ ID NO:3) may also be used. So long as the inclusion of the additional amino acid sequences does not impair the function of the signal peptide sequence of the primary discovery, the use of such longer sequences is included within the present invention.

The use of longer peptides within the invention extends to the preparation and use of polypeptides and proteins, and their underlying DNA constructs, in which the coding (gene) sequence between Ag2/PRA(1–18) and Ag2/PRA(19–194) is modified, deleted or inactivated in a manner that blocks the cleavage site between these two domains and, in doing so, results in the expression of the full-length Ag2/PRA (1–194) recombinant antigen (or cDNA). In such embodiments, expression of the modified construct, either in vitro or in vivo, results in the full-length Ag2/PRA(1–194) recombinant antigen from which the important 18 N-terminal amino acids cannot be readily cleaved.

IV. Peptides, Proteins and Nucleic Acids

The present invention thus provides a range of purified, and in preferred embodiments, substantially purified, peptides with sequences generally based upon the N-terminal sequence of the Ag2/PRA protein. Succinctly, these peptides of the invention are termed "*Coccidioides* spp. peptides".

The term "purified *Coccidioides* spp. peptide" as used herein, refers to a *Coccidioides* spp. peptide composition of the invention, isolatable, e.g., from *C. immitis* or *C. posadasii*, recombinant host cells and/or Ag2/PRA, wherein the peptide is purified to any degree relative to its naturally-obtainable state, i.e., relative to its purity within a cellular extract in which the cleaved peptide may be expected to be present. A purified *Coccidioides* spp. peptide therefore also refers to a *Coccidioides* spp. peptide free from the environment in which it naturally occurs.

The *Coccidioides* spp. peptide may be "original full length", such as being about 18 amino acids in length. The *Coccidioides* spp. peptides may also be less then full length, such as individual subregions or epitopic peptides, as described herein. Where less than full length peptides are concerned, certain preferred examples will be those containing predicted immunogenic sites such as and those containing epitopes that induce cell-mediated immune responses and the like.

Generally, "purified" will refer to a *Coccidioides* spp. peptide composition that has been subjected to fractionation to remove various non-*Coccidioides* spp. peptide components, including the full length Ag2/PRA protein, and which composition substantially retains its *Coccidioides* spp. peptide status, as may be readily assessed by binding to antibodies, or preferably T cells, reactive with the native *Coccidioides* spp. peptide, providing protection against challenge and such like.

Where the term "substantially purified" is used, this will refer to a composition in which the *Coccidioides* spp. peptides of the invention form the major component of the composition, such as constituting about 50% of the peptides in the composition or more. In preferred embodiments, a substantially purified protein will constitute more than 60%, 70%, 80%, 90%, 95%, 96%, 97%, 98% or 99% or so of the peptides in the composition. However, this does not exclude the re-mixing of the peptides of the invention, once purified, with other vaccine components.

A *Coccidioides* spp. peptide that is "purified to homogeneity," as applied to the present invention, means that the *Coccidioides* spp. peptide has a level of purity where the *Coccidioides* spp. peptide is substantially free from other proteins, peptides and biological components. For example, a purified *Coccidioides* spp. peptide will often be sufficiently free of other peptide and protein components so that degradative sequencing may be performed successfully.

To purify a *Coccidioides* spp. peptide, a natural or recombinant composition comprising at least some *Coccidioides* spp. peptides will be subjected to fractionation to remove various non-*Coccidioides* spp. peptide components from the composition. Various techniques suitable for use in peptide purification are well known to those of skill in the art and can be sued herein.

Certain specific examples are the purification of *Coccidioides* spp. peptide fusion proteins using specific binding partners. Such purification methods are routine in the art. As the present invention provides DNA sequences for *Coccidioides* spp. peptides, any fusion protein purification method can now be practiced. This is exemplified by the generation of *Coccidioides* spp. peptides and Ag2/PRA-glutathione S-transferase fusion proteins, expression in *E. coli*, and isolation using affinity chromatography on glutathione-agarose. His-tagged *Coccidioides* spp. peptides and proteins are particularly provided herein.

Although preferred for use in certain embodiments, there is no general requirement that the *Coccidioides* spp. peptide always be provided in its most purified state. Indeed, it is contemplated that less substantially purified *Coccidioides* spp. peptides, which are nonetheless enriched in *Coccidioides* spp. peptide compositions, relative to the natural state, will have utility in certain embodiments. Methods exhibiting a lower degree of relative purification may have advantages in total recovery of peptide product, or in maintaining the activity of expressed peptides. Even inactive products have utility in certain embodiments, particularly in antibody generation.

Further important aspects of the present invention concern isolated nucleic acid segments and recombinant vectors encoding the *Coccidioides* spp. peptides, including wild-type, polymorphic, mutant and second generation peptides, and the creation and use of recombinant host cells through the application of DNA technology, that express any such *Coccidioides* spp. peptide. The nucleic acid segments are generally isolated free from total genomic DNA, and more preferably free from total or unmodified Ag2/PRA DNA, and are capable of expressing a *Coccidioides* spp. peptide or sub-peptide.

Although the following discussion of nucleic acid segments is generally applicable to various nucleic acid segments encoding longer polypeptides, proteins, fusion proteins and co-expression vectors, the preferred nucleic acid segments of the invention are generally short and encode and express *Coccidioides* spp. peptides or sub-peptides of relatively small length. The currently most preferably nucleic acid segments of the invention are those that encode the peptide of SEQ ID NO:2.

As used herein, the terms "nucleic acid segment" and "DNA segment" refer to nucleic acid and DNA molecules that have been isolated free from total genomic nucleic acids or DNA of a particular species, such as *C. immitis*. Preferably, nucleic acid segments of the invention are also free from total or unmodified *Coccidioides* spp. Ag2/PRA DNA. Therefore, a DNA segment encoding a *Coccidioides* spp. peptide refers to a DNA segment that contains wild-type, polymorphic, variant or mutant *Coccidioides* spp. peptide coding sequences isolated away from, or purified free from, total *Coccidioides* spp. genomic nucleic acids or DNA, and preferably, free from total or unmodified Ag2/PRA DNA. Included within the terms "nucleic acid and DNA segment", are nucleic acids and DNA segments and smaller fragments of such segments, and also recombinant vectors, including, for example, plasmids, cosmids, phage, viruses, and the like.

A nucleic acid or DNA segment comprising an isolated or purified wild-type, polymorphic, variant or mutant *Coccidioides* spp. peptide gene refers to a nucleic acid or DNA segment including coding sequences and, in certain aspects, regulatory sequences, isolated substantially away from other naturally occurring genes or protein encoding sequences, notably the Ag2/PRA DNA. In this respect, the term "gene" is used for simplicity to refer to a functional peptide encoding unit. As will be understood by those in the art, this functional term preferably refers to cDNA sequences and smaller engineered gene segments that express, or may be adapted to express, peptides, polypeptides, domains, fusion proteins and mutants.

"Isolated substantially away from other coding sequences" means that the *Coccidioides* spp. peptide-encoding nucleic acid or DNA segment forms the significant part of the coding region, and that the overall nucleic acid segment does not contain large portions of naturally-occurring nucleic acids or DNA, such as large chromosomal fragments or other functional genes or cDNA coding regions, notably the Ag2/PRA DNA. Of course, this refers to the nucleic acid or DNA segment as isolated, and does not exclude genes or coding regions later added to the segment by the hand of man.

In particular embodiments, the invention concerns isolated nucleic acid and DNA segments and recombinant vectors incorporating nucleic acid sequences that encode a *Coccidioides* spp. peptide, and the peptides themselves, that include a contiguous amino acid sequence of at least about 7 or 8 amino acids from SEQ ID NO:2. In other particular embodiments, the invention concerns isolated nucleic acid and DNA segments and recombinant vectors that encode a *Coccidioides* spp. peptide, and the peptides themselves, that include within their amino acid sequences the substantially full length peptide sequence of SEQ ID NO:2 or the full length peptide of SEQ ID NO:2.

In other embodiments, the invention concerns isolated nucleic acid and DNA segments and recombinant vectors incorporating DNA sequences that encode a *Coccidioides* spp. peptide, and the peptides themselves, that include an amino acid sequence essentially as set forth in SEQ ID NO:2 or an amino acid sequence essentially as set forth in a longer sequence starting with SEQ ID NO:2 and extending through additional amino acid sequences of SEQ ID NO:4. The term "a sequence essentially as set forth in" means that the sequence substantially corresponds to a portion of the defined sequence, such as SEQ ID NO:2, or the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so amino acids of SEQ ID NO:4, and has relatively few amino acids that are not identical to, or a biologically functional equivalent of, the amino acids of the reference SEQ ID NO.

In terms of SEQ ID NO:2 and sequences that are in their entirety, or that include a sequence that is essentially as set forth in SEQ ID NO:2, the % identity and functional equivalency is calculated according to the number of non-identical and/or non-equivalent amino acids. For example, sequences that have, or include a region that has, 17 amino acids that are identical or equivalent to the amino acids of SEQ ID NO:2 are said to be at least about 94% identical or equivalent for the purposes of the present disclosure. This includes sequences and sequence regions that are 18 amino acids in length and include one non-identical or non-equivalent amino acid, as well as sequences and sequence regions that are 17 amino acids in length and that lack an amino acid from SEQ ID NO:2.

Similarly, whether shorter or the same length, sequences that have, or include a region that has, 16 amino acids that are identical or equivalent to the amino acids of SEQ ID NO:2 are said to be at least about 88% identical or equivalent; sequences that have, or include a region that has, 15 amino acids that are identical or equivalent to the amino acids of SEQ ID NO:2 are said to be at least about 83% identical or equivalent; sequences that have, or include a region that has, 14 amino acids that are identical or equivalent to the amino acids of SEQ ID NO:2 are said to be at least about 77% identical or equivalent for the purposes of the present disclosure; and such like.

As the present invention includes isolated nucleic acid and DNA segments and recombinant vectors incorporating DNA sequences that encode a *Coccidioides* spp. peptide, and the peptides themselves, that include an amino acid sequence essentially as set forth in the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so amino acids of SEQ ID NO:4, the term "biologically functional equivalent" is applicable to amino acid sequences that are between about 70% and about 80%; or more preferably, between about 81% and about 89%; or more preferably, between about 90% and about 94% or between about 95% and about 99% of amino acids that are identical or functionally equivalent to the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so amino acids of SEQ ID NO:4. Sequences of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or about 99% sequence identity or functionally equivalency are encompassed in the invention.

In certain other embodiments, the invention concerns isolated DNA segments and recombinant vectors that include within their sequence a nucleic acid sequence essentially as set forth in SEQ ID NO:1 or a nucleic acid sequence essentially as set forth in the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so codons of SEQ ID NO:3. The term "essentially as set forth in SEQ ID NO:1 or SEQ ID NO:3" is used in the same sense as described above and means that the nucleic acid sequence substantially corresponds to a portion of SEQ ID NO:1 or SEQ ID NO:3 and has relatively few codons that are not identical, or functionally equivalent, to the codons of SEQ ID NO:1 or SEQ ID NO:3. The term "functionally equivalent codon" is used herein to refer to codons that encode the same amino acid, such as the six codons for arginine or serine, and also refers to codons that encode biologically equivalent amino acids (see Table A).

The same considerations apply to isolated DNA segments and recombinant vectors that include within their sequence a nucleic acid sequence essentially as set forth in SEQ ID NO:1 or a nucleic acid sequence essentially as set forth in the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so codons of SEQ ID NO:3. The term "essentially as set forth in SEQ ID NO:1 or SEQ ID NO:3" is used in the same sense as described above and means that the nucleic acid sequence substantially corresponds to a portion of SEQ ID NO:1 or SEQ ID NO:3 and has relatively few codons that are not identical, or functionally equivalent, to the codons of SEQ ID NO:1 or SEQ ID NO:3.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of structural and/or functional biological activity, where protein expression is concerned. The addition of terminal sequences as applied to nucleic acid sequences includes, for example, the addition of various regulatory or other non-coding or coding sequences flanking either of the 5' or 3' portions of the coding region.

In terms of SEQ ID NO:1, the % identity and functional equivalency is calculated according to the number of non-identical and/or non-equivalent codons, such that sequences that have, or include a region that has, 17 codons that are identical or equivalent to the codons of SEQ ID NO:1 are said to be at least about 94% identical or equivalent for the purposes of the present disclosure. Therefore, sequences that are, or include a region that is, at least about 77%, at least about 83% or at least about 88% identical or equivalent to the sequence of SEQ ID NO:1 are preferred in certain embodiments.

As to SEQ ID NO:3, DNA sequences that encode peptides that include an amino acid sequence essentially as encoded by the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so codons of SEQ ID NO:3, the term "biologically functional equivalent" is applicable to sequences that are between about 70% and about 80%; or more preferably, between about 81% and about 89%; or more preferably, between about 90% and about 94% or between about 95% and about 99% identical or functionally equivalent to the first 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110 or so codons of SEQ ID NO:3. Sequences of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99% sequence identity or functionally equivalency are encompassed in the invention.

Sequences that are essentially the same as those set forth in SEQ ID NO:1 or the first sections of SEQ ID NO:3 may also be functionally defined as sequences that are capable of hybridizing to a nucleic acid segment of SEQ ID NO:1 or SEQ ID NO:3 (or containing the complement of SEQ ID NO:1 or SEQ ID NO:3) under appropriately stringent conditions. Suitable appropriately or relatively stringent hybridization conditions will be well known to those of skill in the art and are further exemplified herein.

Naturally, the present invention also encompasses DNA segments that are complementary, or essentially complementary, to the sequence set forth in SEQ ID NO:1 or the first sections of SEQ ID NO:3. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3 under relatively stringent conditions such as those described herein.

The nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment or fragment of almost any length may be employed, with the total length preferably being limited by the ease of preparation and use in the intended recombinant protocol.

For example, nucleic acid segments or fragments may be prepared that include a short contiguous stretch identical to or complementary to SEQ ID NO:1, such as about a 15, 18 or 21 nucleotide stretch, up to about 20,000, about 10,000, about 5,000 or about 3,000 base pairs in length. Nucleic acid and DNA segments with total lengths of about 1,000, about 500, about 200, about 100 and about 0.50 base pairs in length (including all intermediate lengths) are also contemplated to be useful.

It will be readily understood that "intermediate lengths", in these contexts, means any length between the quoted ranges, such as 21, 22, 23, 24, 25, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,001, 20,001 and the like.

It will also be understood that this invention is not limited to the particular nucleic acid and amino acid sequences of SEQ ID NO:1 and SEQ ID NO:2. Recombinant vectors and isolated DNA segments may therefore variously include the coding region from SEQ ID NO:1, coding regions bearing selected alterations or modifications in the basic coding region, or they may encode larger polypeptides that nevertheless include such coding regions or may encode biologically functional equivalent proteins or peptides that have variant amino acids sequences.

The nucleic acid and DNA segments of the present invention encompass biologically functional equivalent *Coccidioides* spp. peptides that arise as a consequence of codon redundancy and functional equivalency that are known to occur naturally within nucleic acid sequences and the proteins thus encoded. Equally, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein.

One may also prepare fusion proteins and peptides, e.g., where the *Coccidioides* spp. peptide coding region is aligned within the same expression unit with other proteins or peptides having desired functions, such as for purification or immunodetection purposes (e.g., proteins that may be purified by affinity chromatography and enzyme label coding regions, respectively).

V. Epitopes

Even smaller peptides corresponding to one or more T cell or antigenic determinants, or "epitopic core regions", of the *Coccidioides* spp. peptides can also be prepared. Exemplary peptides include those comprising epitopes that induce cell-mediated immune responses, as disclosed herein. Such peptides should generally be at least five or six amino acid residues in length, and will preferably be about 8, 10, 12 or 15 or so amino acid residues in length.

Synthetic peptides will generally be a maximum of about 35, 36, 37, 38, 39, 40, 41, 42, 43, 44 or 45 residues long or so, which is the approximate upper length limit of automated peptide synthesis machines, such as those available from Applied Biosystems (Foster City, Calif.). Longer peptides may also be prepared, e.g., by recombinant means. Recombinant peptides of any desired length may be used.

U.S. Pat. No. 4,554,101 (Hopp), incorporated herein by reference, teaches the identification and preparation of epitopes from primary amino acid sequences on the basis of hydrophilicity. Although prediction of epitopes that induce cell-mediated immune responses is most important to the present invention, through the methods disclosed in U.S. Pat. No. 4,554,101, one of skill in the art is able to identify general epitopes from within an amino acid sequence such as those of SEQ ID NO:2, or longer sequences from SEQ ID NO:4. Numerous scientific publications have also been devoted to the prediction of secondary structure, and to the identification of epitopes, from analyses of amino acid sequences (Chou & Fasman, 1974a,b; 1978a,b, 1979; each incorporated herein by reference). Any of these may be used, if desired, to supplement the teachings of U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1998; Wolf et al., 1988; each incorporated herein by reference), the program PepPlot® (Brutlag et al., 1990; Weinberger et al., 1985; each incorporated herein by reference), and other new programs for protein tertiary structure prediction (Fetrow & Bryant, 1993; incorporated herein by reference). Further commercially available software capable of carrying out such analyses is termed MacVector (IBI, New Haven, Conn.).

In further embodiments, major antigenic determinants of a polypeptide may be identified by an empirical approach in which portions of the cDNA (gene) encoding the polypeptide are expressed in a recombinant host, and the resulting proteins tested for their ability to elicit an immune response. For example, PCR™ can be used to prepare a range of peptides lacking successively longer fragments of, e.g., the C-terminus of the peptides of the invention. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined. The same approach is applied to substitutions. As the peptides of the present invention are relatively small at origin, similar analyses may also be conducted using synthetic peptides.

Another method for determining the major antigenic determinants of a polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. The antigenic determinants of the peptides that are initially identified can be further localized by performing subsequent syntheses of smaller peptides with larger overlaps, and by eventually replacing individual amino acids at each position along the immunoreactive peptide.

In terms of T cell epitopes, immunogenic portions may be identified using computer analysis, such as the Tsites program (Rothbard and Taylor, 1988; Deavin et al., 1996, each specifically incorporated herein by reference), which searches for peptide motifs that have the potential to elicit Th responses. Peptides with motifs appropriate for binding to murine and human class I or class II MHC may be identified according to BIMAS (Parker et al., 1994, specifically incorporated herein by reference) and other HLA peptide binding prediction analyses. To confirm immunogenicity, peptides may, if desired, be tested using an HLA binding assays, including a transgenic mouse model and/or in in vitro binding and stimulation assays.

Once one or more such analyses are completed, peptides are prepared that contain at least the essential features of one or more antigenic and/or sequence determinants that induce cell-mediated immune responses. The peptides are then employed in the generation of protective immune responses. Minigenes or gene fusions encoding these determinants can also be constructed and inserted into expression vectors by standard methods, for example, using PCR™ cloning methodology.

The use of particularly small peptides for vaccination can benefit from conjugation of the peptide to an immunogenic carrier protein, such as hepatitis B surface antigen, keyhole limpet hemocyanin or bovine serum albumin. Methods for performing this conjugation are well known in the art.

Modifications and changes may also be made in the structure of the *Coccidioides* spp. peptides and nucleic acids of the present invention, and still obtain molecules having like or otherwise desirable characteristics. Such is the meaning of "biologically functional equivalents" of the peptides of the present invention.

For example, certain amino acids may be substituted for other amino acids in a peptide structure without appreciable loss of interactive binding capacity, for example, peptide signal capacity, epitopes, immunoprotection and the like. Since it is the interactive capacity and nature of a peptide that defines that peptide's biological functional activity, certain amino acid sequence substitutions can be made in a peptide sequence (or, of course, its underlying DNA coding sequence) and nevertheless obtain a peptide with like (agonistic) properties. It is thus contemplated that various changes may be made in the sequence of the *Coccidioides* spp. peptides, or underlying DNA, without appreciable loss of their biological utility or activity.

In terms of functional equivalents, it is well understood by the skilled artisan that, inherent in the definition of a "biologically functional equivalent peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acid substitutions should be made within the given peptide. Longer peptides may have an intermediate number of changes. Of course, a plurality of distinct peptides with different substitutions may easily be made and used in accordance with the invention.

It is also well understood that where certain residues are shown to be particularly important to the biological or structural properties of a protein or peptide, such residues may not generally be exchanged. Particular examples are epitopes that induce cell-mediated immune responses, signal peptide sequences, sequences that target the ER and such like. Maintenance of biological structure/function can always be easily tested though. For example, functional equivalents may be defined as those peptides that maintain a substantial ability to function like the native peptides of SEQ ID NO:2.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein or peptide is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent peptide thereby created is intended for use in immunological embodiments, as in the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent peptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments (Table A), as well as for other uses, such as in the design of probes and primers and the like.

TABLE A

DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

Site-specific mutagenesis is a technique useful in the preparation of individual peptides, or biologically functional equivalent peptides, through specific mutagenesis of the underlying DNA. The technique further provides a ready ability to prepare and test sequence variants by introducing one or more nucleotide sequence changes into the DNA. U.S. Pat. No. 4,888,286 is specifically incorporated herein by reference to further exemplify such processes.

Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Techniques of site-specific mutagenesis are well known in the art. Certain techniques typically employ a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the Coccidioides spp. peptides using site-directed mutagenesis described above is provided as a means of producing potentially useful species and is not meant to be limiting, as there are other ways in which sequence variants of Coccidioides spp. peptides may be obtained. For example, recombinant vectors encoding the desired gene may be treated with mutagenic agents, such as hydroxylamine, to obtain sequence variants.

Although the foregoing methods are suitable for use in mutagenesis, the use of PCR™ is generally now preferred. This technology offers a quick and efficient method for introducing desired mutations into a given DNA sequence. The following text particularly describes the use of PCR™ to introduce point mutations into a sequence, as may be used to chance the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows:

denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

One effective method of confirming that a functionally equivalent peptide has retained sufficient *Coccidioides* spp. peptide characteristics is to confirm that the equivalent peptide is immunologically cross-reactive with the *Coccidioides* spp. peptide. Tests of immunological cross-reactivity are a straightforward matter and can be readily determined using specific assays, i.e., based upon competition for binding sites. In the present invention, assays involving T cells may be particularly suitable. A valuable test of biological activity in accordance with the present invention is the maintenance of significant or substantial immunoprotective capacity, which can be readily tested by those of ordinary skill in the art according to the present disclosure.

In addition to the *Coccidioides* spp. peptidyl compounds described herein, other sterically similar compounds may be formulated to mimic the key portions of the peptide structure, e.g., to also function in immunoprotection. Such compounds, which may be termed peptidomimetics, may be used in the same manner as the peptides of the invention and hence are also functional equivalents.

The underlying rationale behind the use of peptide mimetics is that the peptide backbone exists chiefly to orientate amino acid side chains in such a way as to facilitate molecular interactions, such as those of antigens and T cells. A peptide mimetic is thus designed to permit molecular interactions similar to the natural molecule.

Some successful applications of the peptide mimetic concept have focused on mimetics of β-turns within proteins, which are known to be highly antigenic (Johnson et al., 1993). Likely β-turn structure within a polypeptide can be predicted by computer-based algorithms, as known those of ordinary skill in the art. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of modeling is now well known, and by such methods chemical variants of *Coccidioides* spp. peptides can be designed and synthesized. It will be understood that all such sterically designed constructs fall within the scope of the present invention.

VI. Pharmaceutical Compositions

The *Coccidioides* spp. peptide and/or nucleic acid compositions, vaccines, or cocktails thereof are formulated into pharmaceutical compositions for administration. The most basic pharmaceutical compositions of the present invention will generally comprise an effective amount of at least a first *Coccidioides* spp. peptide and/or nucleic acid, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

A. Injectable Formulations

The *Coccidioides* spp. peptide and/or nucleic acid constructs of the present invention may be formulated for parenteral administration, e.g., formulated for injection via the intravenous, intramuscular, sub-cutaneous, transdermal, or other such routes, including direct instillation into the lungs. The preparation of an aqueous composition that contains such a *Coccidioides* spp. peptide and/or nucleic acid as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The *Coccidioides* spp. peptide and/or nucleic acid compositions can be formulated into a sterile aqueous composition in a neutral or salt form. Solutions of the *Coccidioides* spp. peptide and/or nucleic acids as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the *Coccidioides* spp. peptide and/or nucleic acid constructs should be extensively dialyzed to remove undesired small molecular weight molecules, and/or lyophilized for more ready formulation into a desired vehicle, where appropriate. Sterile injectable solutions are prepared by incorporating the active *Coccidioides* spp. peptide and/or nucleic acid agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the *Coccidioides* spp. peptide and/or nucleic acid construct admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards. Upon formulation, the *Coccidioides* spp. peptide and/or nucleic acid solutions will be administered in a manner compatible with the dosage formulation and in such amount as is therapeutically effective.

B. Sustained Release Formulations

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver the *Coccidioides* spp. peptide and/or nucleic acid constructs in accordance with the present invention.

Pharmaceutical "slow release" capsules or "sustained release" compositions or preparations may also be used. Slow release formulations are generally designed to give a constant drug level over an extended period and may be used to deliver *Coccidioides* spp. peptide and/or nucleic acid construct in accordance with the present invention. The slow release formulations are typically implanted in the vicinity of the disease site, for example, the lungs.

Suitable examples of sustained-release preparations include semipermeable matrices of solid hydrophobic polymers containing the *Coccidioides* spp. peptide and/or nucleic acid construct, which matrices are in the form of shaped articles, e.g., films or microcapsule. Examples of sustained-release matrices include polyesters; hydrogels, for example, poly(2-hydroxyethyl-methacrylate) or poly (vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot™

(injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

C. Liposomes and Nanocapsules

In certain embodiments, liposomes and/or nanoparticles may also be employed with the *Coccidioides* spp. peptide and/or nucleic acid constructs. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

D. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of a *Coccidioides* spp. peptide and/or nucleic acid construct for topical use, such as in creams, ointments and gels, includes the preparation of oleaginous or water-soluble ointment bases, will be well known to those in the art in light of the present disclosure. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

E. Nasal Formulations

Local delivery via the nasal and respiratory routes is particularly contemplated for use in the present invention. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 μm. Fine mists are produced by pressurized aerosols and hence their use in considered advantageous.

VII. Adjuvants

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-actylmuarnyl-L-alanyl-D-isoglutamine [MDP]), a bacterial peptidoglycan. MDP is believed to stimulate macrophages, but also appears to stimulate B cells directly. The effects of adjuvants, therefore, are not antigen-specific. When administered together with a purified antigen, however, they can be used to selectively promote the response to the antigen. Adjuvants have been used experimentally to promote a generalized increase in immunity against unknown antigens (e.g., U.S. Pat. No. 4,877,611).

The present invention contemplates that a variety of adjuvants may be employed, including the RIBI MPL-SE adjuvant. Certain selected adjuvants preferred for use are biodegradable and biocompatible polymers, such as PLG, PLA and PLGA, particularly those formulated as microspheres and microparticles (Maloy et al., 1994; specifically incorporated herein by reference). Certain other useful adjuvants are listed in Table B. This list is not intended to be exhaustive, merely exemplary of the different kinds of adjuvants that can be used in accordance with this invention.

TABLE B

| Exemplary Adjuvants | |
|---|---|
| Alhydrogel | |
| Alkyl Lysophosphilipids (ALP) | |
| Bcg | |
| Bestatin | |
| Biliverdin | including derivatives and glycoconjugates |
| Bilirubin | including derivatives and glycoconjugates, such as monoglycouranoglycans and diglycouranoglycans |
| Biotin | including biotinylated derivatives |
| Carnosine | including derivatives |
| Chitin | |
| Chitosan | deacetylated chitin |
| Cholesteryl Succinate | |

TABLE B-continued

| Exemplary Adjuvants | |
|---|---|
| Cornyebacterium Parvum | whole or part of cell including oligosaccharides and glycolipids |
| C. Granulosum | whole or part of cell including P40 a peptidoglycan with a glycoprotein |
| Monophoshoryl Lipid A | Deacetylated |
| Monophosphoryl Lipid A | Synthetic |
| Isoprinosine | |
| Lithosperman | lithosperman A, lithospemian B or lithosperman C |
| Trehalose Monomycolate | |
| Trehalose Dimycolate | |
| Mycobacterial Species | whole or part of Cell including glycolipids, phenolic glycolipids, peptides such as 45/47 kda and BCG |
| Muramyl Dipeptide | N-acetyl muramyl-L-alanyl-D-isoglutamine |
| Muramyl Tripeptide | MF75.2 |
| Threonyl-Muramyl Dipeptide | |
| Murametide | |
| Murabutide | |
| Lipoteichoic Acid | LTA |
| Ribitol Teichoic Acid | RTA |
| Glycerol Teichoic Acid | GTA |
| Superantigens | S. aureus enterotoxins, S. epidermidis enterotoxins, S. pyogenes enterotoxins, E. coli exotoxins |
| Staphylococcus Species | whole or part of cell including peptidoglycans and enterotoxins |
| Viruses | whole or part of particle including Vaccinia, Newcastle disease visurs, vesicular stomatitis virus, papilloma virus and rhinovirus |
| Synthetic Peptides | pentamers, hexamers, heptamers, octamers, nonamers, decamers, etc.; such as polylysine and threonine-alanine peptides |
| Recombinant Prolactin | |
| Glycosaminoglycans | and lipid and peptide derivatives |
| Glycosaminoglycouranoglycans | |
| Glycosaminoglycolipids | |
| GlycosaminoglycouranoGlycolipids | |
| Glycosaminoglycopeptides | |
| GlycosaminoglycouranoGlycopeptides | |
| Phosphorylated Glycosaminoglycans | |
| Sulphanted Glycosaminoglycan | |
| Qs-21 | |
| Quil-A | |
| Polymethylmethyl Acrylate (PMMA) | |
| Retinoic Acid | |
| Lentinan | |
| Levan | |
| Malic Anhydride-Divinyl Ether (MVE-2) | |
| Hemocyanin | from keyhole limpet (KLH) |
| Hemoerythrin | molluscan, arthropod hemoerythrin from annelids and lower invertebrates |
| Pteridines | |
| Nucleic Acids | preferably poly A, poly T, poly AT, poly GC and poly IC-LC |
| Oligonucleotides | varying kilobases |
| Lentinen | |
| Lectins | part or whole; from plants and animals |

Certain useful adjuvants are the teichoic acids from Gram-ve cells. These include the lipoteichoic acids (LTA), ribitol teichoic acids (RTA) and glycerol teichoic acid (GTA). Active forms of their synthetic counterparts may also be employed in connection with the invention (Takada et al., 1995).

Hemocyanins and hemoerythrins may also be used in the invention. The use of hemocyanin from keyhole limpet (KLH) is preferred, although other molluscan and arthropod hemocyanins and hemoerythrins may be employed.

Various polysaccharide adjuvants may also be used. For example, Yin et al. (1989) describe the use of various pneumococcal polysaccharide adjuvants on the antibody responses of mice. The doses that produce optimal responses, or that otherwise do not produce suppression, as indicated in Yin et al. (1989) should be employed. Polyamine varieties of polysaccharides are preferred, such as chitin and chitosan, including deacetylated chitin.

A further preferred group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645 and PCT Patent Application WO 91/16347, are also proposed for use in the present invention.

BCG and BCG-cell wall skeleton (CWS) may also be used as adjuvants in the invention, with or without trehalose dimycolate. Trehalose dimycolate may be used itself. Azuma et al. (1988) show that trehalose dimycolate administration correlates with augmented resistance to influenza virus infection in mice. Trehalose dimycolate may be prepared as described in U.S. Pat. No. 4,579,945.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides, as described by Yamamoto et al. (1988) are another useful group of adjuvants. Quil A and lentinen are further suitable adjuvants.

Superantigens are also contemplated for use as adjuvants in the present invention. "Superantigens" are generally bacterial products that stimulate a greater proportion of T lymphocytes than peptide antigens without a requirement for antigen processing (Mooney et al., 1994). Superantigens include *Staphylococcus* exoproteins, such as the alpha, beta, gamma and delta enterotoxins from *S. aureus* and *S. epidermidis*, and the alpha, beta, gamma and delta *E. coli* exotoxins.

Common *Staphylococcus* enterotoxins are known as staphylococcal enterotoxin A (SEA) and staphylococcal enterotoxin B (SEB), with enterotoxins through E (SEE) being described (Rott et. al., 1992). *Streptococcus pyogenes* B (SEB), *Clostridium perfringens* enterotoxin (Bowness et. al., 1992), cytoplasmic membrane-associated protein (CAP) from *S. pyogenes* (Sato et. al., 1994) and toxic shock syndrome toxin-1 (TSST-1) from *S. aureus* (Schwab et. al., 1993) are further useful superantigens.

Another group of adjuvants for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

MPL is another immunopotentiating agent for use herein. References that concern the uses of MPL include Tomai et al. (1987), Chen et al. (1991) and Garg & Subbarao (1992), that each concern certain roles of MPL in the reactions of aging mice; Elliott et al. (1991), that concerns the D-galactosamine loaded mouse and its enhanced sensitivity to lipopolysaccharide and MPL; Chase et al. (1986), that relates to bacterial infections; and Masihi et al. (1988), that describes the effects of MPL and endotoxin on resistance of mice to *Toxoplasma gondii*. Fitzgerald (1991) also reported on the use of MPL to up-regulate the immunogenicty of a syphilis vaccine and to confer significant protection against challenge infection in rabbits.

Thus, MPL is known to be safe for use, as shown in the above model systems. Phase I clinical trials have also shown MPL to be safe for use (Vosika et al., 1984). Indeed, 100 $\mu g/m^2$ is known to be safe for human use, even on an outpatient basis (Vosika et al., 1984).

MPL generally induces polyclonal B cell activation (Baker et al., 1994), and has been shown to augment antibody production in many systems, for example, in immunologically immature mice (Baker et al., 1988a; 1988b); in aging mice (Tomai & Johnson, 1989); and in nude and Xid mice (Madonna & Vogel, 1986; Myers et al., 1995). Antibody production has been shown against erythrocytes (Hraba et al., 1993); T cell dependent and independent antigens; Pnu-immune vaccine (Garg & Subbarao, 1992); isolated tumor-associated antigens (U.S. Pat. No. 4,877,611); against syngeneic tumor cells (Livingston et al., 1985; Ravindranath et al., 1994a;b); and against tumor-associated gangliosides (Ravindranath et al., 1994a;b).

Another useful attribute of MPL is that is augments IgM responses, as shown by Baker et al. (1988a), who describe the ability of MPL to increase antibody responses in young mice. This is a useful feature of an adjuvant for use in certain embodiments of the present invention. Myers et al. (1995) recently reported on the ability of MPL to induce IgM antibodies, by virtue T-cell-independent antibody production. In the Myers et al. (1995) studies, MPL was conjugated to the hapten, TNP. MPL was proposed for use as a carrier for other haptens, such as peptides.

MPL also activates and recruits macrophages (Verma et al., 1992). Tomai and Johnson (1989) showed that MPL-stimulated T cells enhance IL-1 secretion by macrophages. MPL is also known to activate superoxide production, lysozyme activity, phagocytosis, and killing of Candida in murine peritoneal macrophages (Chen et al., 1991).

The effects of MPL on T cells include the endogenous production of cytotoxic factors, such as TNF, in serum of BCG-primed mice by MPL (Bennett et al., 1988). Kovach et al. (1990) and Elliott et al. (1991) also show that MPL induces TNF activity. MPL is known to act with TNF-α to induce release of IFN-γ by NK cells. IFN-γ production by T cells in response to MPL was also documented by Tomai & Johnson (1989) and Odean et al. (1990).

MPL is also known to be a potent T cell adjuvant. For example, MPL stimulates proliferation of melanoma-antigen specific CTLs (Mitchell et al., 1988, 1993). Further, Baker et al. (1988b) showed that nontoxic MPL inactivated suppressor T cell activity. Naturally, in the physiological environment, the inactivation of T suppressor cells allows for increased benefit for the animal. Johnson & Tomai (1988) have reported on the possible cellular and molecular mediators of the adjuvant action of MPL.

MPL is also known to induce aggregation of platelets and to phosphorylate a platelet protein prior to induction of serotonin secretion (Grabarek et al., 1990). This study shows that MPL is involved in protein kinase C activation and signal transduction.

Many articles concern the structure and function of MPL include. These include Johnson et al. (1990), that describes the structural characterization of MPL homologs obtained from *Salmonella minnesota* Re595 lipopolysaccharide. The work of Johnson et al. (1990), in common with Grabarek et al. (1990), shows that the fatty acid moieties of MPL can vary, even in commercial species. In separating MPL into eight fractions by thin layer chromatography, Johnson et al. (1990) found that three were particularly active, as assessed using human platelet responses. The chemical components of the various MPL species were characterized by Johnson et al. (1990).

Baker et al. (1992) further analyzed the structural features that influence the ability of lipid A and its analogs to abolish expression of suppressor T cell activity. They reported that decreasing the number of phosphate groups in lipid A from two to one, i.e., creating monophosphoryl lipid A, MPL, as well as decreasing the fatty acyl content, primarily by removing the residue at the 3 position, resulted in a progressive reduction in toxicity. However, these structural modifications did not influence its ability to abolish the expression of Ts function (Baker et al., 1992). These types of MPL may be used in the present invention.

Baker et al. (1992) also showed that reducing the fatty acyl content from five to four (lipid A precursor $IV_A$ or $I_a$) eliminated the capacity to influence Ts function but not to induce polyclonal activation of B cells. These studies show that in order to be able to abolish the expression of Ts function, lipid A should be a glucosamine disaccharide; may have either one or two phosphate groups; and should have at least five fatty acyl groups. In addition, the chain length of the nonhydroxylated fatty acid, as well as the location of acyloxyacyl groups (2' versus 3' position), may play an important role (Baker et al., 1992).

In examining the relationship between chain length and position of fatty acyl groups on the ability of lipid A to abolish the expression of suppressor T-cell (Ts) activity, Bakker et al. (1994) found that fatty acyl chain lengths of $C_{12}$ to $C_{14}$ appeared to be optimal for bioactivity. Therefore, although their use is still possible, lipid A preparations with fatty acyl groups of relatively short chain length ($C_{10}$ to $C_{12}$ from *Pseudomonas aeruginosa* and *Chromobacterium violaceum*) or predominantly long chain length ($C_{18}$ from *Helicobacter pylori*) are less preferred for use in this invention.

Baker et al. (1994) also showed that the lipid A proximal inner core region oligosaccharides of some bacterial lipopolysaccharides increase the expression of Ts activity; due mainly to the capacity of such oligosaccharides, which are relatively conserved in structure among gram-negative bacterial, to enlarge or expand upon the population of $CD8^+$ Ts generated during the course of a normal antibody response to unrelated microbial antigens. The minimal structure required for the expression of the added immunosuppression observed was reported to be a hexasaccharide containing one 2-keto-3-deokyoctonate residue, two glucose residues, and three heptose residues to which are attached two pyrophosphorylethanolamine groups (Baker et al., 1994). This information may be considered in utilizing or even designing further adjuvants for use in the invention.

In a generally related line of work, Tanamoto et al. (1994a;b; 1995) described the dissociation of endotoxic activities in a chemically synthesized Lipid A precursor after acetylation or succinylation. Thus, compounds such as "acetyl 406" and "succinyl 516" (Tanamoto et al., 1994a;b; 1995) are also contemplated for use in the invention.

Synthetic MPLs form a further group of suitable adjuvants. For example, Brade et al. (1993) described an artificial glycoconjugate containing the bisphosphorylated glucosamine disaccharide backbone of lipid A that binds to anti-Lipid A MAbs. This is one candidate for use in certain aspects of the invention.

The MPL derivatives described in U.S. Pat. No. 4,987,237 are also contemplated for use in the present invention. U.S. Pat. No. 4,987,237 describes MPL derivatives that contain one or more free groups, such as amines, on a side chain attached to the primary hydroxyl groups of the monophosphoryl lipid A nucleus through an ester group. The derivatives provide a convenient method for coupling the lipid A through coupling agents to various biologically active materials. The immunostimulant properties of lipid A are maintained. All MPL derivatives in accordance with U.S. Pat. No. 4,987,237 are envisioned for use as adjuvants with this invention.

Various adjuvants, even those that are not commonly used in humans, may still be employed in animals, where, for example, one desires to subsequently obtain activated T cells or to protect valuable or valued animals from infection.

VIII. Therapeutic Kits

The present invention also provides therapeutic kits comprising *Coccidioides* spp. peptide and/or nucleic acid component(s) for use in the present treatment methods. Such kits will generally contain, in suitable container means, a pharmaceutically acceptable formulation of at least one of the *Coccidioides* spp. peptides and/or nucleic acids of the invention. The kits may also contain other pharmaceutically acceptable formulations for combined vaccination or therapy. For example, such kits may contain any one or more of a range of *Coccidioides* spp. antigens or conventional anti-fungal therapeutics.

Acyl urea compounds may be used to treat *Coccidioides* spp. and diseases such as coccidioidomycosis. These include acyl urea compounds such as those disclosed in U.S. Pat. Nos. 5,420,163 and 5,837,734, each specifically incorporated herein by reference.

The kits may have a single container (container means) that contains the *Coccidioides* spp. peptide or DNA component, with or without any additional components, or they may have distinct containers for each desired agent. Where combined therapeutics are provided, a single solution may be pre-mixed, either in a molar equivalent combination, or with one component in excess of the other. Alternatively, each of the *Coccidioides* spp. peptide or DNA components and other agents, such as *C. immitis* antigens and/or antifungal therapeutics may be maintained separately within distinct containers prior to administration to an animal or patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the *Coccidioides* spp. peptide component and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the *Coccidioides* spp. peptide component to an animal or patient, e.g., one or more needles or syringes, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

In general, the kits may also contain diagnostic components so that the invention may be used to confirm the presence *Coccidioides* spp. peptide prior to treatment, and/or determine the degree of *Coccidioides* spp. in a biological sample from a patient. Combined detection kits may thus include diagnostic agents, proteins, antibodies and nucleic acids.

Kits with components for detection can also be used to monitor the success of vaccination and/or therapies against *Coccidioides* spp. infection. The lack of detection of *Coccidioides* spp., or a decrease in the levels of *Coccidioides* spp. in comparison to the levels in a corresponding biological sample prior to therapy, is indicative of a patient that is being successfully treated for the condition associated with *Coccidioides* spp. infection or colonization.

IX. Therapeutic Regimens

Particularly important embodiments of the present invention concern the use of the peptides and DNA in immunological-based therapies for the prevention or treatment of *Coccidioides* spp. infections and associated diseases and conditions. The treatment of patients with Valley Fever is particularly contemplated, although the treatment also extends to veterinary embodiments and to prophylactic measures in subjects at risk for *Coccidioides* spp. infection and/or those traveling to infected areas. In fact, since protective immunity is shown herein, the present invention is particularly useful for preparing vaccines.

Therefore, the invention encompasses *Coccidioides* spp. peptide antigen and/or nucleic acid compositions, or "vaccines", preferably formulated with pharmaceutically acceptable carriers, diluents and/or adjuvants. Other formulations, vaccines or "antigenic cocktails" are also provided, comprising additional components, such as peptides, antigens, adjuvants, multimers and the like, as are often employed in the formulation of vaccines.

The present invention thus particularly provides methods of generating an immune response, preferably, a protective immune response, which methods generally comprise administering to an animal, including a human subject, a pharmaceutically acceptable composition comprising an immunologically effective amount of a *Coccidioides* spp. peptide or nucleic acid composition in accordance with the invention. The composition may include partially or significantly purified *Coccidioides* spp. peptides, obtained from natural or recombinant sources. Smaller peptides that include immunogenic epitopes, such as those between about 8 and about 12 amino acids may be used. The *Coccidioides* spp. peptides may also be combined with other agents and *Coccidioides* spp. components, as desired.

By "immunologically effective amount" is meant an amount of a *Coccidioides* spp. peptide or DNA composition that is capable of generating an immune response in the recipient animal or patient, preferably a protective immune response. This particularly includes the generation of T cell responses, including cytotoxic T cell responses, but also the generation of antibody responses (B cell response). The generation of immune responses, whether or not they are immunoprotective, has significant utility in the production of useful bioreagents, e.g., activated T cells and even reactive antibodies, for use as tools and in diagnostic embodiments. Therefore, although the invention includes vaccination regimens, it will be understood that achieving "vaccination" is not necessary for practicing all useful aspects of the invention.

The invention is preferably used in the generation of immunoprotective responses that have important utility in various clinical and veterinary prophylactic and therapeutic embodiments. Accordingly, such methods for the stimulation of an immune response include vaccination regimens designed to prevent or lessen *Coccidioides* spp. infections and associated diseases, and treatment regimens that may lessen the severity or duration of any infection or medical condition. So, even where therapy and vaccination are concerned, it will be understood that complete protection any from *Coccidioides* spp. infection whatsoever is not a requirement of the invention and that any clinical or veterinary benefit is a useful outcome of practicing the invention.

The use of the present *Coccidioides* spp. peptides, and even shorter peptides that incorporate *Coccidioides* spp. N-terminal epitopes, provides various advantages. Exemplary advantages include the ease of preparation and purification, the relatively low cost and improved reproducibility of production, and advantageous biodistribution. The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, each incorporated herein by reference.

Whether peptide- or DNA-based, various methods of achieving adjuvant effects for the vaccines are included. For example, the use of agents such as aluminum hydroxide or phosphate (alum), commonly used as 0.05 to 0.1 percent solution in phosphate buffered saline; and admixtures with synthetic polymers of sugars (Carbopol) used as 0.25 percent solution. Emulsions in physiologically acceptable oil vehicles such as mannide mono-oleate (Aracel A) or emulsion with 20 percent solution of a perfluorocarbon (Fluosol-DA) used as a block substitute may also be employed.

One may also generate an immune response in an animal or patient by administering to the animal or human subject a pharmaceutically acceptable composition comprising an immunologically effective amount of a *Coccidioides* spp. peptide-encoding nucleic acid composition, or even an immunologically effective amount of an attenuated live organism that includes and expresses a *Coccidioides* spp. peptide-encoding nucleic acid composition (see below). As with the peptide vaccines and therapeutics, the "immunologically effective amounts" are those amounts capable of stimulating T cell and/or B cell responses, preferably T cell responses, and more preferably, proving immunoprotection.

All vaccines of the invention should be administered in a manner compatible with the dosage formulation, and in such amount as will be immunogenic and therapeutically effective. The quantity to be administered depends on the subject to be treated, including, e.g., the capacity of the individual's immune system to react, and the degree of protection/treatment desired. Precise amounts of active ingredient required to be administered will be readily determinable by the skilled practitioner. Suitable regimes for initial administration and booster shots are also variable, and are typified by an initial administration followed by subsequent inoculations or other administrations.

The manner of application may be varied widely. Any of the conventional methods for administration of a vaccine are applicable. These will include oral application on a solid physiologically acceptable base or in a physiologically acceptable dispersion, parenterally, by injection and the like. The dosage of the vaccine may also vary with the route of administration.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels. The course of the immunization may be followed by assays for activated T cells produced.

X. DNA Vaccination

In light of the significant working examples herein, and the knowledge of those of ordinary skill in the art regarding DNA vaccination, it will be understood that virtually all vaccination regimens of the present invention are appropriate for use with *Coccidioides* spp. genetic immunization. In addition to parenteral routes of DNA inoculation, including intramuscular and intravenous injections, mucosal vaccination is also contemplated, as may be achieved by direct application.

The stimulation of specific antibodies and cell-mediated immune responses by administering to an animal a nucleic molecule is now well known in the art, as evidenced by articles such as Tang et al. (1992); Cox. et al. (1993;) Fynan et al. (1993); Ulmer et al. (1993); Wang et al. (1993) and Whitton et al. (1993); each incorporated herein by reference. The use of attenuated organisms, such as vaccinia viruses and *salmonella*, that express recombinant DNA products is also now established in the art and contemplated for use in the present invention.

The naked DNA technology, often referred to as genetic immunization, is particularly suitable to protect against infectious organisms. Immunization with DNA has been successfully employed to protect animals from challenge with influenza A (Ulmer et al., 1993). The use of the *Coccidioides* spp. peptide-encoding nucleic acid compositions of the present invention in such genetic immunization techniques is thus another useful vaccination regimen. The *Coccidioides* spp. peptide-encoding nucleic acid segments could be used in virtually any form, including naked DNA and plasmid DNA, and may be administered to the animal in a variety of ways, as described, for example, by Fynan et al. (1993).

In addition to naked DNA technology, or genetic immunization, using recombinant DNA or plasmids, other embodiments of the invention deliver DNA entrapped in liposomes or lipofectamine-DNA complexes. In yet further embodiments, the ability of viruses to enter cells and to integrate into host cell genome is used to transfer *Coccidioides* spp. peptide nucleic acids into target cells. Gene therapy vectors of the present invention thus include viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941, incorporated herein by reference, may also be engineered to serve as vectors for gene transfer.

Adenoviruses do not integrate their genetic material into the host genome and therefore do not require host replication for gene expression, making them ideally suited for rapid, efficient, heterologous gene expression. Adenoviral vectors may be employed with the present invention, and techniques for preparing replication-defective infective viruses are well known in the art.

In certain further embodiments, an HSV gene therapy vector may be used. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

XI. Recombinant Vectors, Host Cells and Expression

Recombinant vectors form important further aspects of the present invention. As described in the foregoing sections, recombinant expression may be used in this invention to prepare peptides for subsequent delivery or to express peptides in vivo, wherein a therapeutic benefit naturally results. Unless otherwise particularly specified, the recombinant vectors discussed herein include those for use in vitro and in vivo.

The term "recombinant vector, expression vector or construct", as used herein, thus means any type of genetic construct containing a nucleic acid coding for an expressed product in which part or all of the nucleic acid encoding sequence is capable of being transcribed. Typically, the transcript is translated into a peptide or protein. Thus, "expression" preferably includes both transcription of a nucleic acid segment and translation of mRNA into a product.

Vectors typically have a coding portion of a nucleic acid or DNA segment positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" mean that the promoter is in the correct location and orientation in relation to the nucleic acid segment to control RNA polymerase initiation and expression of the nucleic acid segment.

The promoter may be in the form of the promoter that is naturally associated with the *Coccidioides* spp. Ag2/PRA, as is known in the art and as may be obtained by isolating the 5' non-coding sequences located upstream of the coding segment, for example, using recombinant cloning and/or PCR™ technology, in connection with the compositions disclosed herein. PCR™ technology is disclosed in U.S. Pat. Nos. 4,683,202 and 4,682,195, each incorporated herein by reference.

In other embodiments, certain advantages will be gained by positioning the coding nucleic acid or DNA segment under the control of a recombinant, or heterologous, promoter. As used herein, a recombinant or heterologous promoter refers to a promoter that is not normally associated with *Coccidioides* spp. Ag2/PRA in its natural environment. Such promoters may include promoters normally associated with other nucleic acids and genes, and/or promoters. isolated from any other bacterial, viral, eukaryotic, or mammalian cell.

Naturally, it will be important to employ a promoter that effectively directs the expression of the nucleic acid or DNA segment in the cell type or organism chosen for expression. The use of promoter and cell type combinations for protein expression is generally known to those of skill in the art of molecular biology, for example, see Sambrook et al. (1989; incorporated herein by reference). The promoters employed may be constitutive, or inducible, and can be used under the appropriate conditions to direct high level expression of the introduced nucleic acid or DNA segment, such as is advantageous in the large-scale production of recombinant proteins or peptides.

At least one module in a promoter functions to position the start site for RNA synthesis.

The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid of the invention is not believed to be critical, so long as it is capable of expressing the nucleic acid in the targeted cell. Thus, where a mammalian or human cell is targeted, it is preferable to position the nucleic acid coding region adjacent to and under the control of a promoter that is capable of being expressed in a mammalian or human cell. Generally speaking, such a promoter might include either a mammalian, human or viral promoter. Exemplary promoters include those derived from HSV and tetracycline controlled promoters.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well-known in the art to achieve expression of a transgene are contemplated as well, provided that the levels of expression are sufficient for a given purpose. Virtually any element/promoter may be employed in the context of the present invention to regulate the *Coccidioides* spp. peptide expression.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene of the invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

As indicated, it is contemplated that one may use any regulatory element to express the *Coccidioides* spp. peptide of the present invention. However, under certain circumstances it may be desirable to use the innate promoter region associated with the gene of interest to control its expression, such as the native *Coccidioides* spp. Ag2/PRA promoter. As noted above, in most cases, genes are regulated at the level of transcription by regulatory elements that are located upstream, or 5', to the genes.

In general, to identify regulatory elements for *Coccidioides* spp. Ag2/PRA, one would obtain a genomic DNA segment corresponding to the region located between about 5 to 50 nucleotides up to about 2000 nucleotides or more upstream from the transcriptional start site of the gene. A convenient method used to obtain such a sequence is to utilize restriction enzyme(s) to excise an appropriate DNA fragment. Restriction enzyme technology is commonly used in the art and will be generally known to the skilled artisan. For example, one may use a combination of enzymes from the extensive range of known restriction enzymes to digest the genomic DNA. Analysis of the digested fragments would determine which enzyme(s) produce the desired DNA fragment. The desired region may then be excised from the genomic DNA using the enzyme(s). If desired, one may even create a particular restriction site by genetic engineering for subsequent use in ligation strategies.

Alternatively, one may choose to prepare a series of DNA fragments differentiated by size through the use of a deletion assay with linearized DNA. In such an assay, enzymes are also used to digest the genomic DNA; however, in this case, the enzymes do not recognize specific sites within the DNA but instead digest the DNA from the free end(s). In this case, a series of size differentiated DNA fragments can be achieved by stopping the enzyme reaction after specified time intervals. Of course, one may also choose to use a combination of both restriction enzyme digestion and deletion assay to obtain the desired DNA fragment(s).

Once the desired DNA fragment has been isolated, its potential to regulate a gene and determine the basic regulatory unit may be examined using any one of several conventional techniques. It is recognized that once the core regulatory region is identified, one may choose to employ a longer sequence that comprises the identified regulatory unit. This is because although the core region is all that is ultimately required, it is believed that particular advantages may accrue, in terms of regulation and level of induction achieved, where one employs sequences that correspond to the natural control regions over longer regions. The preferred length will be in part determined by the type of expression system used and the results desired.

Numerous methods are known in the art for precisely locating regulatory units within larger DNA sequences. Most conveniently, the desired control sequence is isolated within a DNA fragment(s) that is subsequently modified using DNA synthesis techniques to add restriction site linkers to the fragment(s) termini. This modification readily allows the insertion of the modified DNA fragment into an expression cassette that contains a reporter gene that confers on its recombinant host cell a readily detectable phenotype that is either expressed or inhibited, as may be the case.

Generally reporter genes encode a polypeptide not otherwise produced by the host cell; or a protein or factor produced by the host cell but at much lower levels; or a mutant form of a polypeptide not otherwise produced by the host cell. Preferably the reporter gene encodes an enzyme that produces a colorimetric, fluorometric or other readily detectable change in the host cell, which is detectable by in situ analysis and is a quantitative or semi-quantitative function of transcriptional activation. Exemplary reporter genes encode esterases, phosphatases, proteases and other proteins detected by activity that generates a chromophore or fluorophore, as will be known to the skilled artisan. Two well-known examples of such reporter genes are *E. coli* beta-galactosidase and chloramphenicol-acetyl-transferase (CAT). Alternatively, a reporter gene may render its host cell resistant to a selection agent. For example, the gene neo renders cells resistant to the antibiotic neomycin. It is contemplated that virtually any host cell system compatible with the reporter gene cassette may be used to determine the regulatory unit. Thus mammalian or other eukaryotic cells, insect, bacterial or plant cells may be used.

Once a DNA fragment containing the putative regulatory region is inserted into an expression cassette, which is in turn inserted into an appropriate host cell system using any of the techniques commonly known to those of skill in the art, the ability of the fragment to regulate the expression of the reporter gene is assessed. By using a quantitative reporter assay and analyzing a series of DNA fragments of decreasing size, for example produced by convenient restriction endonuclease sites, or through the actions of enzymes such as BAL31, *E. coli* exonuclease III or mung bean nuclease, and which overlap each other a specific number of nucleotides, one may determine both the size and location of the native regulatory unit.

Of course once the core regulatory unit has been determined, one may choose to modify the regulatory unit by mutating certain nucleotides within the core unit. The effects of these modifications may be analyzed using the same reporter assay to determine whether the modifications either enhance or reduce transcription. Thus key nucleotides within the core regulatory sequence can be identified.

It is recognized that regulatory units often contain both elements that either enhance or inhibit transcription. In the case that a regulatory unit is suspected of containing both types of elements, one may use competitive DNA mobility shift assays to separately identify each element. Those of skill in the art will be familiar the use of DNA mobility shift assays.

It may also be desirable to modify the identified regulatory unit by adding additional sequences to the unit. The added sequences may include additional enhancers, promoters or even other genes. Thus one may, for example, prepare a DNA fragment that contains the native regulatory elements positioned to regulate one or more copies of the native gene and/or another gene or prepare a DNA fragment that contains not one but multiple copies of the promoter region such that transcription levels of the desired gene are relatively increased.

Turning to the expression of the *Coccidioides* spp. peptide, once a suitable clone or clones have been obtained, one may proceed to prepare an expression system. The engineering of DNA segment(s) for expression in a prokaryotic or eukaryotic system may be performed by techniques known to those of skill in recombinant expression. It is believed that virtually any expression system may be employed in the expression of the proteins of the present invention.

In expression, one will typically include a polyadenylation signal to effect proper polyadenylation of the transcript. The nature of the polyadenylation signal is not believed to be crucial to the successful practice of the invention, and any such sequence may be employed. The SV40 polyadenylation signal is convenient and is known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals may be used. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

The *Coccidioides* spp. peptides of the present invention may be co-expressed with any other protein or peptide, such as another *Coccidioides* spp. antigen. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of the *Coccidioides* spp. peptide with another protein or peptide in the same recombinant cell.

As used herein, the terms "engineered" and "recombinant" cells refer to a cell into which an exogenous nucleic acid or DNA segment has been introduced. Therefore, engineered cells are distinguishable from naturally occurring cells, which do not contain a recombinantly introduced exogenous nucleic acid or DNA segment. Engineered cells are thus cells having a nucleic acid or DNA segment introduced through the hand of man. Recombinant cells also include those having an introduced nucleic acid or DNA segment positioned adjacent to a promoter not naturally associated with the particular introduced nucleic acid or DNA segment. Recombinant cells of the present invention also include those in which the *Coccidioides* spp. peptide-encoding sequences have been removed, i.e., "knock-outs".

To express a recombinant *Coccidioides* spp. peptide in accordance with the invention one would prepare an expression vector that comprises a *Coccidioides* spp. peptide-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli*, fungi and yeast transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No.31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors; and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media. The expression of the recombinant protein may be induced, e.g., by adding IPTG to the media (if an inducible expression construct is used) or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation that more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the particular coding sequences.

In a useful insect system, *Autograph californica* nuclear polyhedrosis virus (AcNPV) is used as a vector to express foreign genes. The virus grows in *Spodoptera frugiperda* cells. The *C. immitis* peptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, WI 38, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. The promoters may be derived from the genome of mammalian cells (e.g., metallothionein promoter) or from mammalian viruses (e.g., the adenovirus late promoter; the vaccinia virus 7.5K promoter).

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant *Coccidioides* spp. peptides, stable expression may be used and cell lines that stably express the *Coccidioides* spp. peptides may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance can be used as the basis of selection for dhfr, which confers resistance to methotrexate; gpt, which confers resistance to mycophenolic acid; neo, that confers resistance to the aminoglycoside G418; and hygro, which confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the *Coccidioides* spp. peptides of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

The following examples are included to demonstrate certain preferred embodiments of the invention. It will be appreciated by those of skill in the art that the compositions and techniques disclosed in the examples that follow represent compositions and techniques discovered by the inventor to function well in the practice of the invention, and thus can be considered to constitute certain preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Analysis of Full Length Recombinant Ag2/PRA as an Immunogen

The Ag2/PRA cDNA contains a 582 bp open reading frame that encodes a 19.4 kDA protein (Zhu et al., 1995; 1996b). Ag2/PRA cDNA was subcloned into the pGEX plasmid and expressed as a glutathione-S-transferase (GST) fusion protein in *Escherichia coli* (Jiang et al., 1999a; specifically incorporated herein by reference).

Figure 1B:
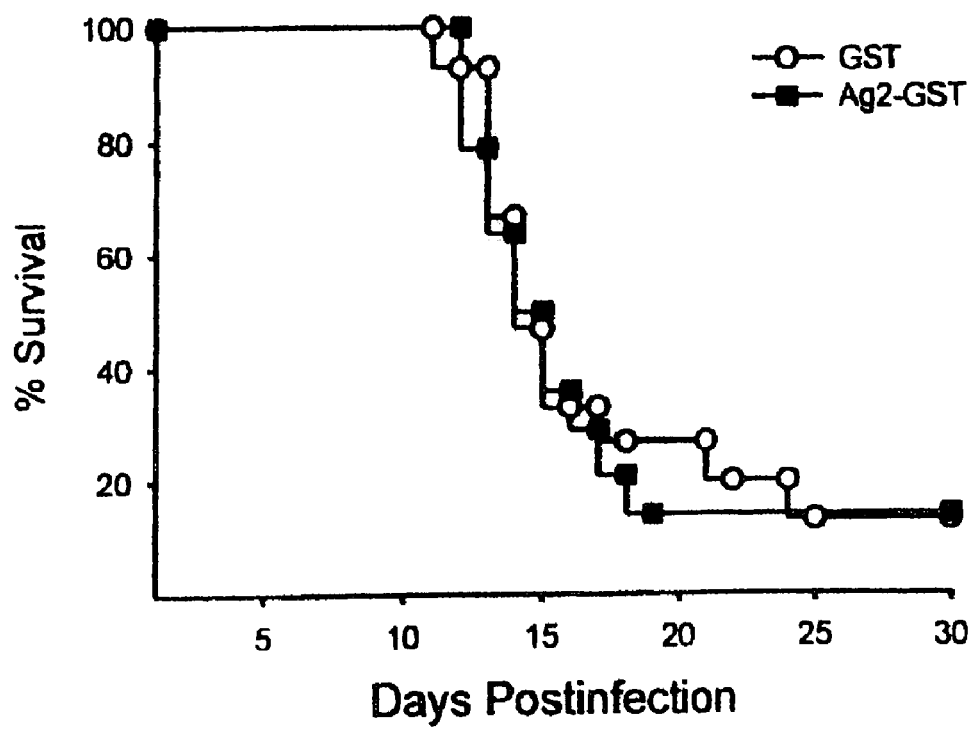

BALB/c mice, which are highly susceptible to *C. immitis*, were immunized with three weekly injections of 100 µg of the recombinant Ag2/PRA-GST protein in RIBI adjuvant and then challenged with 250 arthroconidia of *C. immitis* strain Silveira via the intraperitoneal (i.p.) route. The results established that the Ag2/PRA-GST recombinant protein induced a significant level of protection as measured by a decrease in the fungal colony forming units (CFU) in the livers and spleens 12 days postinfection as compared with mice receiving the GST peptide alone ($p<0.025$ by Wilcoxon rank sums test) (FIG. 1A). The recombinant Ag2/PRA did not, however, increase the survival of the vaccinated mice over a 30-day period postinfection (FIG. 1B).

Mice were also immunized with rAg2/PRA-GST in different RIBI adjuvants. Mice immunized with rAg2/PRA-GST in RIBI MPL-SE adjuvant had a significantly reduced fungal load in their spleens as compared to control mice receiving RIBI MPL-SE adjuvant alone ($p<0.05$). The use of rAg2/PRA-GST in RIBI 730/700 adjuvant did not give statistically significantly results. In controlled studies to analyze the fungal CFU in the lungs, rAg2/PRA-GST-conferred protection was not observed irrespective of the adjuvant used, although the formalin-killed spherule (FKS) vaccine (positive control) resulted in a significant reduction in fungal load.

The low efficacy of the recombinant Ag2/PRA-GST fusion protein contrasts with earlier studies showing that C-ASWS, an alkali-soluble, water-soluble cell wall extract that includes Ag2/PRA as one component, protected mice against lethal challenge with *C. immitis* (Lecara et al., 1983). One explanation for the differences is that recombinant Ag2/PRA lacks post-translational modification(s), particularly glycosylations.

Genetic immunization offers a means for expressing native antigens in vivo and gene vaccines have been reported to be highly effective in inducing long lasting immunity in animal models (Babiuk, 1999; Lee et al., 1998; Hui et al., 1999; Hota-Mitchell et al., 1999; Zhu et al., 1997a; Gurunathan et al., 2000). The efficacy of genetic immunization using an Ag2/PRA-expressing plasmid was therefore evaluated (Jiang et al., 1999a). The full-length Ag2/PRA cDNA was ligated to the plasmid pVR1012 (Vical Inc.) and used in genetic immunization.

Figure 2A:
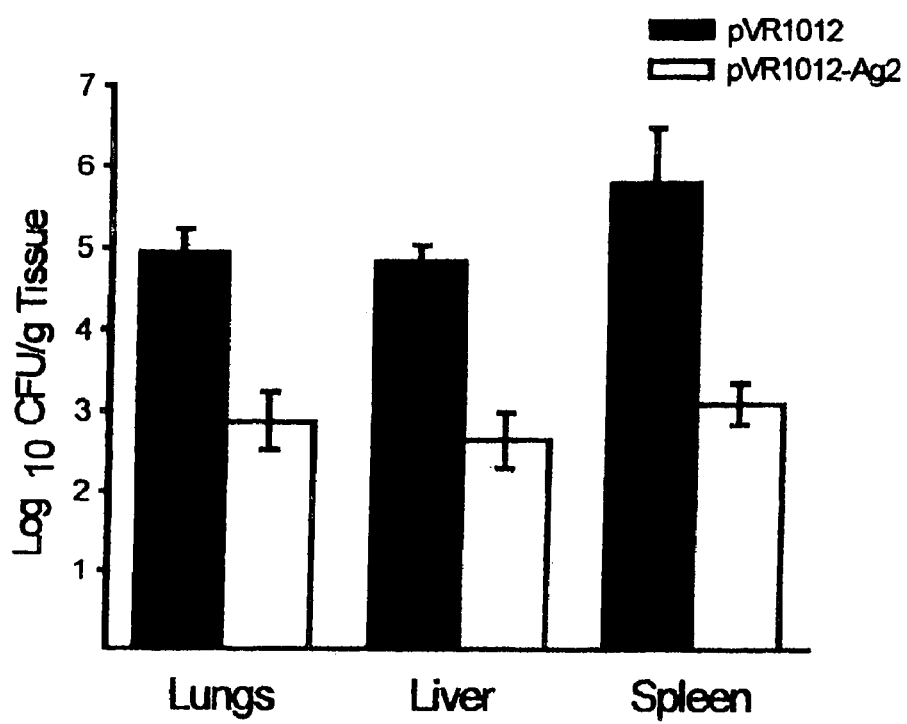
FIG. 2A and FIG. 2B. Genetic immunization of mice with vector expressing full length Ag2/PRA (pVR1012-Ag2). BALB/c mice were immunized with three weekly injections of pVR1012-Ag2/PRA (50 µg per dose) and then challenged with 2,500 arthroconidia of *C. immitis* via the i.p. route.
Figure 2B:
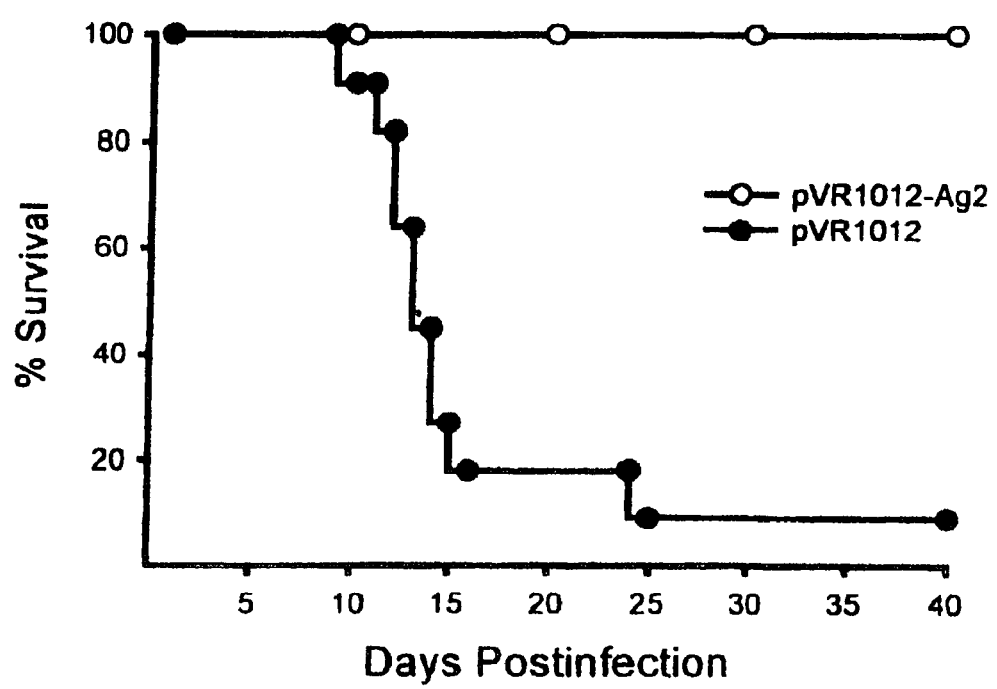

Groups of 10 BALB/c mice were given three weekly intramuscular injections of the pVR1012-Ag2/PRA cDNA at a dose of 50 µg per injection. Mice immunized with the Ag2/PRA cDNA-pVR1012 construct showed a significant decrease ($p<0.001$) in the fungal CFUs in their lungs, livers, and spleens 12 days after i.p. challenge with 2,500 arthroconidia, as compared with mice immunized with the vector alone (FIG. 2A). It is noteworthy that the challenge dose in these two studies, 2,500 arthroconidia, is ten-fold greater than that used to challenge mice immunized with the recombinant rGST-Ag2/PRA protein (compare FIG. 2B with FIG. 1B). Mice immunized with Ag2/PRA cDNA also showed an increased survival of mice over a 40-day period after i.p. challenge (FIG. 2B). In fact, all of the immunized mice survived 40 days postinfection.

Coccidioidomycosis is acquired by inhalation of arthroconidia. Hence, the ability of Ag2/PRA to engender protection against pulmonary challenge was tested. As genetic immunization out-performed protein immunization, studies were conducted to assess the protective capacity of Ag2/PRA cDNA against intranasal (i.n.) instillation of 25 arthroconidia The formalin-killed spherule (FKS) vaccine was included as a comparative control.

Figure 3:
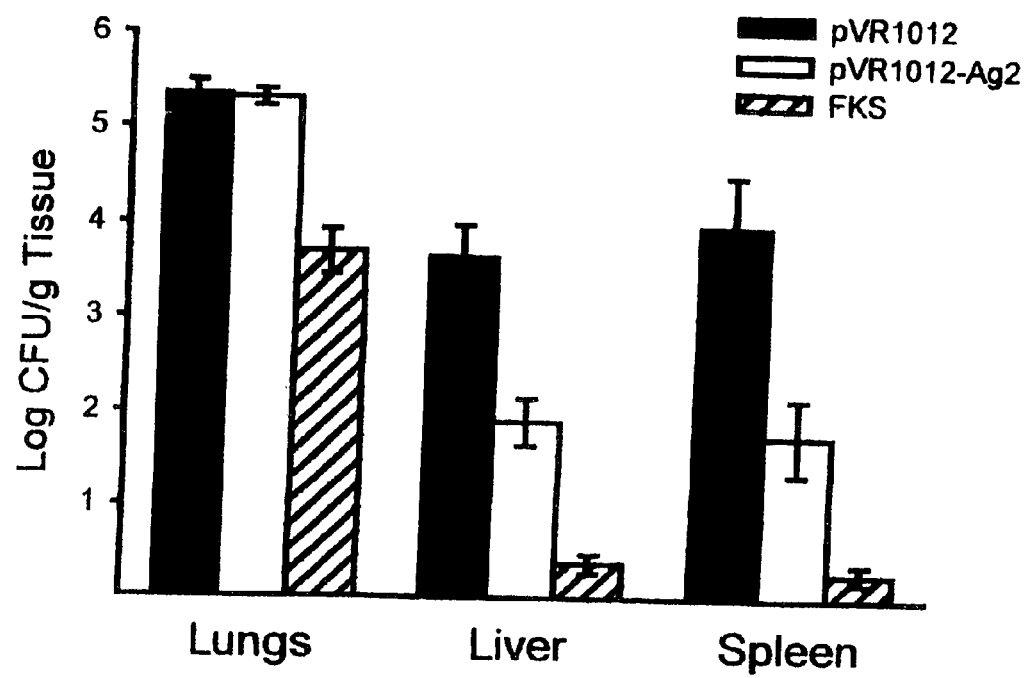
FIG. 3. Immunization of mice prior to after intranasal (i.n.) challenge with arthroconidia. BALB/c mice were immunized with Ag2/PRA cDNA or formalin-killed spherule (FKS) vaccine and then challenged with 25 arthroconidia of *C. immitis* via intranasal (i.n.) instillation. The CFU in immunized mice at 12 days postinfection are shown.
Figure 4:
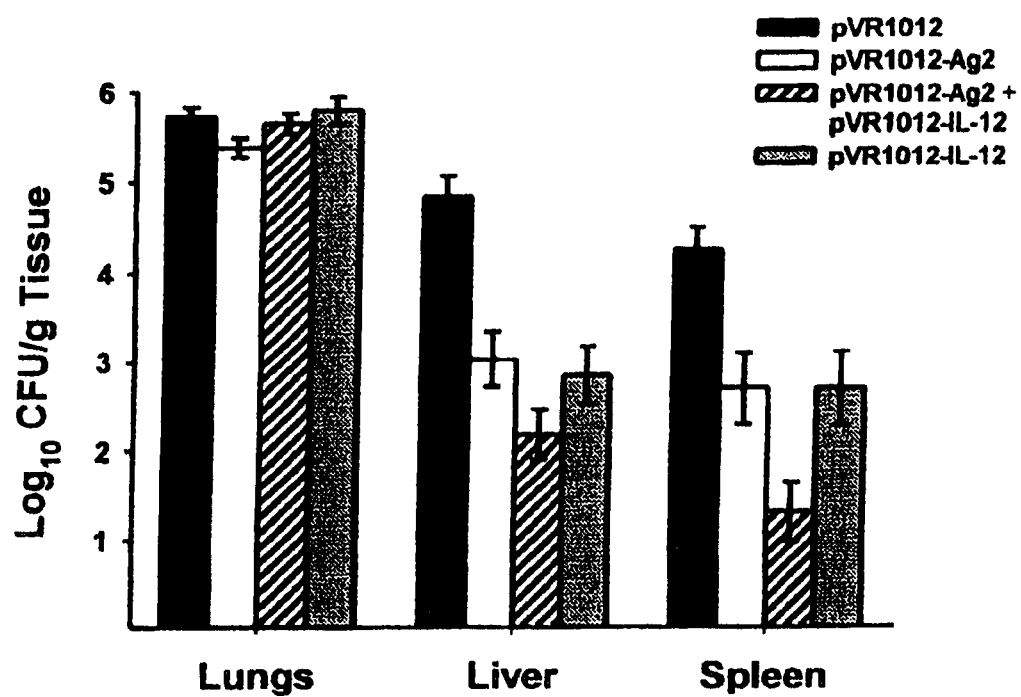
FIG. 4. IL-12 gene adjuvant enhances Ag2/PRA cDNA vaccine efficacy. Ag2/PRA and a single-chain IL-12 cDNA (p40-L-p35) were subcloned into the pVR1012 plasmid. BALB/c mice were immunized with the resultant plasmid and then exposed to pulmonary challenge. The CFU in various tissues of the immunized mice are shown.
Figure 5:
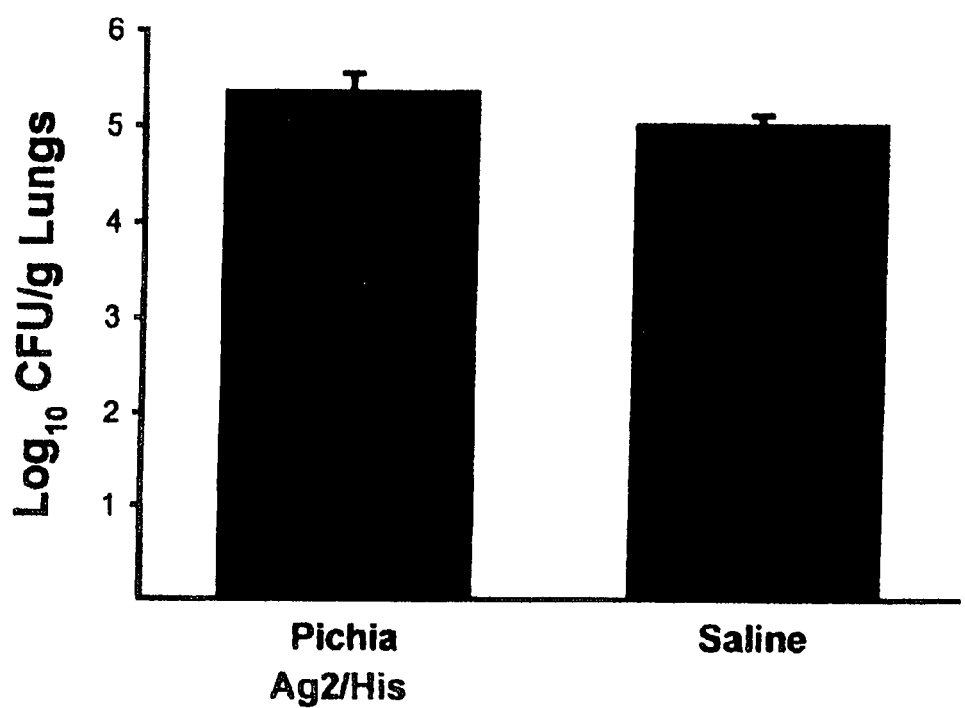
FIG. 5. Lack of protection against pulmonary challenge in mice immunized with *Pichia*-expressed Ag2/PRA. Ag2/PRA was ligated to the PIC Z alpha plasmid vector and expressed in *Pichia pastoris* as a C-terminal his-tagged recombinant product. Mice were immunized with *Pichia*-expressed Ag2/PRA and then challenged with 25 arthroconidia of *C. immitis* strain Silveira via the pulmonary route. Despite glycosylation, *Pichia*-expressed recombinant Ag2/PRA did not protect mice against pulmonary challenge.

The Ag2/PRA cDNA vaccine protected mice from pulmonary challenge with 25 arthroconidia, as evidenced by a significant decrease ($p<0.015$) in the fungal load in the livers and spleens at 12 days postinfection. CFU in lung tissue were not reduced, however, in the Ag2/PRA cDNA-vaccinated mice when compared to mice immunized with the plasmid alone (FIG. 3). By contrast, mice vaccinated with the formalin-killed spherule (FKS) vaccine (2.1 mg total dose, given in three weekly immunizations) were strongly protected, both in the lungs and extrapulmonary organs ($p<0.0001$). The increased efficacy of the FKS vaccine as compared with Ag2/PRA cDNA could be attributable to the presence of other immunogens (in addition to Ag2/PRA) and/or the finding that killed spherules are potent inducers of proinflammatory cytokines (e.g., TNF-α, IL-1) which could intensify the induction and persistence of the cellular immune response to the vaccine (Slagle et al., 1989; Dooley et al., 1994; Ampel, 1994).

Resistance to *C. immitis* is mediated by T helper 1 (Th1) lymphocytes and is accompanied by the induction of delayed-type hypersensitivity and production of Th1- associated cytokines such as IFN-γ, IL-2, and IL-12 (Beaman et al., 1977; 1981; Beaman, 1987; Cox and Vivas, 1977; Cox et al., 1977; 1988; Ampel et al., 1992; Magee and Cox, 1995; 1996; Corry et al., 1996; Cox and Magee, 1998). Studies were therefore undertaken to assess the immune response to the Ag2/PRA gene vaccine and, for comparison, the FKS vaccine (Table 1).

Mice vaccinated with the Ag2/PRA cDNA ligated to the pVR1012 plasmid showed a strong footpad hypersensitivity and their spleen cells elaborated IFN-γ when cultured in vitro in the presence of coccidioidin (CDN). These Th1 responses were also demonstrable in mice immunized with FKS and, in terms of magnitude, were increased when compared to the levels obtained in mice vaccinated with Ag2/PRA cDNA. The Ag2/PRA gene vaccine also induces IgG. Enzyme immunoassays for IgG isotype responses to CDN showed that mice immunized with Ag2/PRA cDNA or FKS produced a predominant IgG1 response as opposed to an IgG2a response, despite the fact that IgG1 antibody production is typically associated with a Th2 rather than a Th1 immune response (Mosmann and Coffman, 1989).

TABLE 1

Immune Responses in Mice Vaccinated with Ag2/PRA cDNA or FKS

| Vaccine | Footpad hypersensitivity (mm × $10^{-2}$) | IFN-γ production (pg/ml) | Anti-CDN IgG (ELISA A410 nm) | |
|---|---|---|---|---|
| | | | IgG1 | IgG2a |
| pVR1012 | 6.4 ± 1.1 | 15 | 0.04 | 0.08 |
| pVR1012-Ag2/PRA | 16.5 ± 2.6 | 320 | 1.01 | 0.03 |
| FKS | 30.5 ± 8.3 | 1,000 | 2.39 | 0.03 |

Interleukin-12 (IL-12) plays a central role in the induction of host defense against C. immitis (Magee and Cox, 1996). Administration of recombinant IL-12 before and during the course of the disease protected BALB/c mice against i.p. challenge and effected a shift in the Th1 response. IL-12 cDNA also amplifies Th1 responses to microbial vaccines (Chow et al., 1998; Sin et al., 1999; Tsuji et al., 1997). The ability of IL-12 cDNA to augment the protective capacity of the Ag2/PRA gene vaccine against pulmonary challenge (Jiang et al., 1999b) was therefore assessed.

The Ag2/PRA cDNA and a single-chain IL-12 cDNA (p40-L-p35) were both subcloned into the pVR1012 plasmid and used in immunization. The results establish that this dual immunization significantly enhanced protection against the extrapulmonary dissemination of the fungus ($p<0.0001$ for the liver and spleens), but did not enhance protection at the lung level when compared with mice given the Ag2/PRA cDNA alone or pVR1012 alone (FIG. 4). The enhanced protection was associated with increased IFN-γ secretion, production of IgG2a, and the influx of CD4+ and CD8+ T cells in lungs and spleens (Jiang et al, 1999b). It is noteworthy that the increased influx of CD8+ T cells would suggest that cytotoxic T cells are activated in response to *C. immitis.*

EXAMPLE II

Analysis of Recombinant Ag2/PRA from Eukaryotic Expression

The low efficacy of the recombinant Ag2/PRA-GST fusion protein (Example I) could possibly be explained by the fact that Ag2/PRA lacks post-translational modification (s). This is scientifically reasonable as native Ag2/PRA is heavily glycosylated, containing the unusual methylated carbohydrate 3-O-methylmannose (Cole et al, 1985). Consistent with this, the translated Ag2/PRA cDNA contains 24 potential sites for O-glycosylation (Zhu et al., 1995). The translated Ag2/PRA cDNA also contains 8 cysteine residues that could be involved in disulfide bond linkages and three sites for phosphorylation. While these post-translational modifications would not bear T cell epitopes, they could be important for imparting a conformational structure that is required for optimal antigen processing or presentation (Jentoft, 1990; Ishioka et al., 1992; Harding et al., 1993).

Since glycosylation, disulfide bonding, and phosphorylation require a eukaryotic expression system, Ag2/PRA was ligated to the PIC Z alpha plasmid vector and expressed in *Pichia pastoris* as a C-terminal his-tagged recombinant product. When evaluated by immunoblot analysis using *coccidioidomycosis* patients' sera, the *Pichia*-expressed Ag2/PRA showed two bands, as earlier seen with the *E. coli*-expressed Ag2/PRA. However, unlike *E. coil*-expressed Ag2/PRA, the higher molecular size band in the *Pichia*-expressed Ag2/PRA showed a diffuse staining pattern.

The presence of glycosylation in the *Pichia*-expressed Ag2/PRA was confirmed using an enzyme immunoassay for detecting carbohydrate residues. *Pichia*-expressed recombinant Ag2/PRA was strongly positive for carbohydrate, whereas the *E. coli*-expressed Ag2/PRA-GST recombinant peptide was negative.

Crossed immunoelectrophoresis of the *Pichia*-expressed Ag2/PRA against hyperimmune goat anti-CDN antisera revealed a single peak that had a diffusely staining cathodal precipitin leg, consistent with native Ags (Cox, 1989; Lecara et al., 1983), and usually denoting glycosylation. A clear anodal peak characteristic of the Ag2/PRA polymer was not seen, but the anodal precipitin leg did show a curve towards the anode.

In initial studies, it was not possible to recover sufficient quantities of the full-length recombinant Ag2/PRA (1–194) in the supernatant of transformed *Pichia* yeast cells to allow immunization studies. It was reasoned that the signal peptide was hampering recovery of the expressed polypeptide. Accordingly, a truncated version of recombinant Ag2/PRA including amino acids 19–194 was used to transform *Pichia* and the expressed polypeptide was obtained.

Immunization with the *Pichia*-expressed truncated Ag2/PRA did not protect BALB/c mice against pulmonary challenge with 25 or 50 arthroconidia (FIG. 5), as measured by the fungal load in the lungs. The FKS vaccine, as a comparative control, induced a strong level of protection.

In these studies, the presence of glycosylation, and other post-translational modifications that might be present on Ag2/PRA, was not able to confer the ability to protect mice against pulmonary challenge. Thus, although it remains possible that *Pichia*-expressed Ag2/PRA does not contain O-glycosylations, particularly the O-methylmannose component of native Ag2/PRA, the initial conclusion is that post-translational modifications do not appear to be necessary for the vaccine efficacy of Ag2/PRA. It was subsequently realized that these adverse results, using *Pichia*-expressed, truncated Ag2/PRA (amino acids 19–194), suggest that the N-terminal signal peptide may be important for induction of protective immunity.

EXAMPLE III

Sequence Variation, Kinetics and Prime/Boost Immunizations

During the course of the foregoing and other studies, it was realized that the Ag2/PRA (19–194) cDNA construct used in immunization contained five mutations in comparison to SEQ ID NO:3 and SEQ ID NO:4. The site of the mutations, the correct sequences according to the GenBank entry for Ag2/PRA cDNA (SEQ ID NO:3 and SEQ ID NO:4), the sequence mutations, and their effect are summarized in Table 2.

TABLE 2

Mutations within 19-194 Ag2/PRA cDNA

| Site | Genbank | Mutation | Effect |
| --- | --- | --- | --- |
| Leucine 55 | CTC | CTA | Silent |
| Glutamic Acid 135 | GAG | GTG | Valine |
| Alanine 178 | GCC | GAC | Aspartic Acid |
| Tyrosine 193 | TAC | TGC | Cysteine |
| Stop | TAA | TAG | Silent |

Two of the mutations, one in the codon encoding for leucine at 55, and one within the stop codon, are silent, i.e. without any effect in the translated protein. The other three changed the translated sequence, from glutamic acid at 135 to valine, from alanine at 178 to aspartic acid, and from tyrosine at 193 to cysteine. Although computer-based algorithms for predicting antigenicity (Jameson and Wolf, 1988) did not indicate that these mutations altered the antigenic sites within these regions, a new Ag2/PRA (19–194) cDNA construct was generated with the correct sequence (SEQ ID NO:3 and SEQ ID NO:4) and tested in immunization.

In such studies, no differences were observed in the protection induced in mice immunized with the new (correct sequence) Ag2/PRA (19–194) cDNA and the mutant Ag2/PRA (19–194) cDNA. That is, the mean CFU in mice immunized with the two constructs and then challenged with 2,500 arthroconidia were 2.72±0.83 and 3.35±0.46, respectively ($p>0.05$).

Routinely, mice are given three immunizations over a three week period and then challenged two weeks after the third immunization. To begin to delineate the optimal kinetics for the induction of protection in mice vaccinated with Ag2/PRA cDNA or derived constructs, the following studies were conducted.

Groups of 10 BALB/c mice were immunized at three weekly intervals with 50 μg of Ag2/PRA (1–194) cDNA and the mice challenged intraperitoneally with 2,500 arthroconidia at week 2, 3, 4, 5, or 6 after the third immunization. The results were expressed as mean CFU in the lungs and spleens. All of the groups vaccinated with Ag2/PRA cDNA showed a significant decrease in their fungal load as compared to the vector control group ($p<0.0001$). There was not a statistically significant decrease in the mean CFU in lungs or spleens of mice challenged at various weeks post immunization.

Figure 6A:
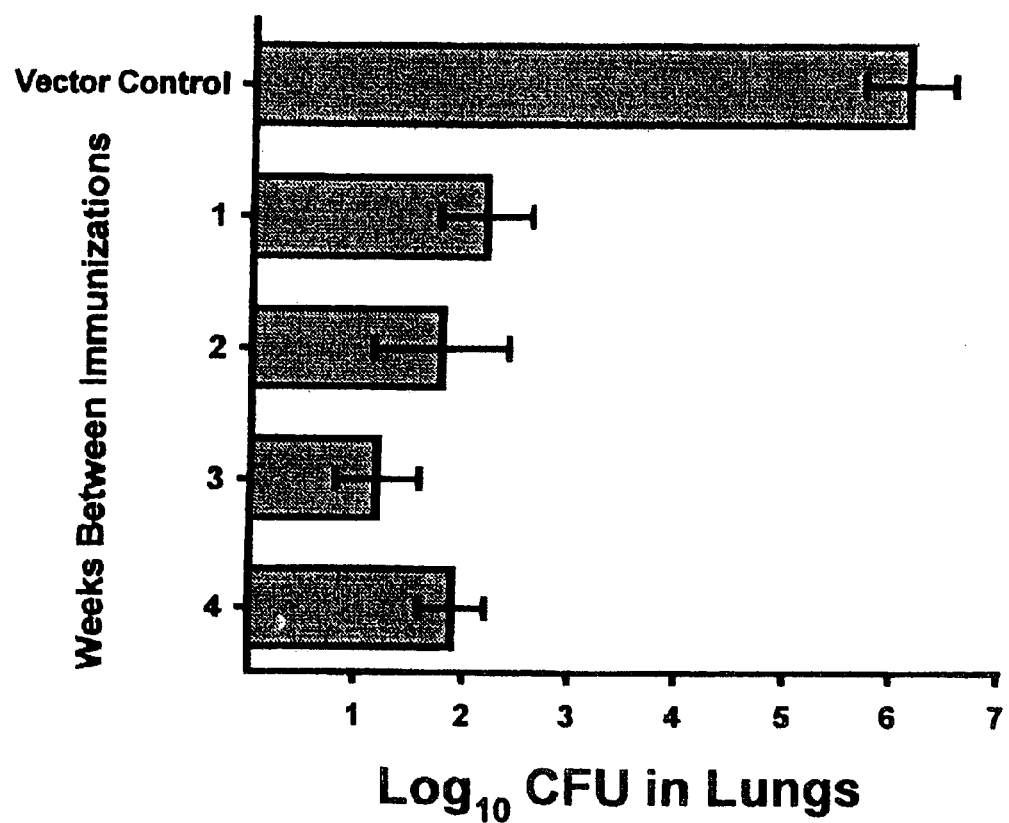
FIG. 6A and FIG. 6B. Effect on protection by increasing times between immunizations. Groups of BALB/c mice were immunized with 50 µg of Ag2/PRA (1–194) cDNA at the weekly intervals shown and then challenged intraperitoneally with 2,500 arthroconidia after the third immunization.
Figure 6B:
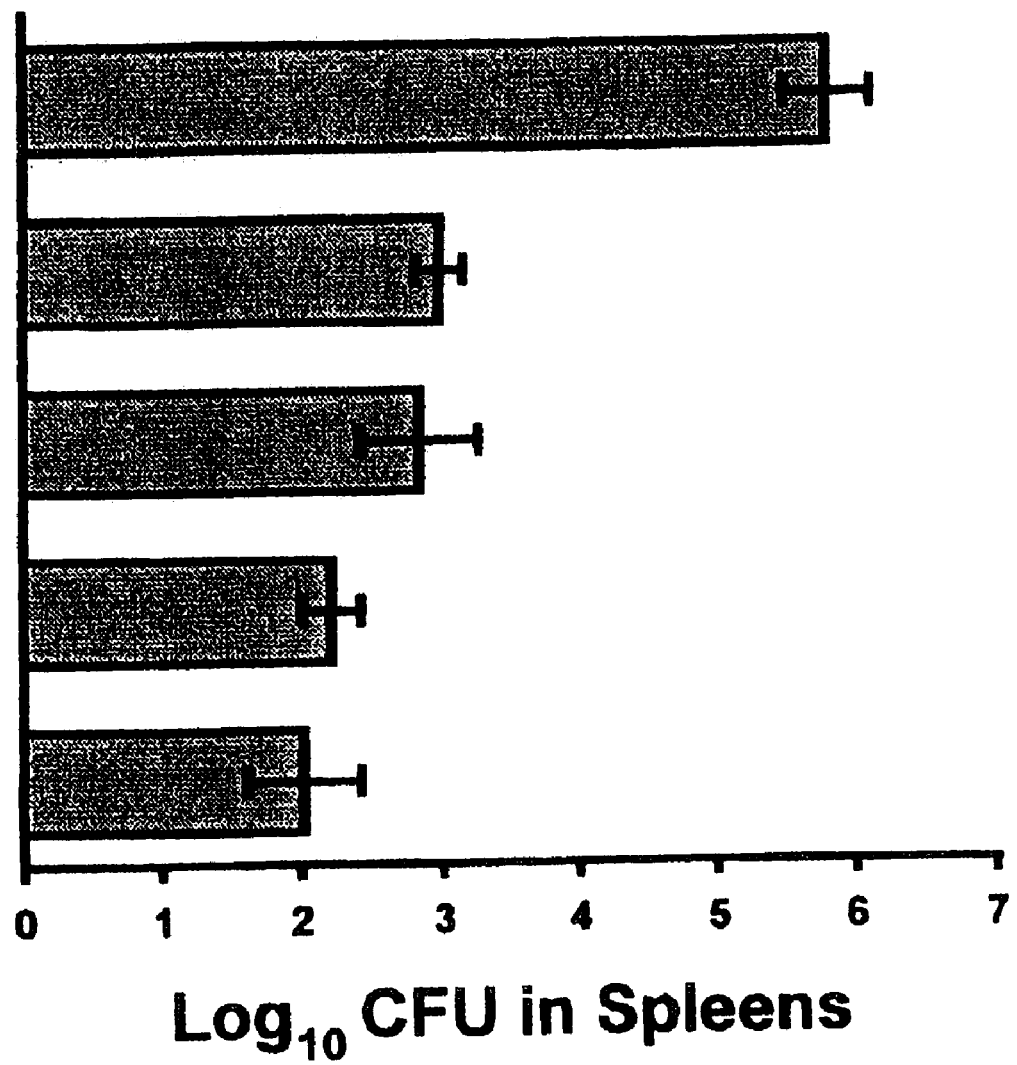
Figure 7:
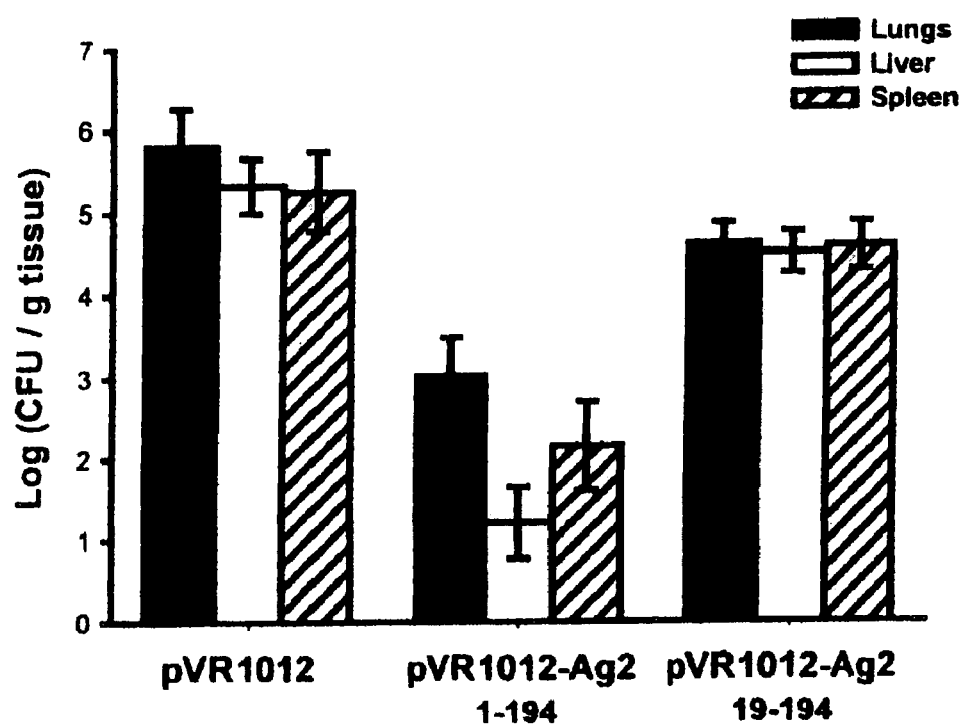
FIG. 7. Comparison of vaccine efficacy of full length and truncated Ag2/PRA. cDNAs encoding full length Ag2/PRA (1–194) and truncated Ag2/PRA (19–194) were generated and inserted into the pVR1012 plasmid. Mice were immunized with these plasmids and then challenged with arthroconidia of *C. immitis*. The CFU in various tissues of the immunized mice with the different plasmids are shown.
Figure 8:
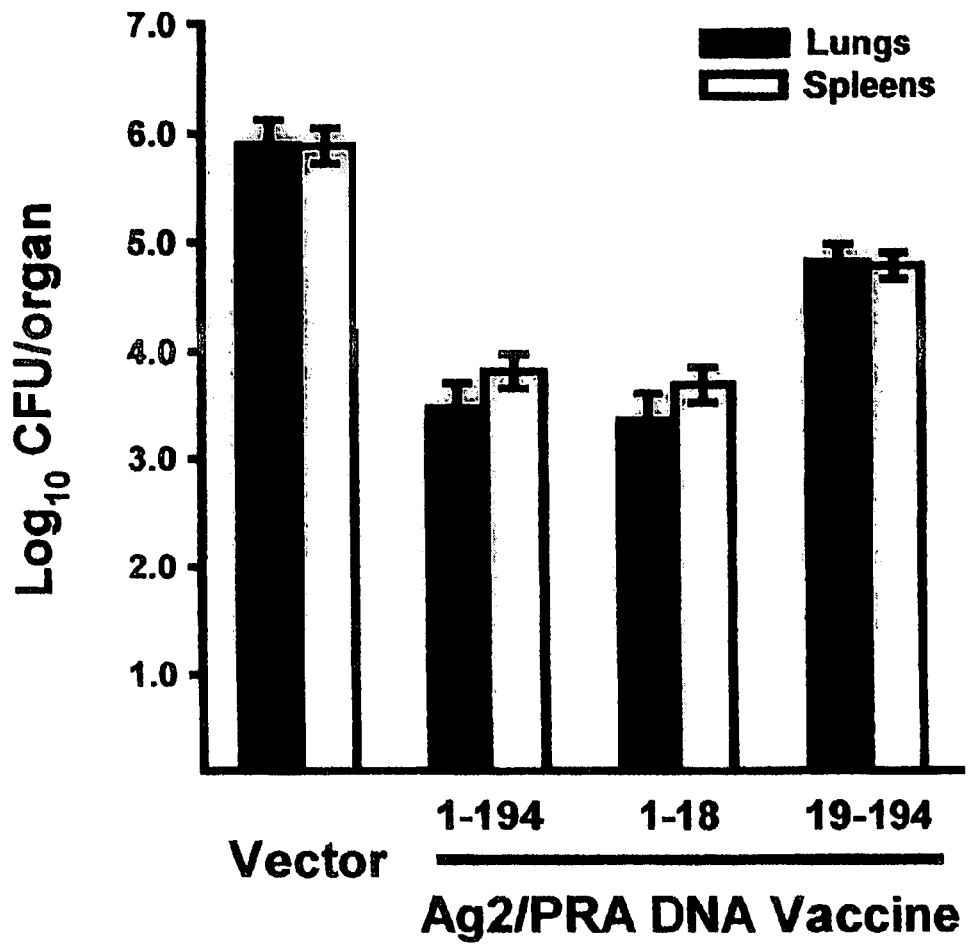
FIG. 8. Protective efficacy of Ag2/PRA (1–18) cDNA construct against i.p. challenge. The vaccine efficacy of the full-length Ag2/PRA (1–194) DNA, signal sequence-truncated Ag2/PRA (19–194) DNA and the signal sequence Ag2/PRA (1–18) DNA were determined in BALB/c mice, as assessed by measuring the fungal CFU in the lungs and spleens 12 days after i.p. challenge with 2,500 arthroconidia. Results depict the $\log_{10}$ CFU (mean±standard error) obtained in four separate studies, each involving 9 or more mice per group.

The effect of increasing the time between each of the three immunizations was also examined. Increasing the time from one week to three weeks between immunizations appeared to augment the protective effect observed in the lungs (FIG. 6A), and this effect was even more pronounced in the spleens (FIG. 6B).

In studies of *Plasmodium berghei*, primary immunization with a gene vaccine encoding a protective antigen of *P. berghie*, followed by boosting with the recombinant product, markedly enhanced protection (Degano et al., 2000; Schneider et al., 1988). This strategy was evaluated by priming BALB/c mice with Ag2/PRA cDNA, the pVR1012 vector alone, or FKS and then boosting 7 days later with Ag2/PRA cDNA and, at day 14, boosting with Ag2/PRA cDNA, FKS, or the *Pichia*-expressed rAg2/PRA. Twelve days after the final boost, the mice were challenged by an intranasal instillation of 50 arthroconidia.

The results established that mice vaccinated with FKS, followed by two boosts with Ag2/PRA cDNA, were significantly protected against pulmonary challenge with 50 arthroconidia, as measured by the reduced fungal loan in the lungs. The reverse sequence, i.e., priming with Ag2/PRA cDNA followed by a boost with Ag2/PRA cDNA and then a boost with FKS also protected the mice, but to a lesser extent.

This emphasizes that protection against pulmonary challenge is possible with Ag2/PRA cDNA, which is important for vaccine efficacy. It bears emphasis that this protection was not attributable to FKS alone; that is, a single immunization with FKS does not protect against pulmonary challenge. The minimal dose of FKS needed to prime the mice for boosting with Ag2/PRA cDNA is determinable.

EXAMPLE IV

The Signal Peptide is Cleaved in Eukaryotic Expression

Subsequent studies were conducted to identify the N-terminal amino acid sequence of *Pichia*-expressed Ag2/PRA. Specifically, to determine whether the first 18 N-terminal amino acids were present in the *Pichia*-expressed product, or whether Ag2/PRA was secreted from *Pichia* cells without this putative signal peptide.

In analyzing both bands of *Pichia*-expressed Ag2/PRA, it was determined that the N-terminal amino acids began with residues 19–23, thereby establishing that mature Ag2/PRA lacks the N-terminal 18 amino acids. This is consistent with the finding that *Pichia*-expressed Ag2/PRA is expressed at high levels in the supernatant and not in the cell lysate of these yeast cells. These data also establish that the 18 N-terminal amino acids function as a signal peptide.

EXAMPLE V

The Sisal Peptide is Important in Immunoprotection

Ag2/PRA cDNA induces a strong level of protection in BALB/c mice challenged by an i.p. route and limits dissemination of the fungus in mice challenged by the pulmonary route (Example I). Immunization with eukaryotic expressed Ag2/PRA, which was glycosylated, but truncated in comparison to the full length protein, did not protect mice against pulmonary challenge with 25 arthroconidia. The lack of effectiveness of glycosylated, but truncated Ag2/PRA (amino acids 19–194), suggested to the inventors that the N-terminal signal peptide may be important for induction of protective immunity (Example II). The present and subsequent examples therefore concern studies to delineate the protective domain of Ag2/PRA cDNA.

In the first of these studies, Ag2/PRA cDNA truncations were generated by the polymerase chain reaction (PCR™), inserted into the pVR1012 plasmid, and evaluated for their protective capacity in mice. One of the most striking results was the finding that mice immunized with Ag2/PRA (19–194) cDNA, which encodes a polypeptide lacking the 18 amino acid N-terminal signal peptide (Zhu et al., 1995; 1996b), was significantly less protective than the full-length Ag2/PRA (1–194) cDNA gene (FIG. 7). Note the decreased CFU in mice immunized with the full-length Ag2/PRA cDNA (1194), but not the truncated Ag2/PRA cDNA (19–194) (FIG. 7).

The present example therefore shows that the 18 N-terminal amino acids are important in vaccine efficacy. This finding is consistent with reports that other DNA vaccines without the leading signal sequence are less immunogenic than their full-length counterparts (Baldwin et al., 1999; Drew et al., 2000; Haddad et al., 1998; Kamath et al., 1999).

The finding that the signal peptide region is important to the protective capacity of the Ag2/PRA gene vaccine prompted an analysis of this region for potential T cell-reactive epitopes. Database searches for T cell-reactive epitopes revealed that the signal peptide has a very high probability of containing a Class I binding motif, a finding that suggests cytotoxic T cells might be important in host defense againset C. immitis (Table 3). To target the gene to Class I as well as Class II pathways, mice are immunized with Ag2/PRA cDNA ligated to a plasmid that encodes a modified form of listeriolysin-O protein (Bouwer et al., 1999). QFSHALIAL is residues 2 through 10 of SEQ ID NO:2; EFPGAGSNV is residues 168 through 176 of SEQ ID NO:4; and ALLGLAAYL is residues 186 through 194 of SEQ ID NO:4.

TABLE 3

MHC Peptide Motifs in Ag2/PRA

| Rank | MHC Class I Score | Start Position | Sequence |
|---|---|---|---|
| 1 | 1152 | 2 | QFSHALIAL |
| 2 | 200 | 168 | EFPGAGSNV |
| 3 | 115.2 | 186 | ALLGLAAYL |

EXAMPLE VI

The Signal Peptide Alone is as Effective as the Entire Protein

As shown in Example V, despite various possibilities, including the lack of O-glycosylation of the proper fidelity, the inventors defined that the lack of effectiveness of the eukaryotic expressed Ag2/PRA was due in substantial part to the absence of the N-terminal signal peptide. In the truncation studies, the N-terminal signal peptide of 18 amino acids was discovered to be important in the induction of protective immunity.

The present example shows that, surprisingly, this N-terminal amino acid sequence, which is normally cleaved from the Ag2/PRA polypeptide, is not only important in vaccine efficacy, but confers protection when used alone. Even more surprisingly, it is shown that the protective efficacy of the N-terminal peptide is essentially the same as that of the full length Ag2/PRA.

A. Materials and Methods

1. Vaccine Plasmid Construction

The full-length Ag2/PRA cDNA, which has a 582 bp open reading frame (SEQ ID NO:3) and encodes the 194 amino acid protein (SEQ ID NO:4), was subcloned into the XbaI and BamHI site of the eukaryotic expression vector plasmid pVR1012 (Vical, Inc., San Diego, Calif.) using standard techniques (Jiang et al., 1999c; incorporated herein by reference).

The pVR1012-Ag2/PRA (1–18) DNA was constructed by the following procedure. First, the DNA sequence encoding the 1–18 amino acids on the N-terminus was amplified on the template pVR1012-Ag2/PRA (1–194) plasmid by PCR™ with upstream 5'-TTGGGATCCGTCGACATGCAGTTCTCTCAC-3' (SEQ ID NO:5) and downstream 5'-GGAAGATCTCGAGTTAGGCACTGGCGAGGCC-3' (SEQ ID NO:6) primers. The reaction conditions were 95° C. for 4 min., followed by 30 cycles at 95° C. for 60 sec., 60° C. for 30 sec., and 72° C. for 45 sec., and then a final extension at 72° C. for 7 min. The PCR™ fragment was digested with BamHI and BglII, purified on 3% agarose gel, and then ligated into pVR1012 vector (Vical, Inc., San Diego, Calif.). After transformation, a positive colony was picked from Luria Broth (LB) agar containing kananycin and sequenced for confirmation of signal peptide sequence in the correct reading frame. A similar strategy was used to generate the recombinant pVR1012-Ag2/PRA (19–194) DNA construct (Zhu et al., 1997; incorporated herein by reference).

2. Preparation of Plasmid DNA

To prepare plasmid DNA for immunization, *E. coli* DH5α cells were transformed with the DNA constructs or the vector plasmid alone and then cultured at 37° C. for 16 h. in LB supplemented with kanamycin (50 μg/ml). Plasmid DNA was isolated using an EndoFree™ plasmid purification kit (Qiagen, Santa Clara, Calif.). Plasmid DNA was resuspended in USP saline (Baxter Healthcare Corporation, Deerfield, Ill.) and stored at −20° C. until used. The endotoxin level was less than 0.1 unit per μg DNA for each construct when assayed with the QCL-1000 Limulus Amebocyte Lysate kit (BioWhittaker, Walkersville, Md.).

3. Gene Expression of Plasmid DNA in Mammalian Cells

To establish that the pVR1012-based Ag2/PRA constructs would be expressed in mammalian cells, a transient transfection assay was performed (Jiang et al., 1999a; incorporated herein by reference). Using the LipofectAMINE Plus™ in Kit (GIBCO, NY), 2 μg of Ag2/PRA (1–194) DNA, Ag2/PRA (19–194) DNA, and Ag2/PRA (1–18) DNA were transfected into non-tumorigenic CL-7 fibroblast cells, which were originally derived from BALB/c mice (Patek et al., 1978). The cells were grown in Dulbecco's minimal essential medium (DHEM) (GIBCO, Grand Island, N.Y.) supplemented with 10% fetal calf serum and 4. 5 mg/ml glucose, and then plated into 6-well plates at a concentration of $4\times10^5$ cells/well. After an overnight incubation, the cells were transfected and, three days later, the cells were harvested and total RNA was isolated for RT-PCR™. The RNA samples from the transfected cells were analyzed simultaneously with the primers for each Ag2/PRA construct.

The RNA was transcribed into cDNA by using reverse transcriptase (Perkin Elmer Inc., NJ). The primers for Ag2/PRA (1–18) were the same as listed above. The following primers were used for mRNA expression of Ag2/PRA (1–194) and Ag2/PRA (19–194): upstream 5'-ATGCAGTTCTCTCACGCTCTCATC-3' (SEQ ID NO:7) and 5'-ATGCAGCTCCCAGACATCCCACCT-3' (SEQ ID NO:8), respectively; and downstream for both Ag2/PRA (1–194) and Ag2/PRA (19–194), 5'-TTACAGGTAGGCAGCGAGACC-3' (SEQ ID NO:9). The conditions for the PCR™ were the same as reported in Jiang et al. (1999a; incorporated herein by reference). All PCR™ products were electrophoresed in 2.5% agarose gel to confirm the size of fragments.

4. Synthesis of Ag2/PRA Signal Peptide

The 18 amino acid peptide (MQFSHALIALVAAGLAS; SEQ ID NO:2) corresponding to the signal sequence of Ag2/PRA was synthesized as a chloride salt by Bachem Bioscience (King of Prussia, PA) and the Protein Core Facility at the University of Texas Health Science Center-San Antonio using FMOC-solid phase synthesis and HPLC purification techniques. Electrospray mass spectrophotometry and amino acid analysis were used to verify that the Ag2/PRA (1–18) peptide preparations were of the correct molecular weight and predicted amino acid content. Lyophilized peptides were stored under nitrogen gas before reconstitution in sterile 100% dimethyl sulfoxide (DMSO) to a concentration of 2 mg/ml.

5. Immunization

Five-week old female BALB/c (H-$2^d$) mice were purchased from Jackson Laboratory (Bar Harbor, Me.). The mice were maintained for at least one week before use.

DNA immunization was performed by injecting groups of 10 mice intramuscularly with 50 µg of either Ag2/PRA (1–194) DNA, Ag2/PRA (19–194) DNA, Ag2/PRA (1–18) DNA, or the pVR1012 vector alone, each in 50 µl of physiologic saline. Before each injection, the mice were lightly anesthetized via inhalation of Metofane (Mallinckrodt Veterinary, Inc., Mundelein, Ill.). Injections were given in the tibialis anterior muscle in a site which had been pretreated with Nair (Carter-Wallace, Inc., New York, N.Y.) one day before administering the first immunization. A total of three immunizations were given at weekly intervals in alternating sites on the left and right hind legs. Mice were challenged two weeks after the final immunization.

Immunization with the Ag2/PRA (1–18) synthetic peptide was performed by injecting mice intramuscularly with 100 µl containing 10 µg of the peptide diluted in 12.5% DMSO and admixed with an equal volume of complete Freund adjuvant. To minimize peptide precipitation during emulsification, 250 µl of the DMSO-solubilized peptide solution was drawn into a polypropylene syringe (Air-tite Products; Virginia Beach, Va.) containing 1 ml of adjuvant and then mixed with 750 µl of sterile saline using a three-way stopcock (Baxter Healthcare Corporation; Deerfield, Ill.). Mock control mice received 100 µg of the DMSO/adjuvant alone. Seven and 14 days after the first immunization, the mice were given subcutaneous injections of 100 µl containing 10 µg of the DMSO-solubilized peptide in incomplete Freund adjuvant.

6. Infection and Assessment of Disease Severity

Arthroconidia were harvested from 4- to 8-week-old mycelia-phase cultures of C. immitis strain Silveira. The arthroconidia suspensions were passed over a sterile nylon column to remove hyphal elements, and the cells were enumerated by hemacytometer counts. Mice were infected by an i.p. injection with 2,500 arthroconidia suspended in 0.5 ml of pyrogen-free saline, or by an intranasal instillation of 10 arthroconidia. The viability of the inocula was confirmed by plate counts on 1% glucose-2% yeast extract agar. All manipulations using viable *C. immitis* or infected tissues were performed in certified Biosafety Level-3 facilities.

Vaccine-induced protection was evaluated by quantifying the number of *C. immitis* CFU in the lungs and spleens 12 days postinfection (Jiang et al., 1999a;b;c; each incorporated herein by reference). Results were expressed as $\log_{10}$ CFU per organ. In selected studies, the protective capacity of Ag2/PRA DNA constructs was evaluated in terms of survival of mice at days 1 through 40 postinfection.

7. IFN-γ Induction and Analyses

To evaluate the induction of IFN-γ, spleens were isolated from mice 12 days after challenge and single cell suspensions were prepared by gently homogenization. Cells were suspended in cold Hank's Balanced Salt Solution and treated with isotonic ammonium chloride to lyse erythrocytes. The splenocytes were washed by centrifugation, resuspended in DMEM containing 10% fetal bovine serum, and dispensed to wells on a microtiter plate at a concentration of $2\times10^6$ mononuclear cells per well. The cultures were stimulated with 50 μg/ml of recombinant Ag2/PRA, which was expressed as a GST-Ag2/PRA (1–194) fusion protein (Zhu et al., 1996a), or 1 μg/ml synthetic Ag2/PRA (1–18) peptide. After a 48 h incubation at 37° C. under 5% $CO_2$, supernatants were collected and passed through a 0.45 micron filter to remove viable cells. IFN-γ was assayed by a two-site sandwich enzyme-linked immunoassay (ELISA) using affinity-purified rat IgG1 anti-mouse antibodies (PharMingen, San Diego, Calif.) as previously reported (Jiang et al., 1999a;b;c).

8. Analysis of Serum IgG Isotypes

Humoral immune responses were assessed by quantifying IgG1 and IgG2a isotype antibodies using an ELISA (Jiang et al., 1999b). Serum was collected from mice 12 days after challenge, filtered through a 0.45 micron filter, and stored at −20° C. until assayed. Two-fold serial dilutions were prepared and 0.1 ml of the diluted sera specimens was added to wells on a 96-well microtiter plate that had been coated with 100 ng of GST-Ag2 (1–194). Goat anti-mouse IgG1 and IgG2a antibodies (1:1000 dilution), each conjugated to alkaline phosphatase (Zymed, South San Francisco, Calif.), were used as second antibody. The plates were washed and the p-nitrophenyl phosphate substrate (Sigma) was added to obtain color development in 30 min. Plates were read at 410 nm on a MR-5000 microplate reader (Dynatech Inc., Lake Success, N.Y.). A serum pool prepared from more than 50 mice immunized with Ag2/PRA was used as. reference standard for quality control.

9. Statistical Analyses

The data were analyzed using the Wilcoxon rank-sums test. Differences in the survival of mice at days 1 through 40 postinfection were analyzed using the Kaplan-Meier procedure. Probability values of <0.05 were considered significant.

B. Results

1. In Vitro Expression in BALB/c Mouse-Derived Cells

The ability of pVR1012-based Ag2/PRA gene constructs to transfect mammalian cells was confirmed in vitro in the CL-7 cell line. A 66-bp band was amplified by PCR™ using cDNA template isolated from CL-7 cells transfected with Ag2/PRA (1–18) DNA. PCR™ products of 582 bp and 520 bp were obtained from cDNA samples from cells transfected with Ag2/PRA (1–194) and Ag2/PRA (19–194), respectively. Total RNA from CL-7 cells transfected with pVR1012 vector DNA showed no RT-PCR™ product. As CL-7 is a cell line established from BALB/c mouse strain (Patek et al., 1978), these results demonstrate that the Ag2/PRA DNA vaccine constructs have the potential to be expressed in vivo in BALB/c mice.

2. Protective Capacity of Ag2/PRA Signal Sequence Gene Vaccine

From the inventors' earlier finding that Ag2/PRA (1–194) DNA vaccine was more effective than recombinant Ag2/PRA protein in inducing protective immunity against *C. immitis* (Jiang et al., 1999c), DNA-based immunizations were first utilized to assess the protective capacity of the Ag2/PRA-derived constructs. As shown in Example V, initial studies indicated that cDNA constructs lacking the signal sequence were less protective than the full-length cDNA. This observation is borne out by the following data.

As shown in FIG. 8, and consistent with the studies in the earlier examples (Jiang et al., 1999c), mice immunized with Ag2/PRA (1–194) DNA showed a significant reduction in the number of CFU recovered from their lungs (P<0.0001) and spleens (P<0.0001), as compared to the control group that received the pVR1012 vector alone. Ag2/PRA (19–194) DNA, which lacks the signal peptide sequence, was significantly less protective as compared to Ag2/PRA (1–194) DNA (P<0.0001). Importantly, mice immunized with the Ag2/PRA (1–18) DNA signal sequence were strongly protected, to a level comparable to that observed in mice immunized with the full-length Ag2/PRA DNA.

Figure 9:
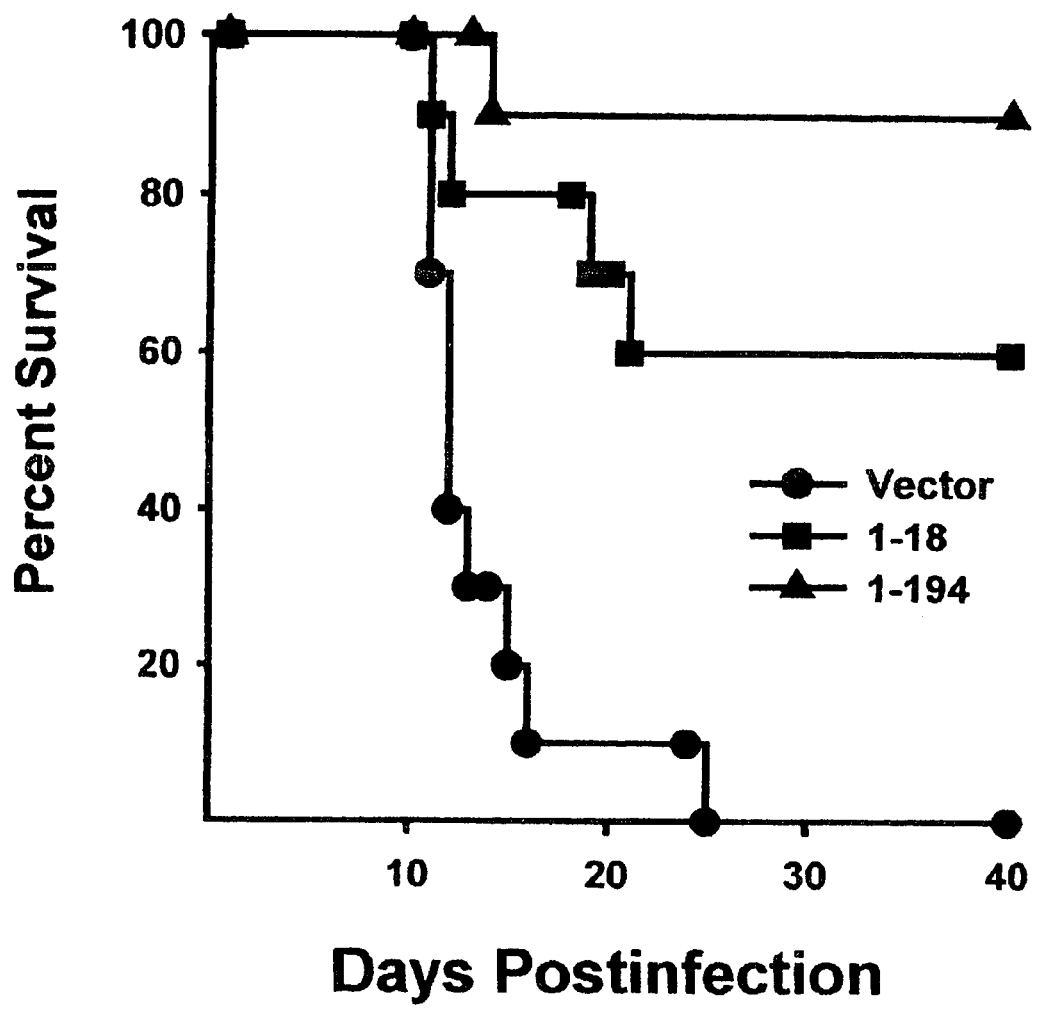
FIG. 9. Mice immunized with Ag2/PRA (1–18) cDNA survive i.p. challenge with arthroconidia. The percent survival of BALB/c mice immunized with the full length Ag2/PRA (1–194) DNA, signal gene Ag2/PRA (1–18) DNA, or the pVR1020 vector was determined after challenge with 2,500 arthroconidia via an i.p. route. Each group contained 10 mice.

The preceding results established that immunization of mice with the Ag2/PRA (1–18) signal sequence DNA effected a reduction in the fungal load in lungs and spleens 12 days after i.p. challenge. The protective capacity of the Ag2/PRA (1–18) DNA vaccine was further evaluated by monitoring survival in mice over a 40 day period following an i.p. challenge with 2,500 arthroconidia. As shown in FIG. 9, 60% of mice immunized with Ag2/PRA (1–18) DNA survived, while all mice immununized with the vector control died within 25 days (P<0.0001). Although 90% of mice vaccinated with Ag2/PRA (1–194) DNA survived challenge, this did not reflect a statistically significant increase in survival over the survival observed in mice vaccinated with Ag2/PRA (1–18) DNA.

Whereas immunization with Ag2/PRA (1–18) DNA induced protection in mice challenged with 2,500 arthroconidia by the i.p. route, the signal peptide gene vaccine did not protect mice against pulmonary challenge with 10 arthroconidia. This is consistent with results in the previous examples, showing that neither the full-length Ag2/PRA (1–194) DNA vaccine, nor recombinant GST-Ag2/PRA (1–194) induced protection against pulmonary challenge, as assessed by measuring the fungal load in the lungs 12 days after challenge or survival of the mice within a 30 day period after challenge (Jiang et al, 1999c).

Figure 10:
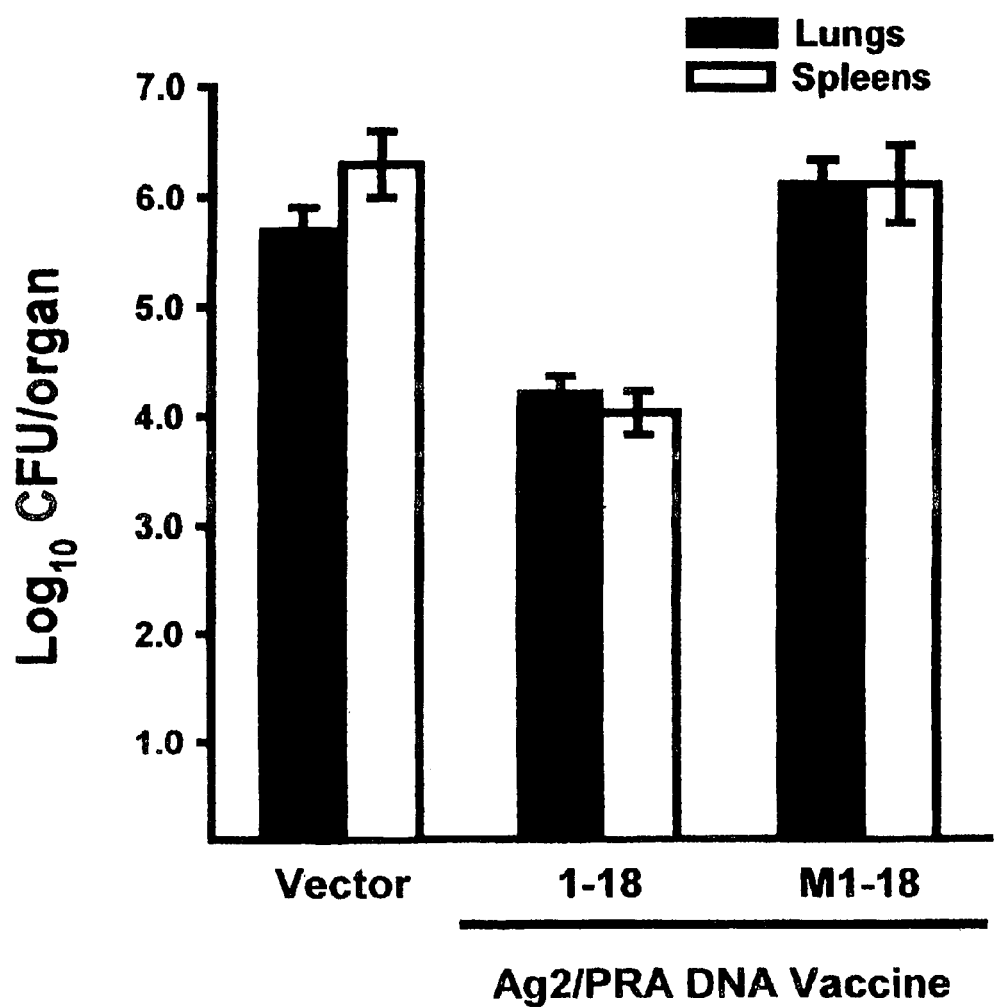
FIG. 10. The protective capacity of the Ag2/PRA (1–18) DNA is not attributable to a nonspecific immunopotentiation from nucleotide sequences. The vaccine efficacy of the native Ag2/PRA (1–18) DNA sequence and an Ag2/PRA "nonsense" sequence with a frame-shift mutation (M1–18) was determined in BALB/c mice challenged by an i.p. route with 2,500 arthroconidia. Results are expressed as the $\log_{10}$ CFU (mean±standard error) in tissues from groups of 10 mice at day 12 postinfection.

To confirm that the protective capacity of the Ag2/PRA (1–18) DNA was not attributable to a nonspecific immunopotentiation from nucleotide sequences (Ronaghy et al., 2002), a frame-shift mutation was created by fusing the Ag2/PRA (1–18) with ATG in the wrong reading frame. Mice immunized with DNA containing the frame-shift mutation (designated Ag2/PRA, M1–18) were not protected against i.p. challenge with 2,500 arthroconidia, whereas mice immunized with the correct Ag2/PRA (1–18) DNA construct showed greater than a log decrease in CFU in their lungs and spleens as compared to the vector control mice (FIG. 10).

3. Protective Efficacy of Synthetic Ag2/PRA (1–18) Signal Peptide

To date, the protective capacity of immunization with Ag2/PRA materials has shown DNA constructs to be more effective than their protein counterparts. The protective capacity of the Ag2/PRA (1–18) synthetic peptide was compared directly with the Ag2/PRA (1–18) DNA construct. Mice immunized with the synthetic peptide showed a mean lung $\log_{10}$ CFU of 4.9, as compared to a mean lung $\log_{10}$ CFU of 2.8 in mice immunized with Ag2/PRA (1–18) DNA. This also establishes that the synthetic peptide is less protective than the signal sequence DNA (P<0.005), as consistent with data using the full length protein and DNA.

Figure 11:
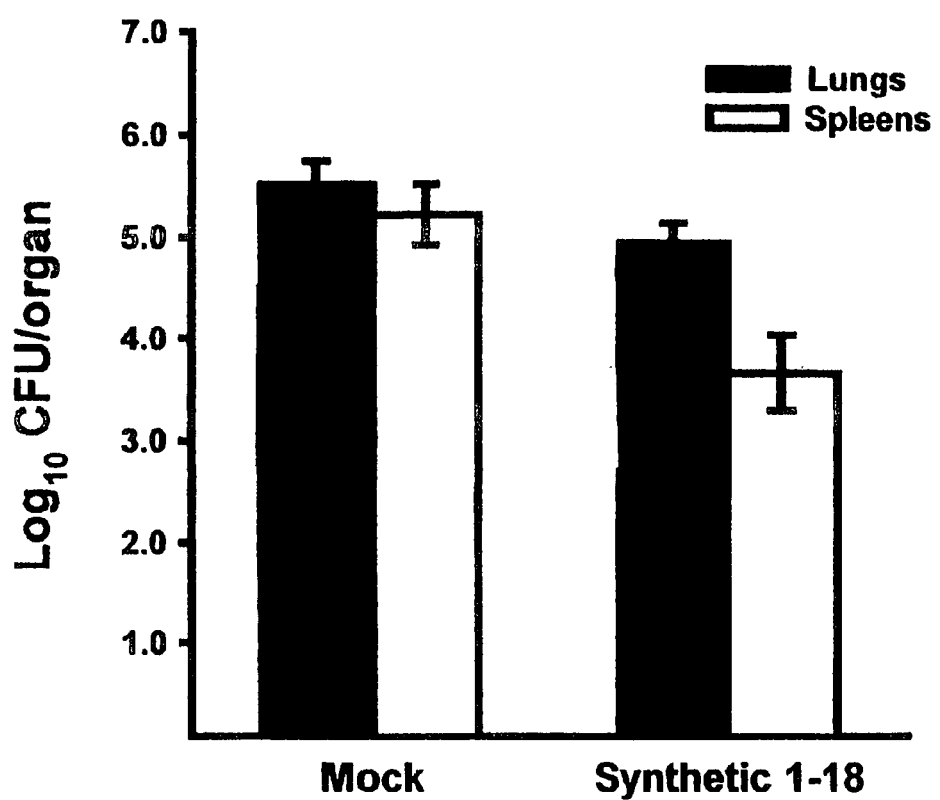
FIG. 11. Protective efficacy of Ag2/PRA (1–18) synthetic peptide against i.p. challenge. The vaccine efficacy of the Ag2/PRA (1–18) synthetic peptide was determined in BALB/c mice challenged by an i.p. route with 2,500 arthroconidia. Mice were immunized with the synthetic peptide dissolved in DMSO and admixed with Freund adjuvant. Mock controls were immunized with the same concentration of DMSO in adjuvant. Results are expressed as the $\log_{10}$ CFU (mean±standard error) in tissues from groups of 10 mice at day 12 postinfection.

To confirm that the vaccine efficacy of the Ag2/PRA (1–18) DNA could be reproduced using a synthetic Ag2/PRA (1–18) peptide, mice were given three weekly immunizations of. 10 μg of a synthetic Ag2/PRA (1–18) peptide which was dissolved in DMSO (final concentration of 12.5%) and then mixed with Freund adjuvant. Control mice received an identical amount of DMSO alone in adjuvant. As shown in FIG. 11, the results established that the Ag2/PRA (1–18) synthetic peptide induced protection, as measured by reduced fungal load in the spleens (P<0.008) after an i.p. challenge.

Protection against pulmonary challenge is achievable using a microparticle delivery system, such as the poly (lactide-co-glycolide)(PLG) microparticles produced by Chiron Corporation. PLG microparticles containing one or more of the Ag2/PRA cDNA constructs are readily prepared. Also, monoepitopic complexes comprising multiple repeating units of the signal peptide have the advantage that they direct immunity to the protective epitopes while avoiding the induction of antibody to other domains within Ag2/PRA.

4. Vaccine Efficacy of Ag2/PRA (19–194) with TPA Signal Sequence

In Example V, the Ag2/PRA (19–194) DNA construct showed reduced vaccine capacity as compared to the full-length Ag2/PRA (1–194) DNA construct. This reduced efficacy encouraged the present inventors to investigate the vaccine capacity of the signal peptide. As shown in the present example, the signal peptide DNA construct provides protection to essentially the same degree as the full length construct.

However, the inventors realized that the reduced efficacy of the Ag2/PRA (19–194) DNA construct could be attributable, in part, to the fact that the truncated Ag2/PRA (19–194) DNA and the pVR1012 vector used to deliver Ag2/PRA (19–194) DNA lacked any signal sequence. Absent a signal sequence, the intracellular processing may be altered or the translated peptide may not be secreted (or secreted at diminished levels) and, as a consequence, have reduced exposure to antigen-presenting cells. The following study was therefore conducted to examine the effect of using a vector with another signal sequence for delivering the Ag2/PRA (19–194) DNA.

Figure 12:
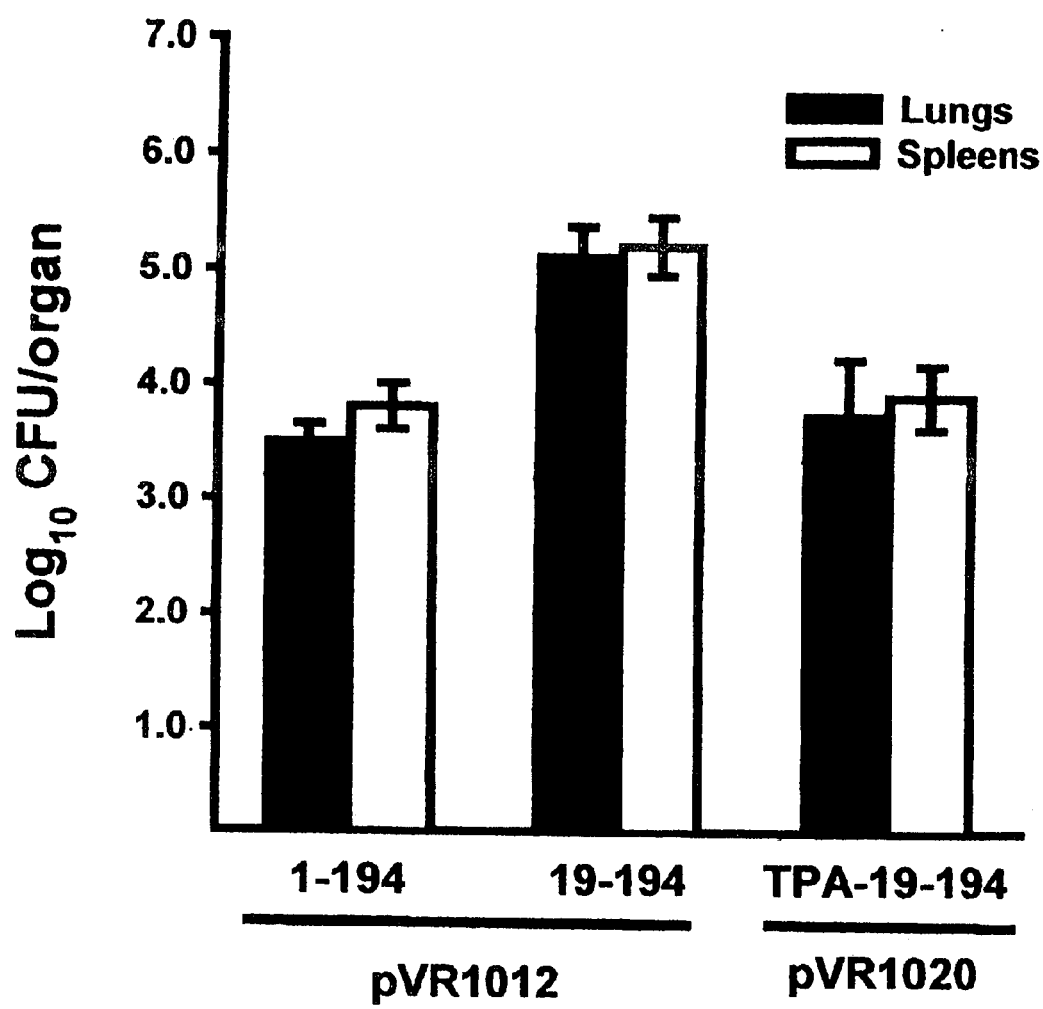
FIG. 12. Effect of TPA leader sequence on the vaccine capacity of Ag2/PRA (19–194) DNA. Results are expressed as the $\log_{10}$ CFU (mean±standard error) in tissues from groups of 10 mice immunized with Ag2/PRA (19–194) DNA or the TPA-Ag2/PRA (19–194) DNA construct and then sacrificed 12 days after i.p. challenge with 2,500 arthroconidia.

The pVR1020 vector was employed, which contains the tissue plasminogen activator (TPA) signal sequence (Delogu et al., 2002; Li et al., 1999), and the Ag2/PRA (19–194) DNA sequence was inserted in this vector. As shown in FIG. 12, mice immunized with Ag2/PRA (19–194) ligated to pVR1020 were significantly more protected than mice immunized with Ag2/PRA (19–194) ligated to pVR1012. However, these results in no way negate the foregoing data showing that, irrespective of the initial motivation for conducting the signal peptide studies, mice immunized with the signal sequence are protected to a level comparable to that resulting from the use of the full-length Ag2/PRA.

Figure 13A:
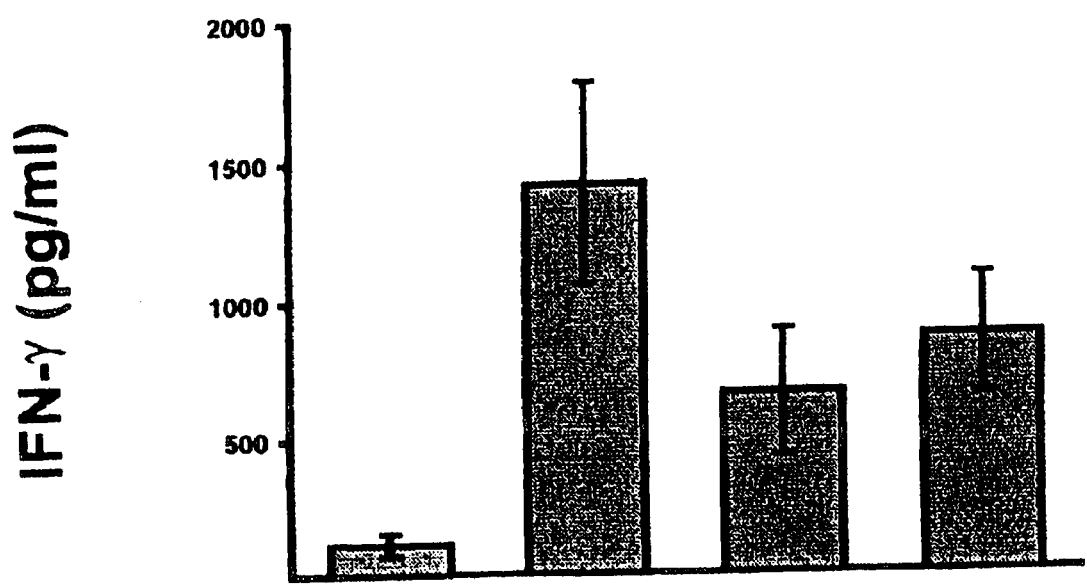
FIG. 13A and FIG. 13B. IFN-γ production by in vitro stimulated spleen cells from immunized mice. Spleen cells were pooled from groups of 10 mice and stimulated with the full-length GST-Ag2/PRA recombinant protein (FIG. 13A) or the synthetic signal peptide (FIG. 13B) for 48 h, and the supernatants were assayed for IFN-γ by an ELISA.
Figure 13B:
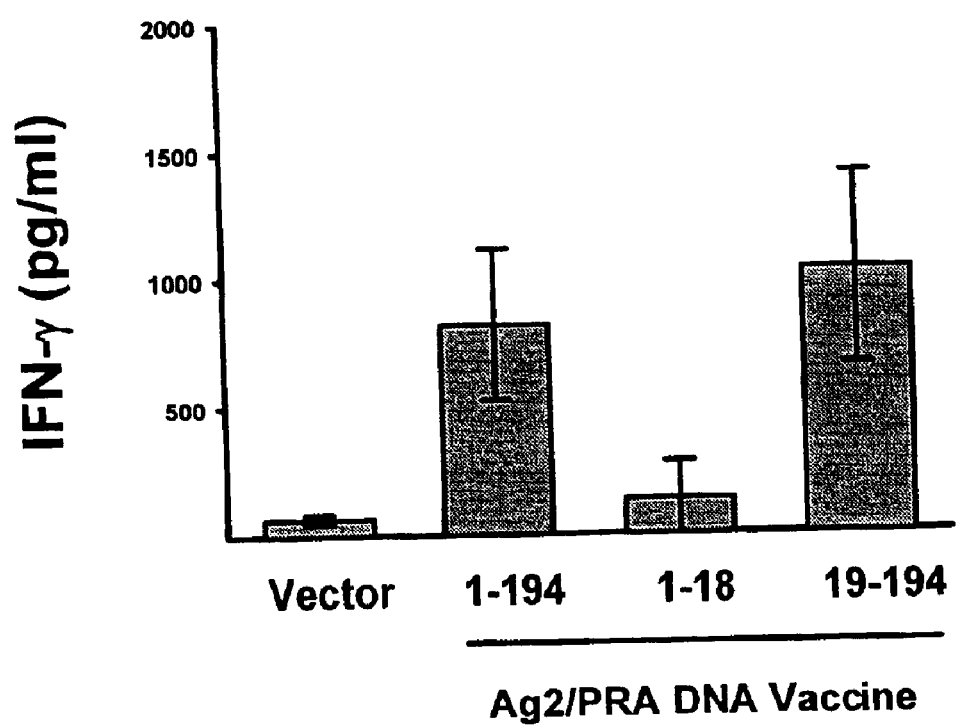

5. Induction of IFN-γ by Ag2/PRA DNA Constructs Studies were next undertaken to assess the immune response to the signal peptide sequence. Production of the T-helper1-associated cytokine IFN-γ is important in the host defense against *C. immitis* (Magee and Cox, 1995; 1998) and the Ag2/PRA (1–194) cDNA is known to induce the IFN-γ (Jiang et al., 1999b;c). To determine whether the protection induced by the Ag2/PRA (1–18) DNA vaccine was associated with the production of this cytokine, splenocytes were collected from mice 12 days after i.p. challenge and stimulated in vitro with recombinant Ag2/PRA, which contained the full-length sequence with an N-terminus GST peptide moiety (Zhu et al., 1996a). The results are shown in FIG. 13A and FIG. 13B.

Spleen cells from mice immunized with Ag2/PRA (1–194) DNA secreted 1,422 pg of IFNγ in response to stimulation with recombinant GST-Ag2/PRA (1–194) (FIG. 13A). Splenocytes from mice immunized with Ag2/PRA (19–194) and Ag2/PRA (1–18) secreted 663 pg/ml and 868 pg/ml, respectively. The IFN-γ responses did not differ significantly between the three groups of mice, and all three groups showed significant IFN-γ production as compared to control mice (P<0.05).

These results establish that all three constructs express one or more IFN-γ-inducing epitopes and, on the basis that there are no sequence homologies between the Ag2/PRA (1–18) DNA and Ag2/PRA (19–194) DNA (Zhu et al., 1996a;b), the epitopes expressed by these two constructs differ in composition. This concept was confirmed by the results shown in FIG. 13B, wherein the synthetic Ag2/PRA (1–18) peptide induced IFN-γ production in spleens cells from mice immunized with Ag2/PRA (1–194) DNA or Ag2/PRA (1–18) DNA, but not Ag2/PRA (19–194).

6. Humoral Immune Response to Ag2/PRA cDNA Constructs

Figure 14:
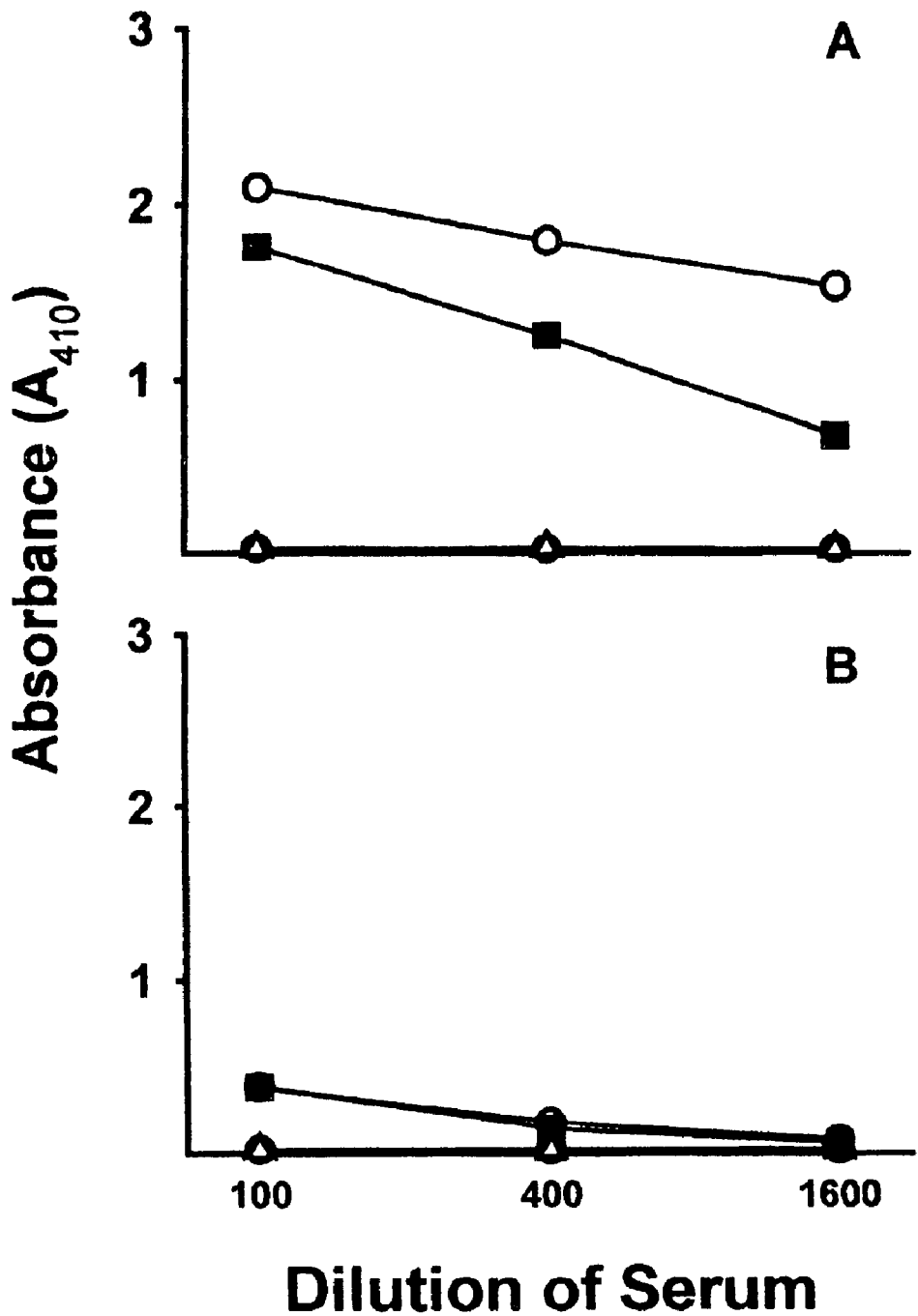
FIG. 14A and FIG. 14B. IgG1 (FIG. 14A) and IgG2a (FIG. 14B) isotype responses in mice vaccinated with Ag2/PRA (1–18) DNA, Ag2/PRA (19–194) DNA (closed squares), Ag2/PRA (1–194) DNA (open circles), or the pVR1012 vector alone, as measured by an ELISA using full-length GST-Ag2/PRA recombinant protein as the target antigen. Results depict mean antibody levels in assays of sera pooled from groups of 10 mice 12 days after i.p. challenge with 2,500 arthroconidia. Similar results were obtained from 3 independent studies.

To further characterize the nature of the immune response to the constructs, serum was collected from immunized, infected mice 12 days after challenge and assayed for anti-Ag2/PRA IgG isotype response using the recombinant GST-Ag2/PRA fusion protein as the target antigen. Consistent with the inventors' earlier report (Jiang et al., 1999b), Ag2/PRA (1–194) DNA induces both IgG1 and IgG2a, at an approximate ratio of 5:1 (FIG. 14A and FIG. 14B). The truncated Ag2/PRA (19–194) DNA induced a similar profile of antibody response, although the level of IgG1 was decreased. In marked contrast to the antibody response induced by the full-length Ag2/PRA (19–194) DNA and Ag2/PRA (19–194) DNA, neither anti-*Coccidioides* IgG1 nor IgG2a were detected in sera of mice immunized with Ag2/PRA (1–18) DNA (FIG. 14A and FIG. 14B).

C. Discussion

The present example shows that the signal peptide sequence of Ag2/PRA can induce protective immunity against this fungal pathogen. The protective immunity induced by the signal peptide gene alone was equal to that induced by the full-length Ag2/PRA gene vaccine, as evidenced by the decreased fungal loads in spleen and lung after i.p. challenge with a lethal dose of *C. immitis* and increased survival over a 40-day period postinfection. The protective immunity induced by the signal sequence was associated with the induction of IFN-γ and was not associated with the production of anti-*Coccidioides* IgG antibody.

In contrast to the vaccine efficacy of the Ag2/PRA (1–18) gene vaccine, the truncated Ag2/PRA (19–194) DNA vaccine, which lacks signal sequence, was much less effective in inducing protection and IFN-γ, but did induce anti-*Coccidioides* IgG, similar to the levels induced by the full-length Ag2/PRA gene vaccine. Expression of the truncated Ag2/PRA (19–194) DNA fused to the TPA signal sequence enhanced its protective capacity, most likely as a result of increased secretion with elevated uptake by antigen-processing cells.

This is the first report that immunization with a signal sequence alone can induce protective immunity. However, signal sequences have recently received increased attention in vaccine-induced immune responses (Baldwin et al., 1999; Jiang et al., 1999a; Haddad et al., 1998; Kamath et al., 1999). In one study, Haddad et al. (1998) reported that a DNA vaccine containing or lacking a signal sequence induced differential induction of IgG subclasses. In these studies, serum IgG1 response predominated when mice were immunized with signal sequence-containing DNA vaccine, while mixed IgG1/IgG2a profiles were obtained in mice given the DNA vaccine lacking signal sequence.

In a separate study, Drew et al. (2000) found that secreted form of DNA vaccine *Taenia ovis* 45W that contains signal sequence induced a stronger IgG response in BALB/c mice than did the DNA vaccine lacking signal sequence. In an animal model of tuberculosis, Baldwin et al. (1999) indicated that in addition to the effects on humoral immune response, immunization with Ag85A DNA vaccine containing the signal sequence induced a stronger protective immunity against tuberculosis than mice immunized with Ag85A DNA lacking signal sequence. Similar findings were reported by other investigators in studies of an Ag85B DNA vaccine (Kamath et al., 1999).

While the foregoing investigators showed that the signal sequence could play an important role in modifying DNA vaccine-mediated protective immunity, they did not directly examine the protective capacity or immunogenicity of the signal sequence alone. In the present example, the inventors show that the signal sequence alone can protect mice against challenge and that the protective capacity of the signal sequence correlated with the induction of IFN-γ.

The signal sequence Ag2/PRA (1–18) DNA vaccine induced protection against *C. immitis*, at a level comparable to that obtained with the full-length gene, but differed from the latter in that the signal sequence vaccine did not induce detectable antibody. This lack of antibody detection is not attributable to the absence of the N-terminal signal sequence region on the Ag2/PRA fusion protein used as a target antigen in the ELISA. That is, the gene encoding the GST peptide was inserted upstream of Ag2/PRA cDNA and, hence, was expressed on the N-terminus preceding the signal peptide sequence (Zhu et al., 1996a).

The deduction that the signal peptide lacks a B cell-reactive epitope is in accordance with the inventors' earlier finding that sera from patients with active coccidioidomycosis recognized the recombinant GST-Ag2/PRA (1–194) fusion protein in immunoblots, but did not react with a recombinant GST-Ag2/PRA (1–18) peptide (Zhu et al., 1997). The protective capacity of Ag2/PRA (1–18) DNA in the absence of a detectable antibody response is also consistent with earlier studies that antibodies are inconsequential to host resistance to *C. immitis* (Cox, 1993; Cox and Magee, 1998).

The inventors have previously reported that the production of IFN-γ is a surrogate marker of host resistance to *C. immitis* (Cox and Magee, 1998; Jiang et al, 1999a;b;c; Magee and Cox, 1995). Native, recombinant, and gene vaccines of *C. immitis* that were shown to protect against challenge with this fungus have consistently induced IFN-γ and, conversely, vaccine preparations that failed to induce protection did not induce this cytokine. While it has been widely assumed that the IFN-γ response in coccidioidomycosis represents activation of T-helper 1 (Th1) cells, it may be that it is also associated with the activation of cytotoxic T lymphocytes (CTL).

In support of this possibility, a database search of published MHC motifs (Parker et al., 1994) revealed a high probability that the translated Ag2/PRA (1–18) signal sequence contains an MHC Class I binding motif. Although cytotoxic T lymphocyte (CTL) activity has not been reported in coccidioidomycosis, a role for CD8$^+$ T cells in host defense is suggested by the finding that optimal protection by adoptive transfer of immune spleen cells to syngeneic mice was obtained when both CD4 and CD8 cells were present. That is, depletion of either subset population reduced the level of protection conferred to recipient mice (Cox and Magee, 1998).

The results of the present study further predict that the IFN-γ-inducing epitope on Ag2PRA (1–18) differs from that on Ag2/PRA (19–194). This prediction is made on the basis that the two constructs do not share sequence homology, yet both induce IFN-γ, and the sum of the IFN-γ levels induced by the two constructs approximates that induced by the full-length Ag2/PRA (1–194) gene. This concept is further supported by the finding that splenocytes from mice immunized with the Ag2/PRA (1–18) signal sequence or the full length Ag2/PRA DNA, but not Ag2/PRA (19–194) produced IFN-γ in response to stimulation with the Ag2/PRA (1–18) synthetic peptide. Given the data of the present invention, the nature and location of the IFNγ-inducing epitopes of Ag2/PRA, and the T cell population(s) that are activated, can now be delineated.

MHC Class-I binding activity has been recently recognized as an important function of signal peptide for in vivo processing and antigen presentation during DNA immunization. The present results show that the Ag2/PRA (1–18) DNA vaccine, which is predicted to have MHC-I binding activity, induced protective immunity, whereas Ag2/PRA (M1–18), which contains a frame shift mutation, was nonprotective and lacked predictable MHC-I binding activity. Therefore, the CD8+ CTL can be predicted to be an important component for the signal gene vaccine's efficacy to induce protective immunity.

In addition to functioning as antigen epitope to induce protective immunity, the Ag2/PRA signal sequence also functions as secretion signal to transport native Ag2/PRA protein out of cells to stimulate immune responses (Martoglio and Dobberstein, 1998). Ag2/PRA (19–194) DNA, which lacked a signal sequence, was less protective than the full-length Ag2/PRA (1–194) DNA. The addition of the TPA signal sequence to Ag2/PRA (19–194) DNA potentiated the vaccine capacity of the Ag2/PRA (19–194) DNA. Li et al. (1999) and Delogu et al. (2002) have shown that fusion of *Mycobacterium tuberculosis* DNA vaccine candidates with the TPA signal sequence increased their expression as secreted proteins and significantly enhanced their immunogenicity in mice.

In summary, the present invention shows that the Ag2/PRA signal sequence alone is an effective vaccine against coccidioidomycosis. This is the first study to show that the signal sequence of a *Coccidioides* spp. gene is able to induce protective immunity against challenge with this fungal pathogen. This investigation demonstrates that the role of signal sequence is not only to transport mature protein, but more importantly, to function as an immunoepitope in the induction of immune response.

EXAMPLE VII

Expression Library Immunization (ELI)

To identify other immunoprotective antigens of *C. immitis*, expression library immunization (ELI) is used. cDNA expression libraries have been prepared from spherules grown in BALB/c peritoneal macrophages and, for comparative analysis, spherules grown in tissue culture medium alone. The libraries are screened using the expression library immunization technique (Barry et al., 1995; Piedrafita et al., 1999; Smooker et al., 2000). A single protective gene can be demonstrated when present at a ratio of only 1 of 27,000–30,000 plasmids.

In this approach, sublibraries are prepared, each containing approximately 100 plaques. The plaques are plated and examined for Ag2 by oligonucleotide hybridization. Ag2-positive plaques are excised from the plate and cloned separately for a positive control. Analysis of the Ag2 plasmids determines the range of concentration needed to show protection, thus allowing other protective genes to be cloned.

Ag2-negative plaques are amplified, mass excised, plated and pooled for direct immunization of mice. Sublibraries that show protective capacity are subdivided and each mini-library evaluated as before. Protective clones are sequenced and further evaluated for vaccine efficacy. Sublibraries that are shown to induce protection are screened for cDNAs such as URE or SOWgp prior to subcloning.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abuodeh, Shubitz, Siegel, Snyder, Peng, Orsborn, Brummer, Stevens, Galgiani, "Resistance to *Coccidioides immitis* in mice after immunization with recombinant protein or a DNA vaccine of a proline-rich antigen," *Infect. Immun.*, 67:2935–2940, 1999.

Ampel, Bejarano, Salas, Galgiani, "In vitro assessment of cellular immunity in human coccidioidomycosis: relationship between dermal hypersensitivity, lymphocyte transformation, and lymphokine production by peripheral blood mononuclear cells from healthy adults," *J. Infect. Dis.*, 165:710–715, 1992.

Ampel, "In vitro production of tumor necrosis factors by adherent human peripheral blood mononuclear cells incubated with killed coccidioidal arthroconidia and spherules," *Cell. Immunol.*, 153:248–255, 1994.

*Antibodies: A Laboratory Manual*, Cold Spring Harbor Laboratory, 1988.

Azuma et al., "Correlation Between Augmented Resistance to Influenza Virus Infection and Histological Changes in Lung of Mice Treated with Trehalose-6,6'-dimycolate," *Journal of Biological Response Modifiers*, 7:473–482, 1988.

Babiuk, "Broadening the approaches to developing more effective vaccines," *Vaccine*, 17:1587–1595, 1999.

Baker et al., "Ability of Monophosphoryl Lipid A To Augment the Antibody Response of Young Mice," *Infection and Immunity*, 56(12):3064–3066, 1988a.

Baker et al., "Inactivation of Suppressor T-Cell Activity by Nontoxic Monophosphoryl Lipid A," *Infection and Immunity*, 56(5):1076–1083, 1988b.

Baker et al., "Structural Features That Influence the Ability of Lipid A and Its Analogs To Abolish Expression of Suppressor T Cell Activity," *Infection and Immunity*, 60(7):2694–2701, 1992.

Baker et al., "Molecular structures that influence the immunomodulatory properties of the lipid A and inner core region oligosaccharides of bacterial lipopolysaccharides," *Infection Immunity*, 62(6):2257–2269, 1994.

Bakker et al., "Melanocyte lineage-specific antigen gp100 is recognized by melanoma-derived tumor-infiltrating lymphocytes," *J. Exp. Med.*, 179:1005, 1994.

Baldwin, D'Souza, Orme, Liu, Huygen, Denis, Tang, Zhu, Montgomery, Ulmer, "Immunogenicity and protective efficacy of DNA vaccines encoding secreted and non-secreted forms of *Mycobacterium tuberculosis* Ag85A," *Tubercle and Lung Dis.*, 79:251–259, 1999.

Barry, Lal, Johnston, "Protection against mycoplasma infection using expression-library immunization," *Nature*, 377:632–634, 1995.

Beaman, Pappagianis, Benjamini, "Significance of T cells in resistance to experimental murine coccidioidomycosis," *Infect. Immun.*, 17:580–585, 1977.

Beaman, Benjamini, Pappagianis, "Role of lymphocytes in macrophage-killing of *Coccidioides immitis* in vitro," *Infect. Immun.*, 34:347–353, 1981.

Beaman, "Fungicidal activation of murine macrophages by recombinant gamma interferon," *Infect Immun.*, 55:2951–2955, 1987.

Bennett et al., "Endogenous Production of Cytotoxic Factors in Serum of BCG-Primed Mice by Monophosphoryl Lipid A, a Detoxified Form of Endotoxin," *Journal of Biological Response Modifiers*, 7:65–76, 1988.

Bouwer, Ninrichs, Barry, "Genetic immunization of mice against *Listeria monocytogenes* using plasmid DNA encoding listeriolysin O," *J. Immunol.*, 163:322–329, 1999.

Bowness et al., "Clostridium perfringens enterotoxin is a superantigen reactive with human T cell receptors V beta 6.9 and V beta 22," *J. Exp. Med.*, 176(3):893–896, 1992.

Brade et al., "An Artificial Glycoconjugate Containing the Bisphosphorylated Glucosamine Disaccharide Backbone of Lipid A Binds Lipid A Monoclonal Antibodies," *Infection and Immunity*, 61(10):4514–4517, 1993.

Brutlag et al., *CABIOS*, 6:237–245, 1990.

Campbell, In: *Monoclonal Antibody Technology, Laboratory Techniques in Biochemistry and Molecular Biology*, Vol. 13, Burden and Von Knippenberg, Eds. pp. 75–83, Amsterdam, Elseview, 1984.

Chase et al., "Effect of Monophosphoryl Lipid A on Host Resistance to Bacterial Infection," *Infection and Immunity*, 53(3):711–712, 1986.

Chen et al., "Activation of Macrophages From Aging Mice by Detoxified Lipid A," *Journal of Leukocyte Biology*, 49:416–422, 1991.

Chou and Fasman, "Prediction of Protein Conformation," *Biochemistry*, 13(2):222–245, 1974a.

Chou and Fasman, "Conformational Parameters for Amino Acids in Helical, β-Sheet, and Random Coil Regions Calculated from Proteins," *Biochemistry*, 13(2):211–222, 1974b.

Chou and Fasman, "Prediction of the Secondary Structure of Proteins from Their Amino Acid Sequence," *Adv. Enzymol. Relat. Areas Mol. Biol.*, 47:45–148, 1978a.

Chou and Fasman, "Empirical Predictions of Protein Conformation," *Ann. Rev. Biochem.*, 47:251–276, 1978b.

Chou and Fasman, "Prediction of β-Turns," *Biophys. J.*, 26:367–384, 1979.

Chow, Chiang, Lee, Chi, Lin, Chen, Tao, "Development of Th1 and Th2 populations and the nature of immune responses to hepatitis B virus DNA vaccines can be modulated by codelivery of various cytokine genes," *J. Immunol.*, 160:1320–1329, 1998.

Cole, Chinn Jr., Pope, Starr, "Characterization and distribution of 3-O-methylmannose in *Coccidioides immitis*, In: *Proceedings of The Fourth International Conference on Coccidioidomycosis*, H. E. Einstein, and A. Catanzaro (ed.) The National Foundation for Infectious Disease, Washington, D.C., p. 130–145, 1985.

Corry, Ampel, Christian, Locksley, Galgiani, "Cytokine production by peripheral blood mononuclear cells in human coccidioidomycosis," *J. Infect. Dis.*, 174:440–443, 1996.

Cox and Britt, "Isolation of a coccidioidin component that reacts with immunoglobulin M precipitin antibody," *Infect. Immun.*, 53:449–452, 1986.

Cox and Magee, "Protective immunity in coccidioidomycosis," *Res. Immunology*, 149:417–428, 1998.

Cox and Vivas, "Spectrum of in vivo and in vitro immune responses in coccidioidomycosis," *Cell. Immunol.*, 31:130–141, 1977.

Cox et al., *J. Virol.* 67(9):5664–5667, 1993.

Cox, "Antigenic structure of *Coccidioides immitis*," In: *Immunology of Fungal Diseases*, E. Kurstak, G. Marquis, P. Auger, L. De Repentigny, and S. Montplaisir (ed.), Marcel Dekker, Inc., New York., p. 133–170, 1989.

Cox, "Coccidioidomycosis," In: *Fungal Infections and Immune Responses*, J. W. Murphy, H. Friedman, and M. Bendinelli (ed.), Plenum Press, New York, p. 173–211, 1993.

Cox, Brummer, Lecara, "In vitro lymphocyte responses of coccidioidin skin-test positive and—negative persons to coccidioidin, spherulin, and a *Coccidioides immitis* cell wall antigen," *Infect. Immun.*, 15:751–755, 1977.

Cox, Kennell, Boncyk, Murphy, "Induction and expression of cell-mediated immune responses in inbred mice infected with *Coccidioides immitis*, *Infect Immun.*, 56:13–17, 1988.

Deavin et al., *Mol. Immunol.*, 33:145–55, 1996.

Degano, Schenider, Hannan, Gilbert, and Hill, "Gene gun intradermal DNA immunization followed by boosting with modified vaccinia virus Ankara: enhanced CD8+ T cell immunogenicity and protective efficacy in the influenza and malaria models," *Vaccine*, 18:623–632, 2000.

Delogu, Li, Repique, Collins, Morris, "DNA vaccine combinations expressing either tissue plasminogen activator signal sequence fusion proteins or ubiquitin-conjugated antigens induce sustained protective immunity in a mouse model of pulmonary tuberculosis," *Infect. Immun.*, 70:292–302, 2002.

Dobberstein, "On the beaten pathway," *Nature*, 367:599–600, 1994.

Dooley, Cox, Hestilow, Dolan, Magee, "Cytokine induction in human coccidioidomycosis," *Infect. Immun.*, 62:3980–3983, 1994.

Drew, Lightowlers, Strugnell, "Humoral immune response to DNA vaccines expressing secreted membrane bound and non-secreted forms of the *Taenia ovis* 45W antigen," *Vaccine*, 18:2522–2532, 2000.

Dugger, Villareal, Ngyuen, Zimmermann, Law, Galgiani, "Cloning and sequence analysis of the cDNA for a protein from *Coccidioides immitis* with immunogenic potential," *Biochem. Biophys. Res. Commun.*, 218:485489, 1996.

Elliott et al., "The D-Galactosamine Loaded Mouse and Its Enhanced Sensitivity to Lipopolysaccharide and Monophosphoryl Lipid A: A Role for Superoxide," *J. Immunol.*, 10:69–74, 1991.

Fetrow & Bryant, "New Prograns for Protein Tertiary Structure Prediction," *BIOTECHNOLOGY*, 11:479–483, 1993.

Fisher, Loenig, White, Taylor, "Molecular and phenotypic description of *Coccidioides posadasii* sp. nov., previously recognized as the non-California population of *Coccidioides immitis*," *Mycologia*, 94(1):73–84, 2002.

Fitzgerald, "Syphilis vaccine: up-regulation of immunogenicity by cyclophosphamide, Ribi adjuvant, and indomethacin confers significant protection against challenge infection in rabbits," *Vaccine*, 9:265–272, 1991.

Franco et al., *J. Gen. Virol.*, 74:2579–2586, 1993.

Franke, Sette, Sacci, Jr., Southwood, Corradin, and Hoffman, "A subdominant CD8+ cytotoxic T lymphocyte (CTL) epitope from the Plasmodium yoelii circumsporozoite protein induces CTLs that eliminate infected hepatocytes from culture", *Infect. Immun.*, 68:3403–3411, 2000.

Fynan et al., "DNA vaccines: Protective immunizations by parenteral, mucosal, and gene-gun inoculations," *Proc. Natl. Acad. Sci. USA*, 90:11478–11482, 1993.

Garg & Subbarao, "Immune Responses of Systemic and Mucosal Lymphoid Organs to Pnu-Immune Vaccine as a Function of Age and the Efficacy of Monophosphoryl Lipid A as an Adjuvant," *Infection and Immunity*, 60(6):2329–2336, 1992.

Goding, In: *Monoclonal Antibodies: Principles and Practice*, 2d ed., Orlando, Fla., Academic Press, pp. 60–61, 65–66, 71–74, 1986.

Grabarek et al., "Endotoxic Lipid A Interaction with Human Platelets," *Journal of Biological Chemistry*, 265(14):8117–8121, 1990.

Gurunathan, Wu, Freidag, Seder, "DNA vaccines: a key for inducing long-term cellular immunity," *Current Opinions Immunol.*, 12:442–447, 2000.

Haddad, Liljeqvist, Stahl, Perlmann, Berzins, Ahlborg, "Differential induction of immunoglobulin G subclasses by immunization with DNA vectors containing or lacking a signal sequence," *Immunol. Lett.*, 61:201–204, 1998.

Harding, Kihlberg, Elofsson, Magnusson, Unanue, "Glycopeptides bind MHC molecules and elicit specific T cell responses," *J. Immunol.*, 151:2419–2424, 1993.

Hoffman, "Antigen processing: a new pathway discovered," *Science*, 255:1214–1215, 1992.

Hota-Mitchell, Clarke, Podesta, Dekaban, "Recombinant vaccinia viruses and gene gun vectors expressing the large subunit of *Schistosoma mansoni* calpain used in a murine immunization-challenge model," *Vaccine*, 17:1338–1354, 1999.

Hraba et al., "The Influence of Monophosphoryl Lipid A (MPL™) on Erythrocyte Autoantibody Formation," *Immunobiol.*, 189:448–456, 1993.

Hui, Mancini, Li, Wang, Tiollais, Michel, "Immunization with a plasmid encoding a modified hepatitis B surface antigen carrying the receptor binding site for hepatocytes," *Vaccine*, 17:1711–1718, 1999.

Hunter et al., *Vaccine*, 9:250: 1991.

Huppert, Spratt, Vukovich, Sun, Rice, "Antigenic analysis of coccidioidin and spherulin determined by two-dimensional immunoelectrophoresis," *Infect. Immun.*, 20:542–551, 1978.

Ishioka, Lamont, Thomson, Bulbow, Gaeta, Sette, Grey, "MHC interaction and T cell recognition of carbohydrates and glycopeptides," *J. Immunol.*, 148:2446–2451, 1992.

Jameson and Wolf, "The antigenic index: a novel algorithm for predicting antigenic determinants," *Comput. Appl. Biosci.*, 4:181–186, 1988.

Jentoft, "Why are proteins O-glycosylated?," *Trends Biochem. Sci.*, 15:291–294, 1990.

Jiang, Magee, Cox, "Construction of a single chain interleukin-12-expressing retroviral vector and its application in cytokine gene therapy against experimental coccidioidomycosis," *Infect. Immun.*, 67:2996–3001, 1999a.

Jiang, Magee, Cox, "Coadministration of interleukin 12 expression vector with Antigen 2 cDNA enhances induction of protective immunity against *Coccidioides immitis*," *Infect. Immun.*, 67:5848–5853, 1999b.

Jiang, Magee, Quitugua, Cox, "Genetic vaccination against *Coccidioides immitis*: comparison of vaccine efficacy of recombinant antigen 2 and antigen 2 cDNA," *Infect. Immun.*, 67:630–635, 1999c.

Johnson and Tomai, "A Study of the Cellular and Molecular Mediators of the Adjuvant Action of a Nontoxic Monophosphoryl Lipid A," *Adv. Exp. Med. Biol*, 133:567–579, 1988.

Johnson et al., "Structural Characterization of Monophosphoryl Lipid A Homologs Obtained from *Salmonella minnesota* Re595 Lipopolysaccharide," *J. Biol. Chem.*, 265(14):8108–8116, 1990.

Kamath, Feng, Macdonald, Briscoe, Britton, "Differential protective efficacy of DNA vaccines expressing secreted proteins of *Mycobacterium tuberculosis*," *Infect. Immun.*, 67:1702–1707, 1999.

Kirkland, Finley, Orsbom, Galgiani, "Evaluation of the proline-rich antigen of *Coccidioides immitis* as a vaccine candidate in mice," *Infect. Immun.*, 66:3519–3522, 1998.

Kohler and Milstein, *Nature*, 256:495–497, 1975.

Kohler and Milstein, *Eur. J. Immunol.*, 6:511–519, 1976.

Kondo et al, *J. Virol.*, 69:6735–6741, 1995.

Kong, Levine, Smith, "Immunogenic properties of nondisrupted and disrupted spherules of *Coccidioides immitis* in mice," Sabouraudia, 2:131–142, 1963.

Kovach et al., "Lipid $IV_A$ Inhibits Synthesis and Release of Tunor Necrosis Factor Induced by Lipopolysaccharide in Human Whole Blood Ex Vivo," *J. Exp. Med.*, 172:77–84, 1990.

Kyte and Doolittle, "A simple method for displaying the hydropathic character of a protein". *J. Mol. Biol.*, 157(1): 105–132, 1982.

Lecara, Cox, Simpson, "*Coccidioides immitis* vaccine: potential of an alkali-soluble, water-soluble cell wall antigen," *Infect. Immun.*, 39:473–475, 1983.

Lee, Corr, Carson, "Control of immune responses by gene immunization," *Ann. Med.* 30:460–468, 1998.

Levine, Cobb, Smith, "Immunogenicity of spherule-endospore vaccines of *Coccidioides immitis* for mice," *J. Immunol.*, 87:218–227, 1961.

Levine, Kong, Smith, "Immunization of mice to *Coccidioides immitis*: dose, regimen and spherulation stage of killed spherule vaccines," *J. Immunol.*, 94:132–142, 1965.

Li, Howard, Kelley, Delogu, Collins, Morris, "Immunogenicity of DNA vaccine expressing tuberculosis proteins fused to tissue plasminogen activator signal sequence," *Infect. Immun.*, 67:4780–4786, 1999.

Livingston et al., "The Serologic Response to Meth A Sarcoma Vaccines After Cyclophosphamide Treatment is Additionally Increased by Various Adjuvants," *The Journal of immunology*, 135(2):1505–1509, 1985.

Madonna and Vogel, "Induction of Early-Phase Endotoxin Tolerance in Athymic (Nude) Mice, B-Cell-Deficient (xid) Mice, and Splenectomized Mice," *Infection and Immunity*, 53(3):707–710, 1986.

Magee and Cox, "Roles of gamma interferon and interleukin-4 in genetically determined resistance to *Coccidioides immitis, Infect. Immun.*, 63:3514–3519, 1995.

Magee and Cox, "Interleukin-12 regulation of host defenses against *Coccidioides immitis*," *Infect. Immun.*, 64:3609–3613, 1996.

Maloy, Donachie, O'Hagan and Mowat, "Induction of mucosal and systemic immune responses by immunization with ovalbumin entrapped in poly(lactide-co-glycolide)microparticles", *Immunology*, 81:661–667, 1994.

Martoglio and Dobberstein, "Signal sequence: more than just greasy peptides," *Trends Cell Biology*, 8:410–415, 1998.

Masihi et al., "Effects of Nontoxic Lipid A and Endotoxin on Resistance of Mice to *Toxoplasma gondii*," *Journal of Biological Response Modifiers*, 7:535–539, 1988.

Mitchell et al., "Active specific immunotherapy of melanoma: Phase I trial of allogeneic lysates and a novel adjuvant," *Cancer Res.*, 48:5883–5893, 1988.

Mitchell et al., "Active specific Immunotherapy of melanoma with allogeneic cell lysates: Rationale, results and possible mechanisms of action," *Ann. N.Y. Acad. Sci.*, 690:153–166, 1993.

Mooney et al., "Bacterial superantigen signaling via HLA class II on human B lymphocytes," *Mol. Immunol.*, 31(9):675–681, 1994.

Mosmann and Coffman, "TH1 and TH2 cells: different patterns of lymphokine secretion lead to different functional properties," *Annu. Rev. Immunol.*, 7:145–173, 1989.

Myers et al., "Monophosphoryl Lipid A Behaves as a T-Cell-Independent Type 1 Carrier for Hapten-Specific Antibody Responses in Mice," *Infection and Immunity*, 63(1):168–174, 1995.

Nakamura et al., In: *Enyme Immunoassays: Heterogeneous and Homogeneous Systems*, Chapter 27.

Odean et al., "Involvement of Gamma Interferon in Antibody Enhancement by Adjuvants," *Infection and Immunity*, 58(2):427–432, 1990.

Pappagianis, Hector, Levine, Collins, "Immunization of mice against coccidioidomycosis with a subcellular vaccine," *Infect. Immun.*, 25:440–445, 1979.

Pappagianis, "Epidemiology of coccidioidomycosis," In: *Coccidioidomycosis*, D. A. Steven (Ed.), Plenum Publishing Corporation, New York, p. 63, 1980.

Pappagianis, "Marked increase in cases of coccidioidomycosis in California: 1991, 1992, and 1993," *Clin. Inf. Dis.*, 19:S14–18, 1994.

Parker, Bednarek, Coligan, "Scheme for ranking potential HLA-A2 binding peptides based on independent binding of individual peptide side-chains," *J. Immunol.*, 152:163, 1994.

Patek, Collians, Cohn, "Transformed cell lines susceptible or resistant to in vivo surveillance against tumorigenesis," *Nature*, 276:510–511, 1978.

Piedrafita, Xu, Hunter, Harrison, Liew, "Protective immune responses induced by vaccination with an expression genomic library of *Leishmania major*," *J. Immunol.*, 163:1467–1472, 1999.

Putney and Burke, "Improving protein therapeutics with sustained-release formulations", *Nat. Biotechnol.*, 16:153–157, 1998.

Rabinovich et al., "Vaccine Technologies: View to the Future," *Science*, 265:1401–1402, 1994.

Ravindranath et al., "Efficacy of tumor cell vaccine after incorporating monophosphoryl lipid A (MPL) in tumor cell membranes containing tumor-associated ganglioside," *Experientia*, 50:648–653, 1994a.

Ravindranath et al., "Attachment of Monophosphoryl Lipid A (MPL) to Cells and Liposomes Augments Antibody Response to membrane-bound Gangliosides," *Journal of Autoimmunity*, 7:803–816, 1994b.

Restifo, Bacik, Irvine, Yewdell, McCabe, Anderson, Eisenlohr, Rosenberg, Bennink, "Antigen processing in vivo and the elicitation of primary CTL responses," *J. Immunol.*, 154:4414–4422, 1995.

Ronaghy, Prakken, Takabayashi, Firestein, Boyle, Zvailfler, Roord, Albani, Carson, Raz, "Immunostimulatory DNA sequences influence the course of adjuvant arthritis." *J. Immunol.*, 168:51–56, 2002.

Rothbard and Taylor, *EMBO J.*, 7:93–100, 1988.

Rott et al., "Protection from experimental allergic encephalomyelitis by application of a bacterial superantigen," *Int. Immunol.*, 4(3):347–353, 1992.

Sambrook, Fritsch, Maniatis, *Molecular Cloning: A Laboratory Manual*, 2nd Ed., Cold Spring Harbor Press, Cold Spring Harbor, N.Y., 1989.

Sato et al., "Cytoplasmic membrane-associated protein (CAP) isolated from Streptococcus pyogenes: as a new bacterial superantigen," *Microbiol. Immunol.*, 38(2):139–147, 1994.

Schneider, Gilbert, Blanchard, Hanke, Robson, Hannan, Becker, Sinden, Smith, and Hill, *Nature Med.*, 4:397402, 1998.

Schwab et al., "Superantigen can reactivate bacterial cell wall-induced arthritis," *J. Immunol.*, 150(9):4151–4159, 1993.

Sin, Kim, Arnold, Shroff, McCallus, Pachuk, McElhiney, Wolf, Pompa-de Bruin, Higgins, Ciccarelli, Weiner, "IL-12 gene as a DNA vaccine adjuvant in a herpes mouse model: IL-12 enhances Th1-type CD4+ T cell-mediated protective immunity against herpes simplex virus-2 challenge," *J. Immunol.*, 162:2912–2921, 1999.

Slagle, Cox, Kuruganti, "Induction of tumor necrosis factor alpha by spherules of *Coccidioides immitis*," *Infect. Immun.*, 57:1916–1922, 1989.

Smooker, Setiady, Rainczuk, Spithill, "Expression library immunization protects mice against a challenge with virulent rodent malaria," *Vaccine*, 18:2533–2540, 2000.

Stevens, "Current Concepts: Coccidioidomycosis," *N. Eng. J. Med.*, 332:1077–1082, 1995.

Takada et al., "Molecular and Structural Requirements of a Lipoteichoic Acid from *Enterococcus hirae* ATCC 9790 for Cytokine-Inducing, Antitumor, and Antigenic Activities," *Infection and Immunity*, 63(1):57–65, 1995.

Tanamoto, "Free Hydroxyl Groups Are Not Required for Endotoxic Activity of Lipid A," *Infection and Immunity*, 62(5):1705–1709, 1994a.

Tanamoto, *FEBS Lett.*, 351:325–329, 1994b.

Tanamoto, "Dissociation of Endotoxic Activities in a Chemically Synthesized Lipid A Precursor after Acetylation," *Infection and Immunity*, 63(2):690–692, 1995.

Tang et al., *Nature*, 356:152–154, 1992.

Tomai and Johnson, "T Cell and Interferon-$\gamma$ Involvement in the Adjuvant Action of a Detoxified Endotoxin," *Journal of Biological Response Modifiers*, 8(6):625–643, 1989.

Tomai et al., "The Adjuvant Properties of a Nontoxic Monophosphoryl Lipid A in Hyporesponsive and Aging Mice," *Journal of Biological Response Modifiers*, 6:99–107, 1987.

Tsuji, Hamajima, Fulcushima, Xin, Ishii, Aoki, Ishigatsubo, Tani, Kawamoto, Nitta, Miyazaki, Koff, Okubo, Okuda, "Enhancement of cell-mediated immunity against HIV-1 induced by coinoculation of plasmid-encoded HIV-1 antigen with plasmid expressing IL-12;" *J. Immunol.*, 158:4008–4013.30, 1997.

Ulmer et al., "Heterologous Protection Against Influenza by Injection of DNA Encoding a Viral Protein," *Science*, 259:1745–1749, 1993.

Verma et al., "Adjuvant Effects of Liposomes Containing Lipid A: Enhancement of Liposomal Antigen Presentation and Recruitment of Macrophages," *Infection and Immunity*, 60(6):2438–2444, 1992.

Vosika et al., *Cancer Immunol. Immunother.*, 18:107, 1984.

Wang et al., *Proc. Natl. Acad. Sci. USA*, 90:4156–4160, 1993.

Weinberger et al., *Science*, 228:740–742, 1985.

Whitton et al., *J. Virol.* 67:(1)348–352, 1993.

Wolf et al., "An Integrated Family of Amino Acid Sequence Analysis Programs," *Comput. Appl. Biosci.*, 4(1):187–191, 1988.

Yamamoto et al., "In vitro Augmentation of Natural Killer Cell Activity and Production of Interferon-$\alpha/\beta$ and -$\gamma$ with Deoxyribonucleic Acid Fraction from *Mycobacterium bovis* BCG," *Jpn. J. Cancer Res.*, 79:866–873, 1988.

Yin et al., "Effect of Various Adjuvants on the Antibody Response of Mice to Pneumococcal Polysaccharides," *Journal of Biological Response Modifiers*, 8:190–205, 1989.

Zhu, Yang, Magee, Cox, "Molecular cloning and characterization of *Coccidioides immitis* Antigen 2 cDNA," *Infect. Immun.*, 64:2695–2699, 1996a.

Zhu, Yang, Magee, Cox, "*Coccidioides immitis* Antigen 2: analysis of gene and protein," *Gene*, 181:121–125, 1996b.

Zhu, Venkataprasad, Thangaraj, Hill, Singh, Ivanyi, Vordermeier, "Functions and specificity of T cells following nucleic acid vaccination of mice against *Mycobacterium tuberculosis*," *J. Immunol.*, 158:5921–5926, 1997a.

Zhu, Tryon, Magee, Cox, "Identification of a *Coccidioides immitis* Antigen 2 domain that expresses B-cell-reactive epitopes," *Infect. Immun.*, 65:3376–3380, 1997b.

Zimmermann, Johnson, Martens, White, Zimmer, Pappagianis, "Protection against lethal murine coccidioidomycosis by a soluble vaccine from spherules," *Infect. Immun.*, 66:2342–2345, 1998.

---

What is claimed is:

1. An isolated nucleic acid molecule that encodes a peptide consisting of the amino acid sequence of SEQ ID NO:2.

2. The nucleic acid molecule of claim 1, wherein said nucleic acid molecule is set forth as the nucleotide sequence of SEQ ID NO:1.

3. The nucleic acid molecule of claim 1, wherein said nucleic acid molecule is positioned under the control of a promoter.

4. The nucleic acid molecule of claim 1, wherein nucleic acid molecule is positioned in a recombinant vector.

5. The nucleic acid molecule of claim 1, comprised within a recombinant host cell.

6. The nucleic acid molecule of claim 1, comprised within a pharmaceutically acceptable carrier or diluent.

7. A recombinant vector that comprises an isolated nucleic acid molecule in accordance with claim 1.

8. A recombinant host cell that comprises an isolated nucleic acid molecule in accordance with claim 1.

9. The recombinant host cell of claim 8, wherein said host cell is a prokaryotic host cell.

10. The recombinant host cell of claim 8, wherein said host cell is a yeast host cell or a mammalian host cell.

11. A composition comprising an isolated nucleic acid molecule in accordance with claim 1 and a diluent.

12. The composition of claim 11, wherein said composition comprises a pharmaceutically acceptable carrier or diluent.

13. The composition of claim 11, wherein said composition further comprises at least an adjuvant.

* * * * *